US008653044B2

(12) United States Patent
Tower

(10) Patent No.: US 8,653,044 B2
(45) Date of Patent: Feb. 18, 2014

(54) SEX-SPECIFIC REGULATION OF AGING AND APOPTOSIS

(75) Inventor: John Tower, West Hollywood, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/811,413

(22) Filed: Jun. 7, 2007

(65) Prior Publication Data

US 2008/0305987 A1     Dec. 11, 2008

Related U.S. Application Data

(60) Provisional application No. 60/811,899, filed on Jun. 7, 2006.

(51) Int. Cl.
*A01N 43/04* (2006.01)

(52) U.S. Cl.
USPC ....................................... 514/44 A

(58) Field of Classification Search
None
See application file for complete search history.

(56) References Cited

U.S. PATENT DOCUMENTS

2005/0089857 A1* 4/2005 Tada et al. .................. 435/6

FOREIGN PATENT DOCUMENTS

WO     WO 2006/062701 A2   6/2006

OTHER PUBLICATIONS

Molecular Biology, 4th ed., 2007, Weaver, McGraw Hill, Boston, p. 850.*
Matoba et al, Proc. Natl. Acad. Sci. USA. 108 (51): 20621 (2011).*
Abraham, M.C. et al. 2004. "Death without caspases, caspases without death." TRENDS in Cell Biology. 14(4):184-193.
Ackerman, M. et al. 2003. "Senescence in a Bacterium with Asymmetric Division." Science. 300:1920.
Adams, J.M. 2003. "Ways of dying: multiple pathways to apoptosis." Genes & Development. 17:2841-2495.
Adams, J.M. et al. 2002. "Apoptosomes: engines or caspase activation." Cell division, growth and death. pp. 715-720.
Aigaki, T. et al. 2002. "Longevity determination genes in Drosophila melanogaster." Mechanisms of Ageing and Development. 123:1531-1541.
Amador-Noguez et al. 2005. "Gender-specific alterations in gene expression and loss of liver sexual dimorphism in the long-lived Ames dwarf mice." Biochemical and Biophysical Research Communications. 332:1086-1100.
Amikura, R. et al. 2005. "Role of mitochondrial ribosome-dependent translation in germline formation in Drosophila embryos." Mechanisms of Development. 122:1087-1093.
An, J.H. et al. 2005. "Regulation of the Caenorhabditis elegans oxidative stress defense protein SKN-1 by glycogen synthase kinase-3." PNAS. 102(45):16275-16280.

Arama, E. et al. 2003. "Caspase Activity and a Specific Cytochrome C Are Required for Sperm Differentiation in Drosophila." Developmental Cell. 4:687-697.
Arama, E. et al. 2006. "The two Drosophila cytochrome C proteins can function in both respiration and caspase activation." The EMBO Journal. 25(1):232-243.
Arbeitman, M.N. et al. 2002. "Gene Expression During the Life Cycle of Drosophila melanogaster." Science. 297:2270-2275.
Ayyadevara, S. et al. 2003. "Genetic Loci Modulating Fitness and Life Span in Caenorhabditis elegans: Categorical Trait Interval Mapping in CL2a×Bergerac-BO Recombinant-Inbred Worms." Genetics Society of America. 163:557-570.
Baehrecke, E.H. 2002. "How Death Shapes Life During Development." Nature Reviews/Molecular Cell Biology. 3:779-787.
Baehrecke, E.H. 2003. "Autophagic programmed cell death in Drosophila." Cell and death Differentiation. 10:940-945.
Bartke, A. 2005. "Minireview: Role of the Growth Hormone/Insulin-Like Growth Factor System in Mammalian Aging." Endocrinology. 146(9):3718-3723.
Bartke, A. et al. 2004. "Life extension in the dwarf mouse." Cur. Top. Dev. Biol. 63:189-225.
Bauer, J.H. et al. 2005. "Neuronal Expression of p53 Dominant-Negative Proteins in Adult Drosophila melanogaster Extends Life Span." Current Biology. 15:2063-2068.
Bazinet, C. et al. 2003. "Rickettsia-like mitochondrial motility in Drosophila spermiogenesis." Evolution & Development. 5(4):379-385.
Bazinet, C. 2004. "Endosymbiotic origins of sex." BioEssays. 26:558-566.
Bhadra, M.P. et al. 2005. "Gene Expression Analysis of the Function of the Male-Specific Lethal Complex in Drosophila." Genetics. 169:2061-2074.
Birchler, J.A. et al. 2003. "Dosage dependent gene regulation and the compensation of the X chromosome in Drosophila males." Genetica. 171:179-190.
Brookes, P.S. 2005. "Mitochondrial H+ leak and ROS generation: An odd couple." Free Radical Biology & Medicine. 38:12-23.
Burger, J.M. et al. 2004. "Sex-specific effects of interventions that extend fly life span." Sci. Aging Knowl. Environ. 2004(28):1-14.
Busuttil, R.A. et al. 2003. "Oxygen accelerates the accumulation of mutations during the senescence and immortalization of mutations during the senescence and immortalization of murine cells in culture." Aging Cell. 2:287-294.
Buszczak, M. et al. 2000. "Eggs to die for: cell death during Drosophila oogenesis." Cell Death and Differentiation. 7:1071-1074.
Carrel, L. et al. 2005. "X-inactivation profile reveals extensive variability in X-linked gene expression in females." Nature. 434:400-404.
Cashio, P. et al. 2005. "Genetic control of programmed cell death in Drosophila melanogaster." Seminars in Cell & Developmental Biology. 16:225-235.
Charlesworth, D. et al. 2005. "Sex Chromosomes: Evolution of the Weird and Wonderful." Current Biology. 15(4):R129-R131.
Chippindale, A.K. et al. 2001. Negative genetic correlation for adult fitness between sexes reveals ontogenetic conflict in Drosophila. 98(4):1671-1675.
Chow, J.C. et al. 2005. "Silencing of the Mammalian X Chromosome." Annu.; Rev. Genomics Hum. Genet. 6:69-91.

(Continued)

Primary Examiner — James Martinell
(74) Attorney, Agent, or Firm — DLA Piper LLP (US)

(57) ABSTRACT

The invention provides anti-apoptotic agents and therapies and uses thereof. Specifically, the anti-apoptotic agents and therapies involve human Xist gene, Xist RNA, Xist gene product, and antagonists and small molecule mimics of these nucleic acids and proteins.

3 Claims, 34 Drawing Sheets

(56) References Cited

OTHER PUBLICATIONS

Clancy, D.J. et al. 2001. "Extension of Life-Span by Loss of CHICO, a *Drosophila* Insulin Receptor Substrate Protein." Science. 229:104-106.
Corona, M. et al. 2005. "Gene expression patterns associated with queen honey bee longevity." Mechanisms of Ageing and Development. 126:1230-1238.
Cox, R.T. et al. 2003. "A Balbiani body and the fusome mediate mitochondrial inheritance during *Drosophila* oogenesis." Development. 130:1579-1590.
Cypser, J.R. et al. 2003. "Hormesis in *Caenorhabditis elegans* dauer-defective mutants." Biogerontology. 4:203-214.
DeLuca, M. et al. 2003. "Dope decarboxylase (Ddc) affects variation in *Drosophila* longevity." Nature Genetics. 34(4):429-433.
Dillin, A. et al. 2002. "Rates of Behavior and Aging Specified by Mitochondrial Function During Development." Science. 298:2398-2401.
Drummond-Barbosa, D. et al. 2001. "Stem cells and their progeny respond to nutritional changes during *Drosophila* oogenesis." Dev. Biol. 231:265-278.
Drysdale, R.A. et al. 2005. "FlyBase: genes and gene models." Nucleic Acids Research. 33:D390-D395.
Fabrizio, J.J. et al. 1998. "Genetic dissection of sperm individualization in *Drosophila melanogaster*." Development. 125:1833-1843.
Finch, C.E. et al. 1999. "The evolution of Alzheimer disease, the reproductive schedule, and apoE isoforms." Neurobiology of Aging. 20:407-428.
Flatt, T. et al. 2005. "Hormonal pleiotropy and the juvenile hormone regulation of *Drosophila* development and life history." BioEssays. 27:999-1010.
Ford, D. et al. 2007. "Alteration of *Drosophila* life span using conditional tissue-specific expression of transgenes triggered by doxycyline or RU 486/Mifepristone." Exp. Gerontol. , pp. 1-15.
Ford, D. et al. 2006. Genetic manipulation of life span in *Drosophila melanogaster*. Handbook of the Biology of Aging. pp. 400-412.
Fridovich, I. 2004. "Mitochondria: are they the sear of senescence?" Aging Cell. 3:13-16.
Fry, A.J. et al. 2002. "*Wolbachia* Interactions That Determine *Drosophila melanogaster* Survival." Evolution. 56(10):1976-1981.
Fry, A.J. et al. 2004. "Variable fitness effects of *Wolbachia* infection in *Drosophila melanogaster*." Heredity. 93:379-389.
Garigan, D. et al. 2002. "Genetic Analysis of Tissue Aging in *Caenorhabditis elegans*: A Role for Heat-Shock Factor and Bacterial Proliferation." Genetics. 161:1101-1112.
Gaspari, L. et al. 2003. "Metabolic gene polymorphisms and p53 mutations in healthy centenarians and younger controls." Biomarkers. 8:522-528.
Gatza, C. et al. 2006. "p53 and Mouse Aging Models." Handbook of the Biology of Aging, Sixth Edition. Chapter 6, pp. 149-171.
Gems, D. et al. 2005. "Broad spectrum detoxification: the major longevity assurance process regulated by insulin/IGF-1 signaling?" Mechanisms of Ageing and Development. 126:381-387.
Gerdes, K. et al. 2005. "Prokaryotic Toxin-Antitoxin Stress Response LOCI." Microbiology. 3:371-382.
Gibson, J.R. et al. 2001. "The X chromosome is a hot spot for sexually antagonistic fitness variation." The Royal Society. 269:499-505.
Good, J.M. et al. 2005. "Rates of Protein Evolution Are Positively Correlated with Developmental Timing of Expression During Mouse Spermatogenesis." Molecular Biology and Evolution. 22(4):1044-1052.
Graham, P. et al. 2002. "Masters change, slaves remain." BioEssays. 25:1-4.
Graves, J.A.M. 2006. "Sex Chromosome Specialization and Degeneration in Mammals." Cell. 124:901-914.
Gray, M.W. et al. 1999. "Mitochondrial Evolution." Science. 283:1476-1481.
Hekimi, S. et al. 2003. "Genetics and the Specificity of the Aging Process." Science. 299:1351-1354.
Helfand, S.L. et al. 2003. "Genetics of Aging in the Fruit Fly, *Drosophila melanogaster*." Annu.Rev.Genet. 37:329-348.
Herndon, L.A. et al. 2002 "Stochastic and genetic factors influence tissue-specific decline in ageing *C. elegans*." Nature. 419:808-814.
Hogeweg, P. et al. 2003. "Multilevel Selection in Models of Prebiotic Evolution: Compartments and Spatial Self-Organization." 33:375-403.
Honda, Y. et al. 1999. "The daf-2 gene network for longevity regulates oxidative stress resistance and Mn-superoxide dismutase gene expression in *Caenorhabditis elegans*." The FASEB Journal. 13:1385-1393.
Hsu, H. et al. 2005. "Genetic regulation of thymic involution." Mechanisms of Ageing and Development. 126:87-97.
Hughes, K.A. et al. 2005. "Evolutionary and Mechanistic Theories of Aging." Annu. Rev. Entomol. 50:421-445.
Hussein, M.R. 2005. "Apoptosis in the ovary: molecular mechanisms." Human Reproduction Update. 11(2):162-178.
Hwangbo, D.S. et al. 2004. "*Drosophila* dFOXO controls lifespan and regulates insulin signaling in brain and fat body." Nature. 429:562-566.
Jackson, A.U. et al. 2002. "Mouse Loci Associated With Life Span Exhibit Sex-Specific and Epistatic Effects," Journal of Gerontology: Biological Sciences. 57A(1):B9-B15.
Jones, A. 2000. "Does the plant mitochondrion integrate cellular stress and regulate programmed cell death?" Trends Plant Sci. 5:225-30.
Kenyon, C. 2005. "The Plasticity of Aging: Insights from Long-Lived Mutants." Cell. 120:449-460.
Kirkwood, T.B. et al. 2000. "Why do we age?" Nature. 408:233-238.
Kloc, M. et al. 2004. "The Balbiani body and germ cell determinants: 150 years later." Curr. Top. Dev. Biol. 50:1-36.
Kobayashi, S. et al. 2005. The Role of Mitochondrial rRNAs and Nanos Protein in Germline Formation in *Drosophila* Embryos. 22:943-954.
Kraukauer, D.C. et al. 1999. "Mitochondria and germ-cell death." Nature. 400:125-126.
Kujoth, G.C. et al. 2005. "Mitochondrial DNA Mutations, Oxidative Stress, and Apoptosis in Mammalian Aging." Science. 309:481-484.
Landis, G.N. et al. 2003. "A search for doxycycline-dependent mutations that increase *Drosophila melanogaster* life span identifies the VhaSFD, Sugar baby, filamin, fwd and Cct 1 genes." Genome Biology. 4(2):R8-R8.14.
Landis, G.N. et al. 2004. "Superoxide dismutase evolution and life span regulation." Mechanisms of Ageing and Development. pp. 1-15.
Lang, B.F. et al. 1999. "Mitochondrial Genome Evolution and the Origin of Eukaryotes." Annual Review of Genetics. 33:351-397.
Larsen, P.L. 1993. "Aging and resistance to oxidative damage in *Caenorhabditis elegans*." Proc. Natl. Acad. Sci. USA 90. 90:8905-8909.
Lee, S.S. et al. 2003. "DAF-16 Target Genes That Control *C. elegans* Life-Span and Metabolism." Science. 300:644-647.
Lee, S.S. et al. 2002. "A systematic RNAi screen identifies a critical role for mitochondria in *C. elegans* longevity." Nature genetics 33:40-48.
Leips, J. et al. 2006. "Quantitative Trait Loci With Age-Specific Effects on Fecundity in *Drosphila melanogaster*." Genetics Society of America. 172:1595-1605.
Leips, J. et al. 2000. "Quantitative Trait Loci for Life Span in *Drosophila melanogaster*: Interactions With Genetic Background and Larval density." Genetics. 155:1773-1788.
Line, M.A. 2005. "A Hypothetical Pathway From the RNA to the DNA World." Origins of Life and Evolution of Biospheres. 35:395-400.
Luckinbill, L.S. et al. 1984. "Selection for Delayed Senescence in *Drosophila melanogaster*." Evolution. 38(5):996-1003.
Mackey, T.F.C. 2002. "The nature of quantitative genetic variation for *Drosophila* longevity." Mechanisms of Ageing and Development. 123:95-104.
Magwere, T. et al. 2004. "Sex Differences in the Effect of Dietary Restriction on Life Span and Mortality Rates in Female and Male *Drosophila melanogaster*." Journal of Gerontology:Biological Sciences. 59A(1):3-9.

(56) References Cited

OTHER PUBLICATIONS

Maier, B. et al. 2004. "Modulation of mammalian life span by the short isoform of p53." Genes Dev. 18:306-319.

Mair, W. et al. 2003. "Demography of dietary restriction and death in *Drosophila*." Science. 301:1731-1733.

Martin, G.M. 2005. "Genetic modulation of senescent phenotypes in *Homo sapiens*." Cell. 120:523-532.

Masoro, E.J. 2005. "Overview of coloric restriction and ageing." Mech. Ageing Dev. 126:913-22.

McCulloch, D. et al. 2003. "Evolution of male longevity bias in nematodes." Aging Cell. 2:165-173.

Miller, P.M. et al. 2006. "Sexual conflict via maternal-effect genes in ZW species." Science. 312:73.

Miller, R.A. 2005. "Genetic approaches to the study of aging." J. Am. Geriatric Soc. 53:S284-S286.

Murphy, C.T. et al. 2003. "Genes that act downstream of DAF-16 to influence the lifespan of *Caenorhabditis elegans*." Nature. 424:277-284.

Nielsen, R. et al. 2005. "A scan for positively selected genes in the genomes of humans and chimpanzees." PLoS Biology. 3(6):0976-0985.

Nilsen, J. et al. 2004. "Mitochondria as Therapeutic Targets of Estrogen Action in the Central Nervous System." Current Drug Targets—CNS & Neurological Disorders. 3:297-313.

Nishimura, Y. et al. 2006. "Active digestion of sperm mitochondrial DNA in single living sperm revealed by optical tweezers." PNAS. U.S.A. 103(5):1382-1387.

Nowak, M.A. et al. 2004. "Evolutionary dynamics of biological games." Science. 303:793-799.

Nuzhdin, S.V. et al. 2005. "Survival Analysis of life span quantitative trait loci in *Drosophila melanogaster*." Genetics. 170:719-731.

Nuzhdin, S.V. et al. 1997. "Sex-specific quantitative trait loci affecting longevity in *Drosophila melanogaster*." Proc. Natl. Acad. Sci. USA. 94:9734-9739.

Ohki, R. et al. 2001. "In Vitro Reconstitution of the End Replication Problem." Molecular and Cellular Biology. 21(17):5753-5766.

Oliver, B. et al. 2004. "Battle of the Xs." Bioessays. 26:543-548.

Olovnikov, A.M. 1973. "A theory of marginotomy. The incomplete copying of template margin in enzymic synthesis of polynucleotides and biological significance of the phenomenon." J. Theor. Biol. 41:181-190.

Parisi, M. et al. 2004. "A survey of ovary-testis-, and soma-biased gene expression in *Drosophila melanogaster* adults." Genome Biol. 5:R40.

Parisi, M. et al. 2003. "Paucity of genes on the *Drosophila* X chromosome allowing malebiased expression." Science. 299:697-700.

Parkes, T.L. et al. 1998. "Extension of *Drosophila* lifespan by overexpression of human SOD1 in motorneurons." Nature Genet. 19;171-174.

Partridge, L. et al. 2005. "Dietary restriction, mortality trajectories, risk and damage." Mech. Ageing Dev. 126:35-41.

Pepling, M.E. et al. 2001. "Mouse ovarian germ cell cysts undergo programmed breakdown to form primordial follicles." Dev. Biol. 234:339-351.

Perls. T. et al. 2003. "Genetics of exceptional longevity." Exp. Gerontol. 38:725-730.

Rand, D.M. 2005. "Mitochondrial Genetics of Aging: Intergenomic Conflict Resolution." Sci. Aging Knowledge Environ. re5. pp. 1-7.

Rand, D.M. et al. 2001. "Sexually antagonistic cytonuclear fitness interactions in *Drosophila melanogaster*." Genetics. 159:173-187.

Rand, D.M. et al. 2006. "Nuclear-mitochondrial epistasis and *Drosophila* aging: introgression of *Drosophila simulans* mtDNA modifies longevity in *D. melanogaster* nuclear backgrounds." Genetics. 172:329-341.

Rauser, C.L. et al. 2006. "Evolution of late-life fecundity in *Drosophila melanogaster*." J. Evol. Biol. 19:289-301.

Reiwitch, S.G. et al. 2002. "Quantitative trait loci for lifespan of mated *Drosophila melanogaster* affect both sexes." Genet. Res. 80:225-230.

Rice, W.R. 1992. "Sexually antagonistic genes: experimental evidence." Science. 256:1436-1439.

Rice, W.R. 1998. Male fitness increases when females are eliminated from gene pool: implications for the Y chromosome. Proc. Natl. Acad. Sci. USA. 95:6217-6221.

Richards, S. et al. 2005. "Comparative genome sequencing of *Drosophila pseudoobscura*: chromosomal, gene, and cis-element evolution." Genome Res. 15:1-18.

Rose, M.R. 1984. "Laboratory evolution of postponed senescence in *Drosophila melanogaster*." Evolution. 38:1004-1010.

Scheuring, I. et al. 2003. "Spatial models of prebiotic evolution: soup before pizza?" Orig. Life Evol. Biosph. 33:319-355.

Searcy, D.G. 2003. "Metabolic integration during the evolutionary origin of mitochondria." Cell Res. 13:229-238.

Spees, J.L. et al. 2006. "Mitochondrial transfer between cells can rescue aerobic respiration." Proc. Natl. Acad. Sci. U.S.A. 103(5):1283-1288.

Spencer, C.C. et al. 2003. "Testing on 'aging gene' in long-lived *Drosophila* strains: increased longevity depends on sex and genetic background." Aging Cell. 2:123-130.

Starr, D.J. et al. 2002. "A host parasite interaction rescues *Drosophila* oogenesis defects." Nature. 418:76-79.

Stewart, E.J. et al. 2005. "Aging and death in an organism that reproduces by morphologically symmetric division." PLoS Biology. 3(2):0295-0300.

Sun, J. et al. 2002. "Induced overexpression of mitochondrial Mn-superoxide dismutase extends the life span of adult *Drosophila rnelanogaster*." Genetics. 161:661-672.

Sun, J. et al. 1999. "FLP recombinase-mediated induction of Cu/Zn-superoxide dismutase transgene expression can extend the life span of adult *Drosophila melanogaster* flies." Mol. Cell Biol. 19:216-228.

Szathmary, E. 2000. "The evolution of replicators." Philos. Trans. R. Soc. Lond. B:Biol. Sci. 355:1669-1676.

Tatar, M. et al. 1997. "Chaperoning extended life." Nature. 390:30.

Tatar, M. et al. 2001. "A mutant *Drosophila* insulin receptor homolog that extends life-span and impairs neuroendocrine function." Science. 292:107-110.

Timmis, J.N. et al. 2004. "Endosymbiotic transfer: organelle genomes forge eukaryotic chromosomes." Nat. Rev. Genet. 5:123-135.

Tyner, S.D. et al. 2002. "p53 mutant mice that display early ageing associated phenotypes." Nature. 415:45-53.

Valenzuela, R.K. et al. 2004. "Quantitative trait loci affecting life span in replicated populations of *Drosophila melanogaster*, II. Response to Selection." Genetics. 168:313-324.

Van Heemst, D. et al. 2005. "Variation in the human TP53 gene affects old age survival and cancer mortality." Exp. Gerontol. 40:11-15.

Vieira, C. et al. 2000. "Genotype-Environment Interaction for Quantitative Trait Loci Affecting Life Span in *Drosophila melanogaster*." Genetics. 154:213-227.

Vina, J. et al. 2005. "Why females live longer than males: control of longevity by sex hormones." Sci. Aging Knowledge Environ. pe 17. pp. 1-7.

Walker, G.A. et al. 2001. "Heat Shock Protein Accumulation Is Unregulated in a Long-Lived Mutant of *Caenorhabditis elegans*." Journal of Gerontology: Biological Sciences. 56A(7):B2381-B287.

Wallace, D.C. 2005. "A Mitochondrial Paradigm of Metabolic and Degenerative Diseases, Aging, and Cancer: A Dawn for Evolutionary Medicine." Annu. Rev. Genet. 39:359-407.

Walter, R. et al. 1998. "T-Kininogen is a biomarker of senescence in rats." Mech. Ageing Dev. 106:129-144.

Wang, M.H. et al. 2004. "Environment-dependent survival of *Drosophila melanogaster*: a quantitative genetic analysis." Aging Cell. 3:133-140.

Wilk, K. et al. 2004. "Delivery of germinal granules and localized RNAs via the messenger transport organizer pathway to the vegetal cortex of *Xenopus* oocytes occurs through directional expansion of the mitochondrial cloud." Int.J.Dev.Biol. 49:17-21.

Wolfner, M.F. 2002. "The gifts that keep on giving: physiological functions and evolutionary dynamics of male seminal proteins in *Drosophila*." Heredity. 88:85-93.

(56) References Cited

OTHER PUBLICATIONS

Yin, V.P. et al. 2005. "Mechanisms of steroid-triggered programmed cell death in *Drosophila*." Seminars in Cell & Developmental Biology. 16:237-243.

Zheng, J. et al. 2005. "Differential patterns of apoptosis in response to aging in *Drosophila*." Proc.Natl.Acad.Sci. 102(34):12083-12088.
PCT International Search Report mailed Oct. 8, 2008 based on PCT/US2007/013626.

* cited by examiner

Drosophila male
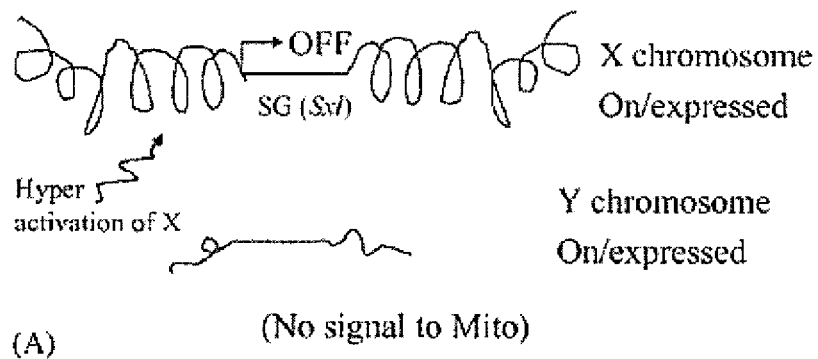
(A) (No signal to Mito)
Drosophila female
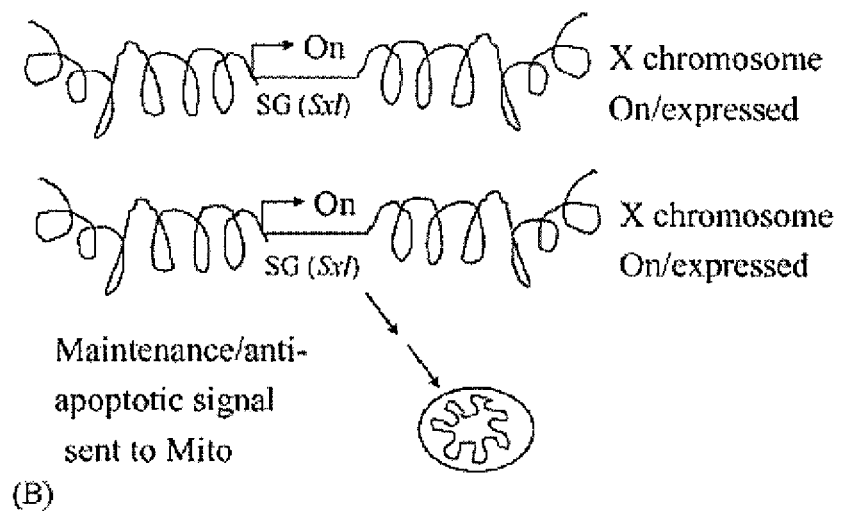
Figure 3

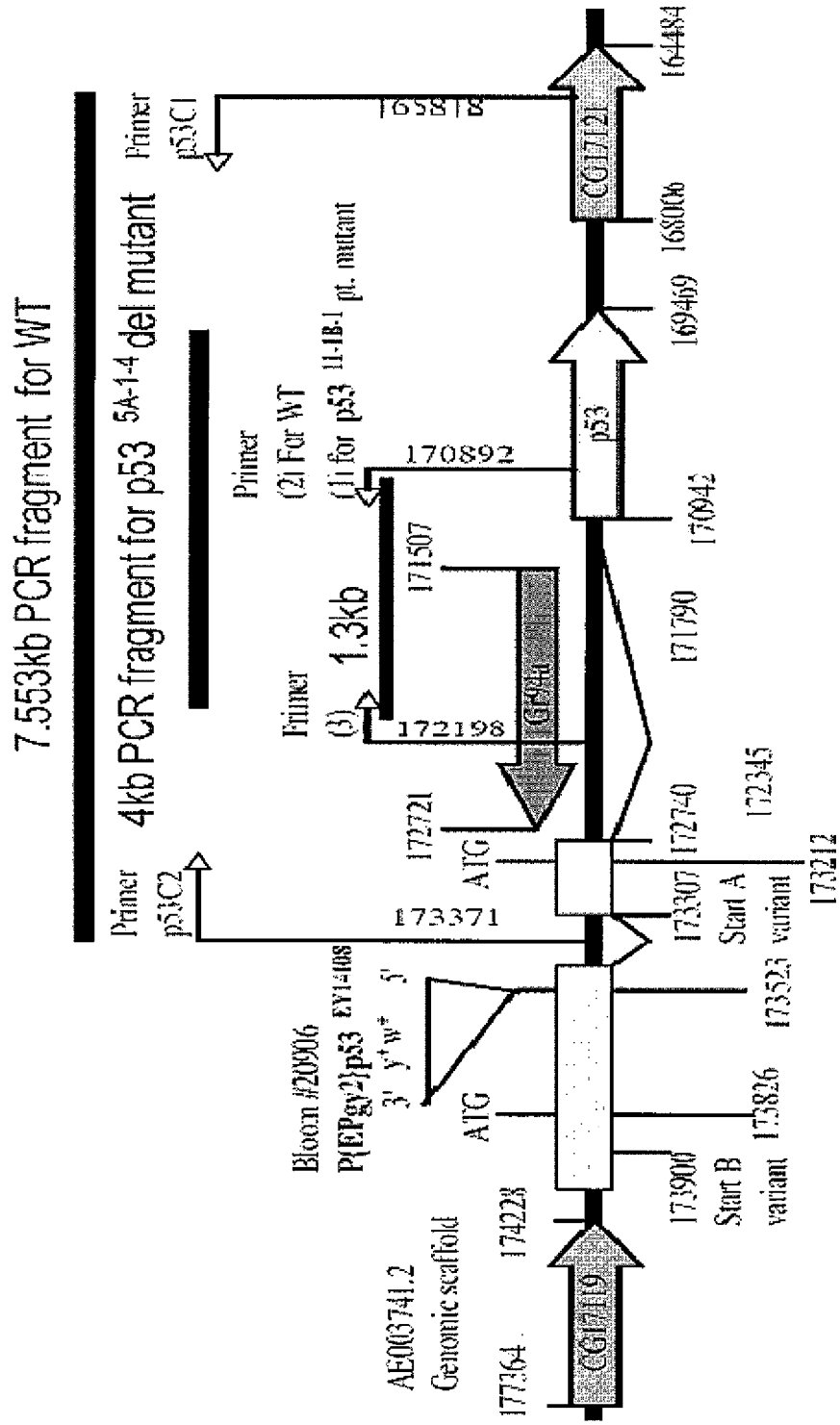
Figure 7B-1 (p53 Map)

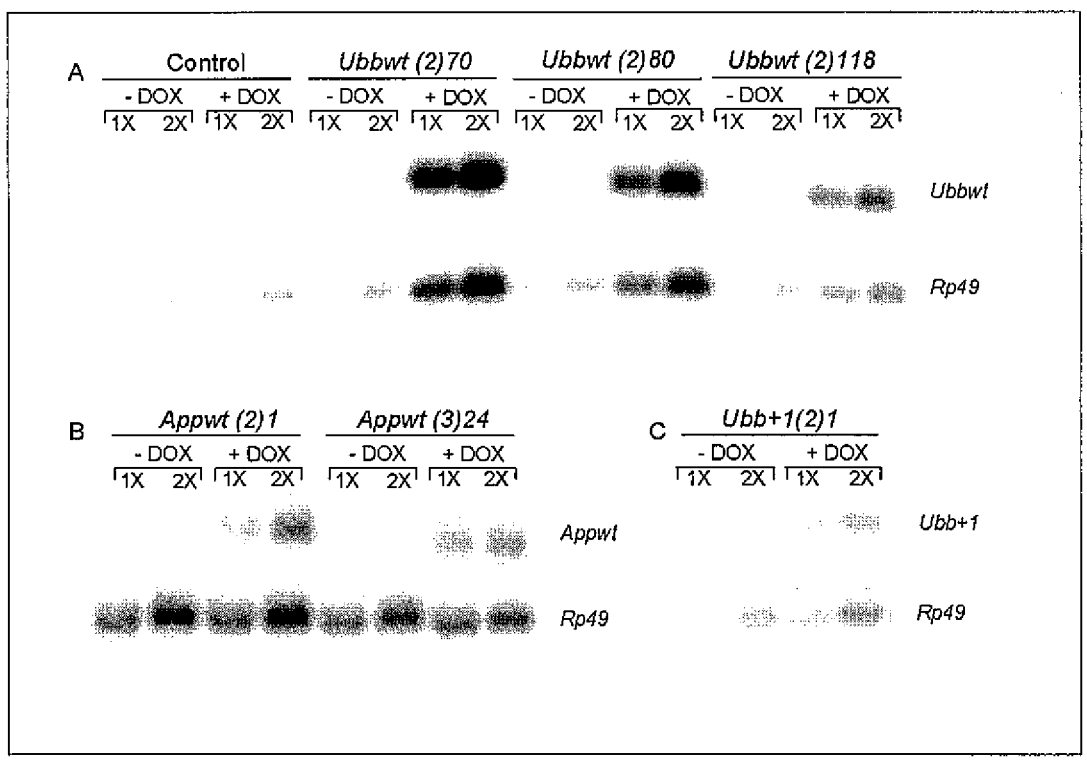
Figure 11 A – C

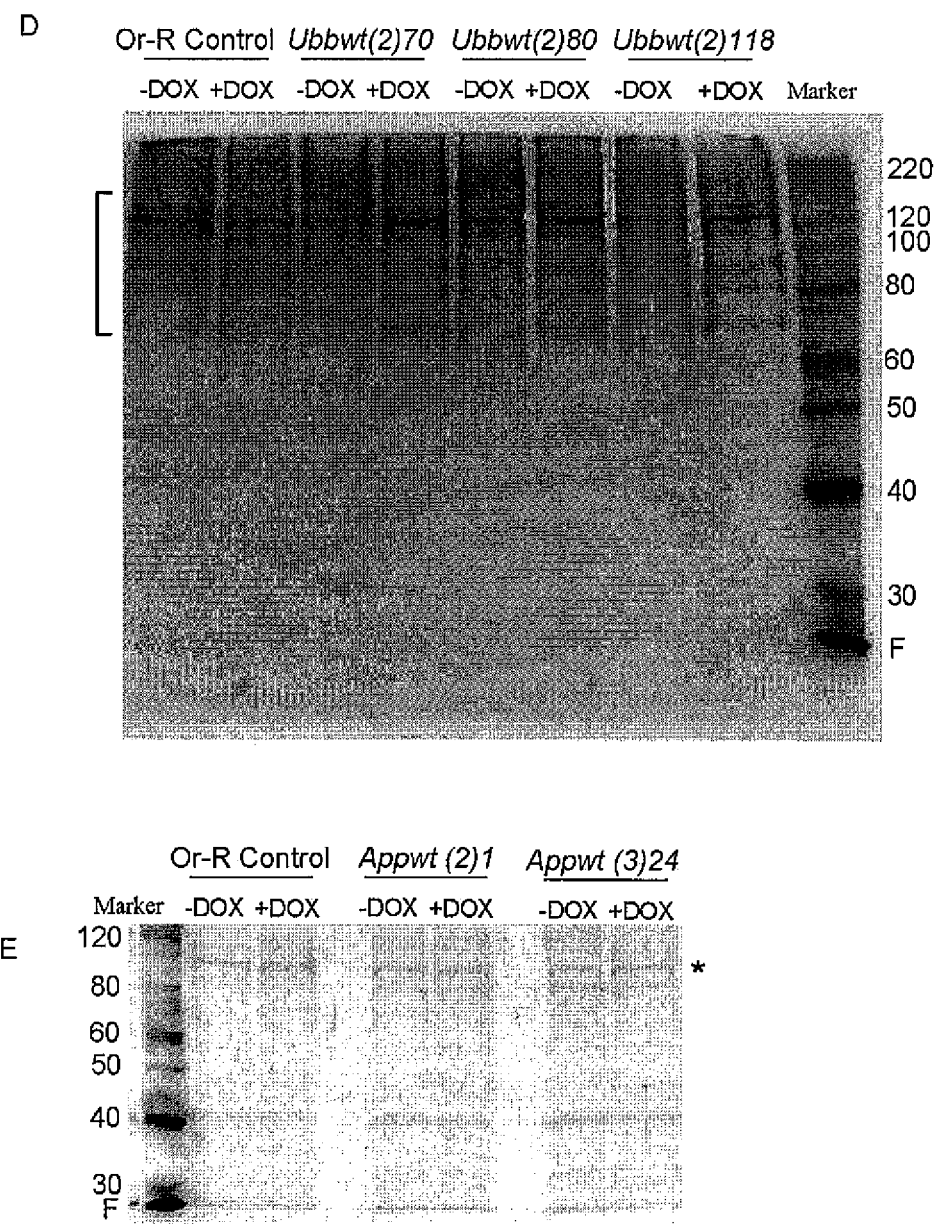
Figure 11 D – E

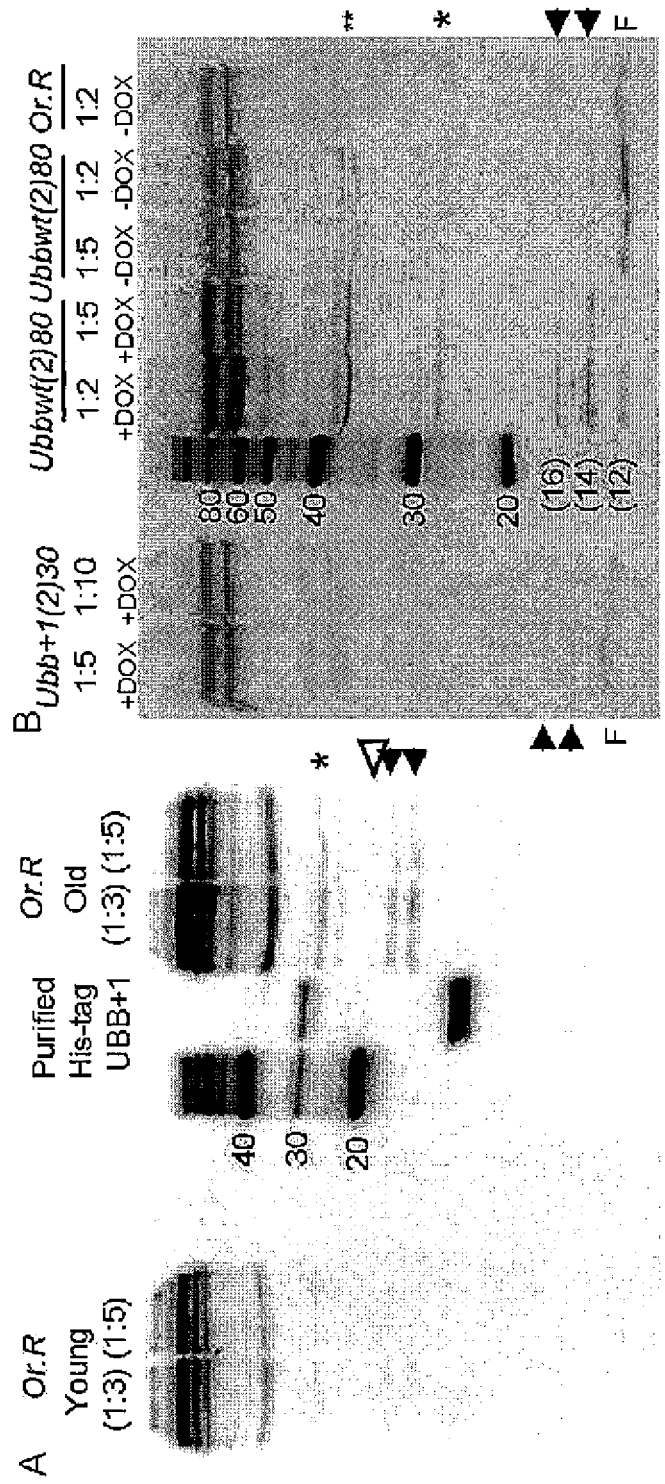
Figure 12 A - B

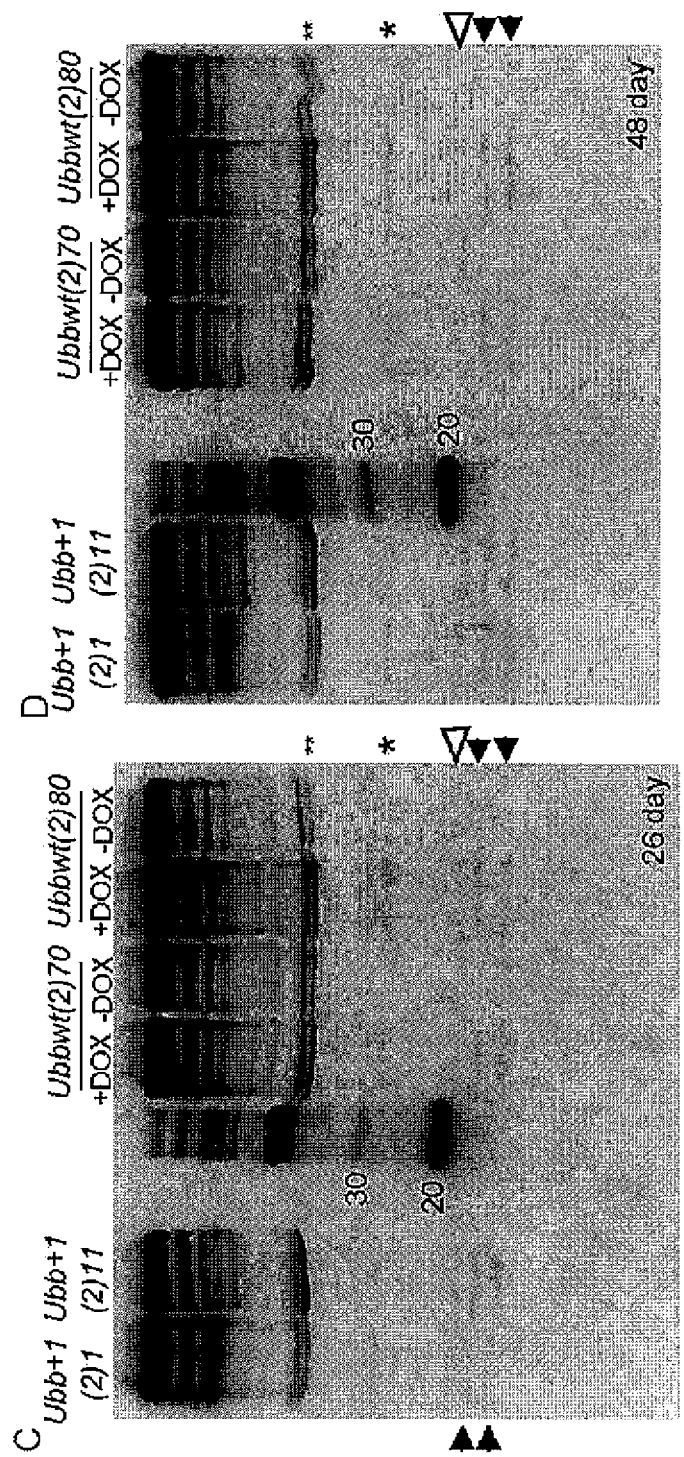
Figure 12 C – D

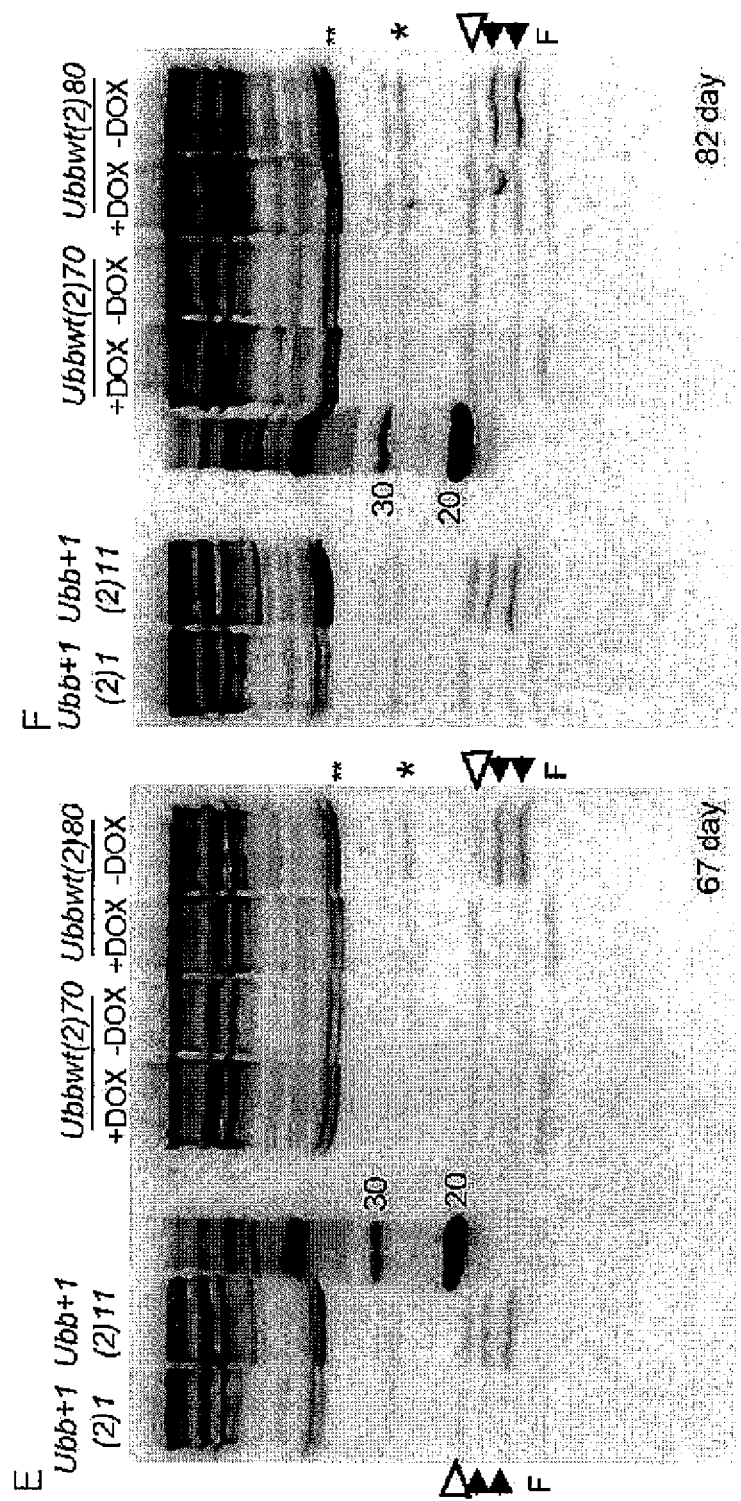
Figure 12 E - F

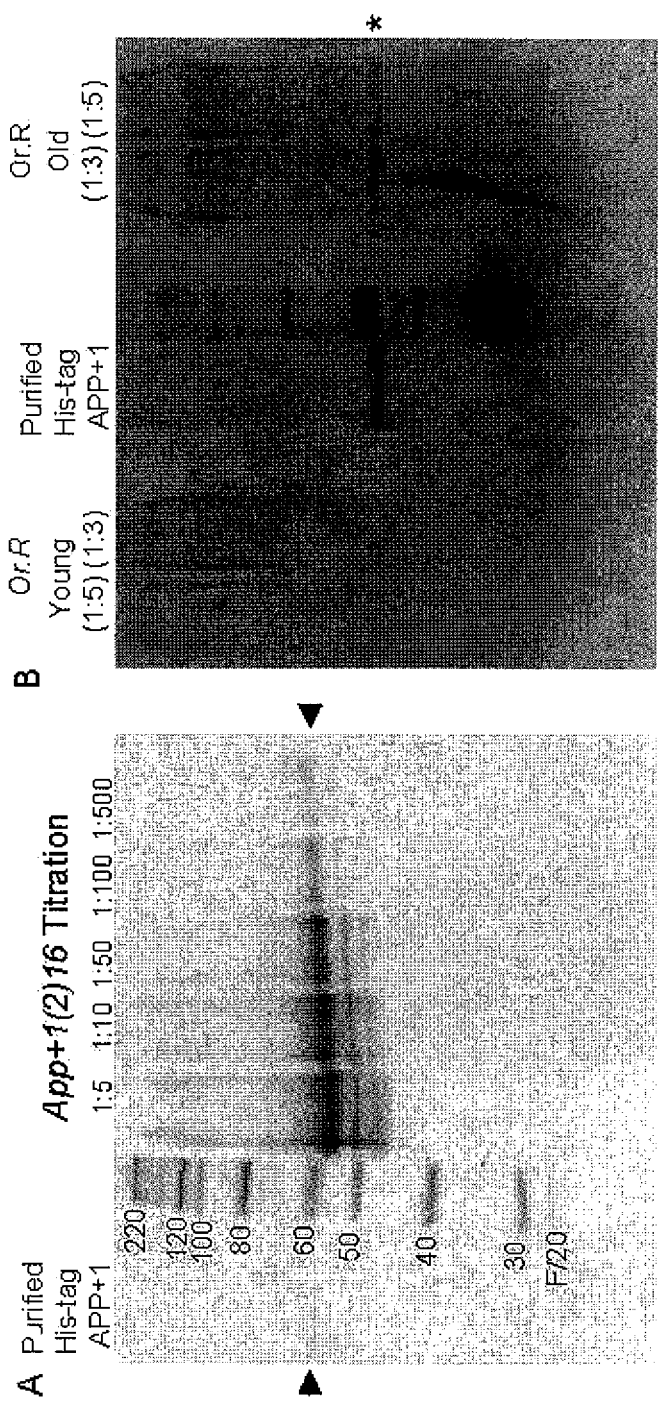
Figure 13 A - B

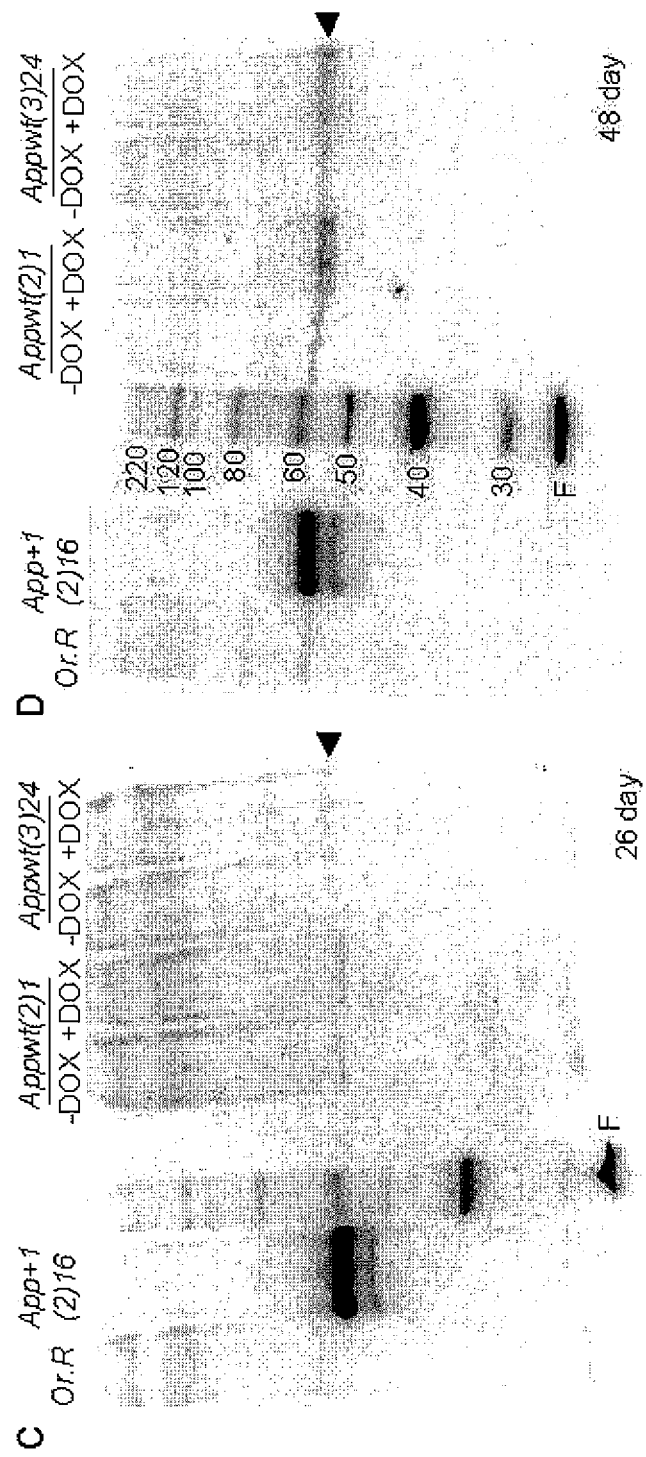
Figure 13 C - D

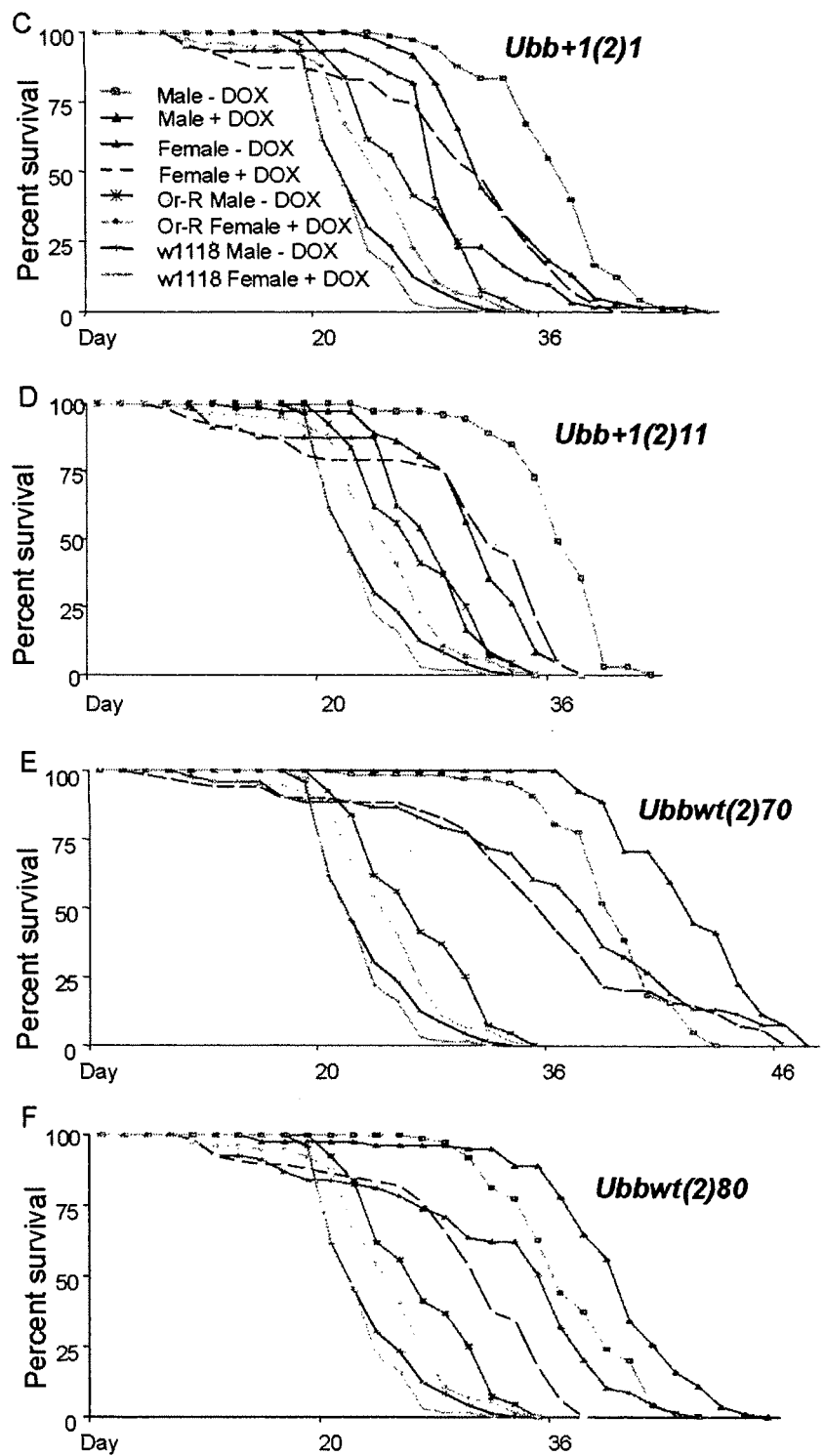
Figure 14 C - F

SEX-SPECIFIC REGULATION OF AGING AND APOPTOSIS

CROSS-REFERENCE TO RELATED APPLICATIONS

This application claims an invention which was disclosed in Provisional Application No. 60/811,899 filed Jun. 7, 2006, entitled "SEX-SPECIFIC REGULATION OF AGING AND APOPTOSIS". The benefit under 35 USC §119(e) of the United States provisional application is hereby claimed. The above priority applications are hereby incorporated herein by reference.

STATEMENT REGARDING FEDERALLY SPONSORED RESEARCH AND DEVELOPMENT

The present invention is made, at least in part, with the support of grants from Department of Health and Human Services (AG11833, AG11644). The government has certain rights in the invention.

SEQUENCE LISTING

The present invention contains sequence listing.

FIELD OF THE INVENTION

The invention pertains to the field of senescence and evolution. More particularly, the invention provides mechanism for sex-specific regulation of aging and apoptosis.

BACKGROUND OF THE INVENTION

Recent and classic observations suggest that the mitochondria has an important and ancient role in determining the distinction between germ-line and soma, as well as sexual identity. In this regard, the fact that the mitochondria genome is asymmetrically inherited is perhaps THE defining feature of the oocyte.

The asymmetric inheritance feature of mitochondrial genes and sex chromosome genes promotes the evolution of sexually antagonistic gene functions (i.e. compromised gene function in one sex or both). The present invention is based on the premises that such genes will contribute preferentially to the aging phenotype.

SUMMARY OF THE INVENTION

Genetic analysis of *Drosophila*, mice and humans indicates that gene alleles, mutations and transgenes that affect life span tend to have different effects in an organism depending on the sex of the organism. The likely reason for this is that the sexes have different genotypes (e.g., X/X vs. X/Y) and face quite different environmental pressures (e.g., to reproduce, males have to mate with females and vice versa, but mate selection criteria for each sex may be very different). That is to say, genes are subject to different genetic interactions and different gene-by-environment effects in males than in females. The consequence is that through evolution certain genes are differentially selected and optimized for one sex over the other. The mitochondrial genome and the X chromosome are such differentially selected genes.

Both the mitochondrial genome and the X chromosome are asymmetrically inherited in *Drosophila* and mammals. Through evolution, the mitochondrial spend relatively more time under selection in females and are therefore expected to be better optimized for function in the female than in the male. This hypothesis is supported by the fact that the *Drosophila* X chromosome is a hotspot for sexually antagonistic fitness variation.

In terms of the aging phenotype, *Drosophila* and mammals females tend to live longer than males. This may be due in part to sub-optimal mitochondrial function in males. One finds evidence for this hypothesis in the observation that old *Drosophila* and old mammals exhibit apoptosis—an observation that is consistent with the idea that mitochondria are less functional during aging due to maternal-only inheritance.

Together, these data support the conclusion that a significant part of the aging phenotype is due to antagonistic pleiotropy of gene function between the sexes.

With these considerations, the inventor of the present has devised a molecular model which describes the co-regulation of sex determination, apoptosis and life span based on the on/off status of a single gene: Sxl in *Drosophila melanogaster* and Xist in humans (exemplary sequence of Sxl is provided in SEQ ID:1-2, and Xist in SEQ ID 3). In accordance with on this model, the present invention provides methods and products for utilizing the of/off mechanism in a subject to effect an aging related change in a subject.

In particular, one object of the present invention is to provide anti-apoptotic agents and therapies involving human Xist gene, Xist RNA, Xist gene product, antagonists of the above-mentioned nucleic acids and proteins, and small molecule mimics of the above-mentioned nucleic acids and proteins. Another object of the present invention is to provide prophylactic anti-aging agents and therapies involving human Xist gene, Xist RNA, Xist gene product, antagonists of the above-mentioned nucleic acids and proteins, and small molecule mimics of the above-mentioned nucleic acids and proteins.

A further object of the invention relates to the use of the finite half-life gene segregation mechanism to produce in vitro evolution of genes and the directed evolution of genes with desired properties.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

dIAP2 mutant mean life span=84.305 days, variance=265.367, Std. Dev.=16.290, St. Err.=1.182. Or-R control #2 mean life span=72.457 days, variance=286.086, Std. Dev.=16.914, St. Err.=1.247. Mean Difference=11.849, unpaired, two-sided t-test P<0.0001, percent change=100*(84.3-72.45)/72.45=+16%.

FIG. 3A and 3B Diagrams of *Drosophila* dosage compensation and sex determination.

Figure 4:
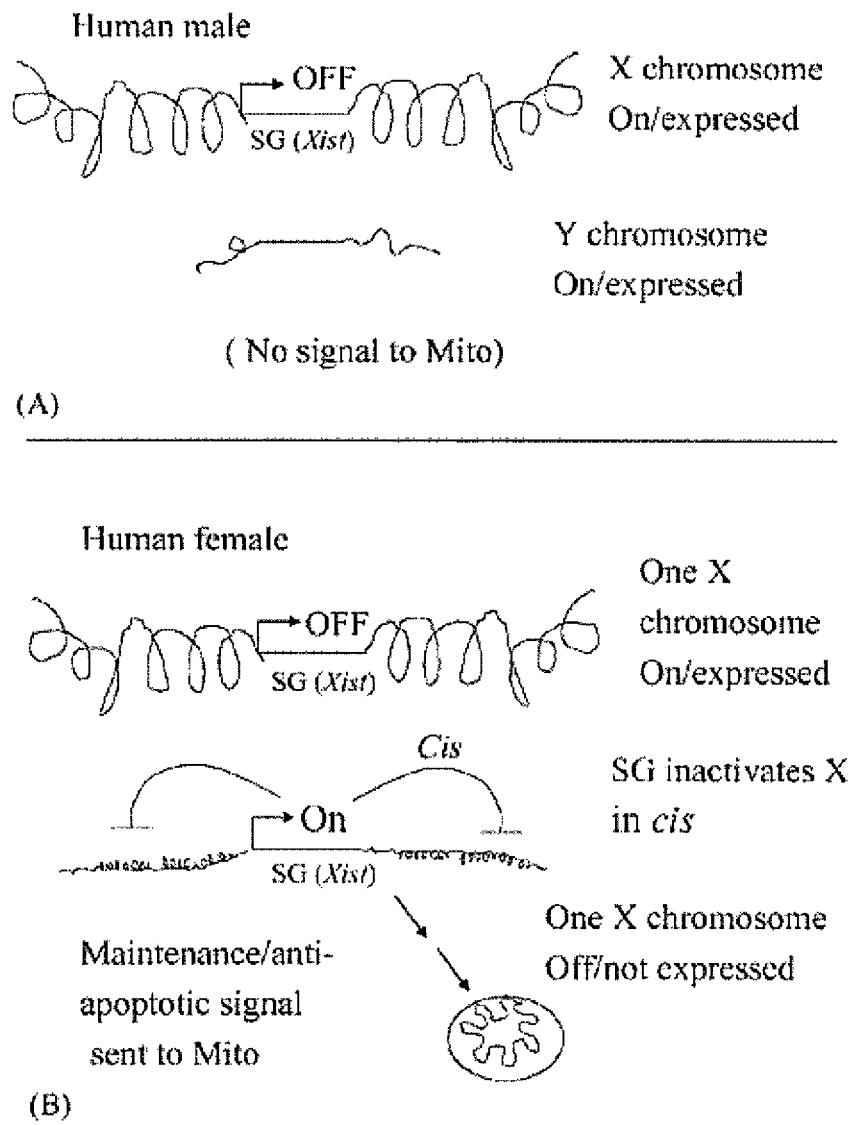

FIG. 4A and 4B Diagrams of human dosage compensation and proposed sex determination.

Figure 5:
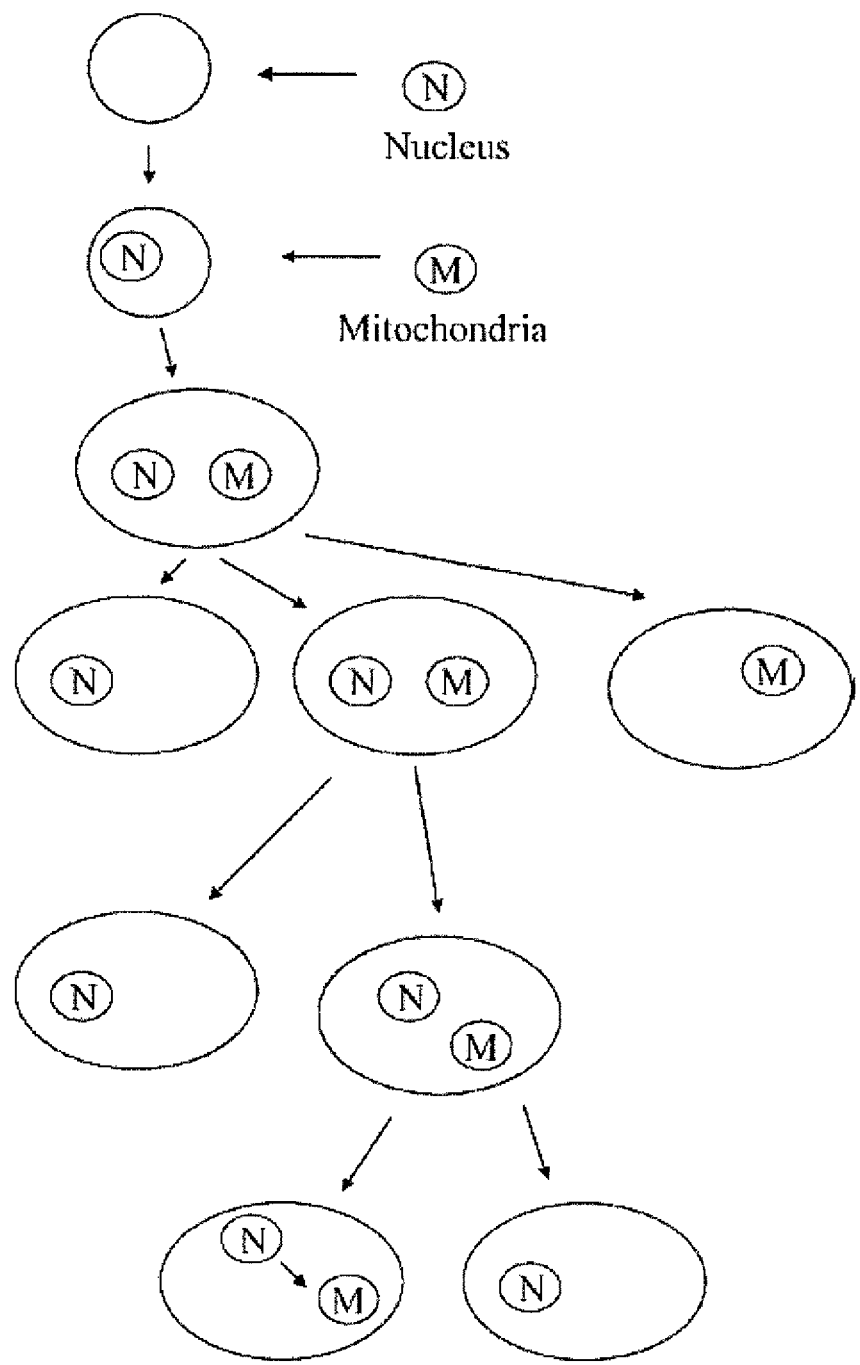

FIG. 5 Invasion of the eukaryotic cell by the mitochondria. When the mitochondria (M) invaded the eukaryotic cell it created competition for inheritance between the mitochondria and the nucleus (N). The only way the M could be maintained is if it provided some advantage to the cell. In turn, the only way M could be maintained as an entity separate from N is to have a finite half life, i.e., be lost at some rate by segregation or apoptosis—this is the same thing as asymmetric segregation. The simplest way to accomplish this is two states in N, one state that prevents M loss, and one that does not.

Figure 6:
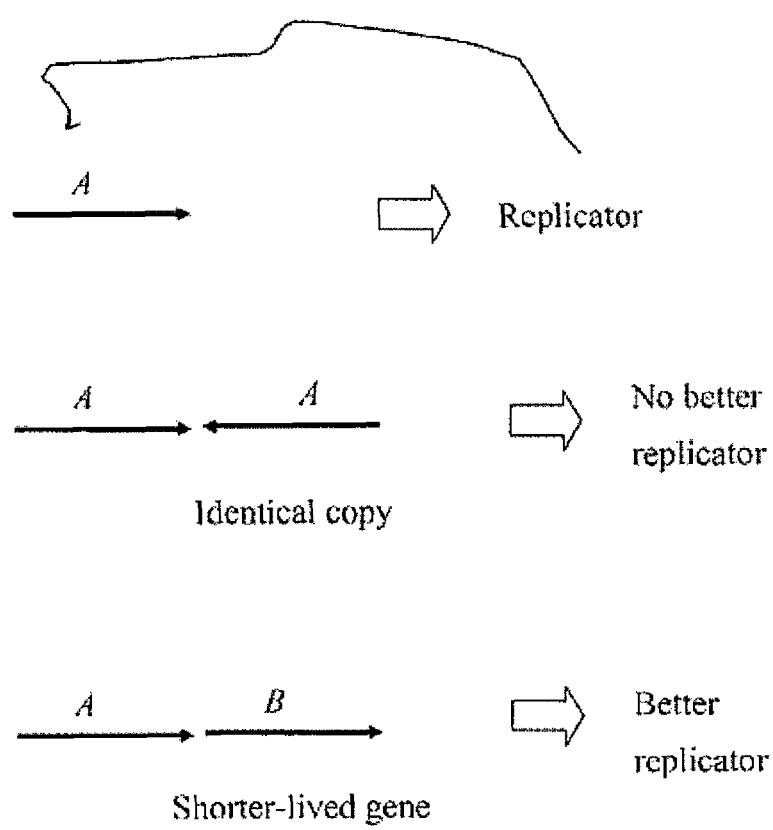

FIG. 6 Genes and replicators. Gene A encodes a single-subunit replicator that replicates gene A. A perfectly identical and symmetric copy of gene A has no selective advantage because it encodes the same replicator (by definition). One way a second gene B (such as an imperfect copy of A) can be maintained as a separate entity is if it has a shorter half-life than A (i.e., is lost at some rate). By definition this creates two states for A: A alone and A+B, which is the same thing as asymmetric segregation. To be maintained A+B must encode a better replicator (i.e., have greater fitness).

Figure 7A:
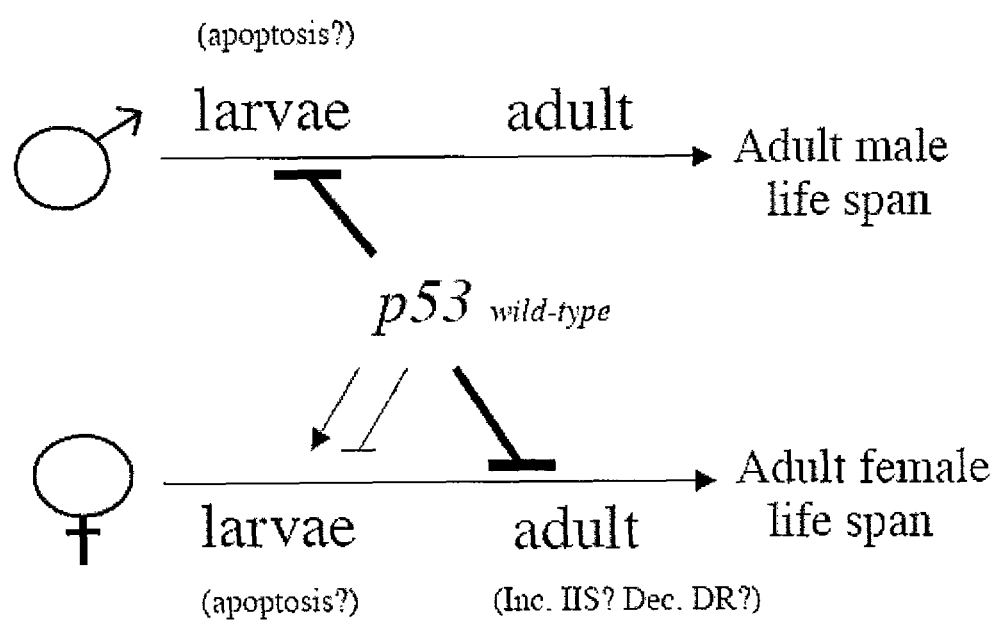
Figures 2, 7B:
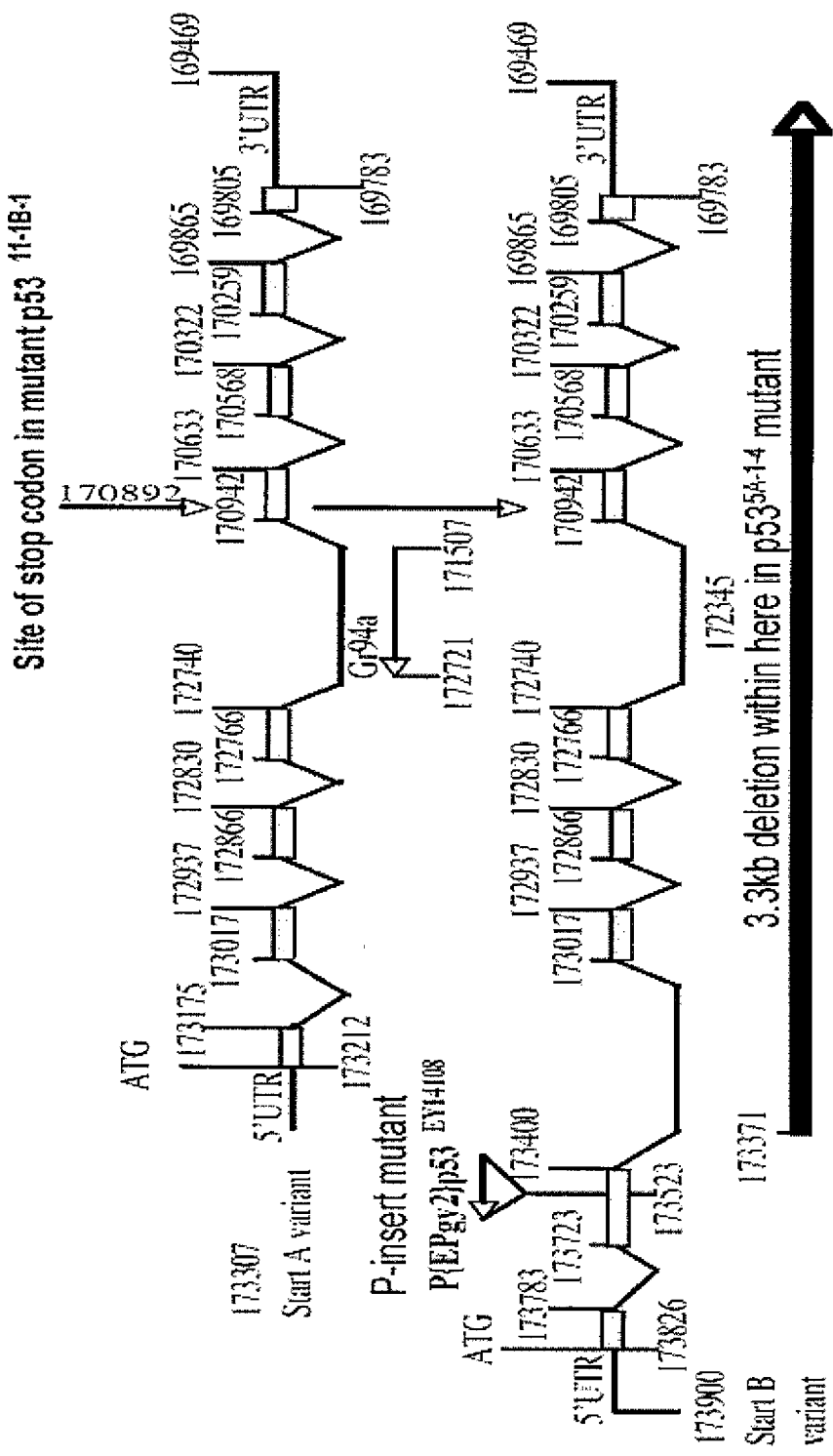

FIG. 7 Summary of *Drosophila* p53 gene and genetic alterations and life span effects. (A) Summary of p53 genetic effects on adult life span. (B1-B3) Diagram of p53 gene mutations and transgenic constructs.

FIG. 8 Effect of p53 mutations on life span. (A). L cohort female survivals. (B). L cohort male survivals. (C). 100% oxygen survival. (D1-D2). Ionizing radiation survival.

Figure 9A:
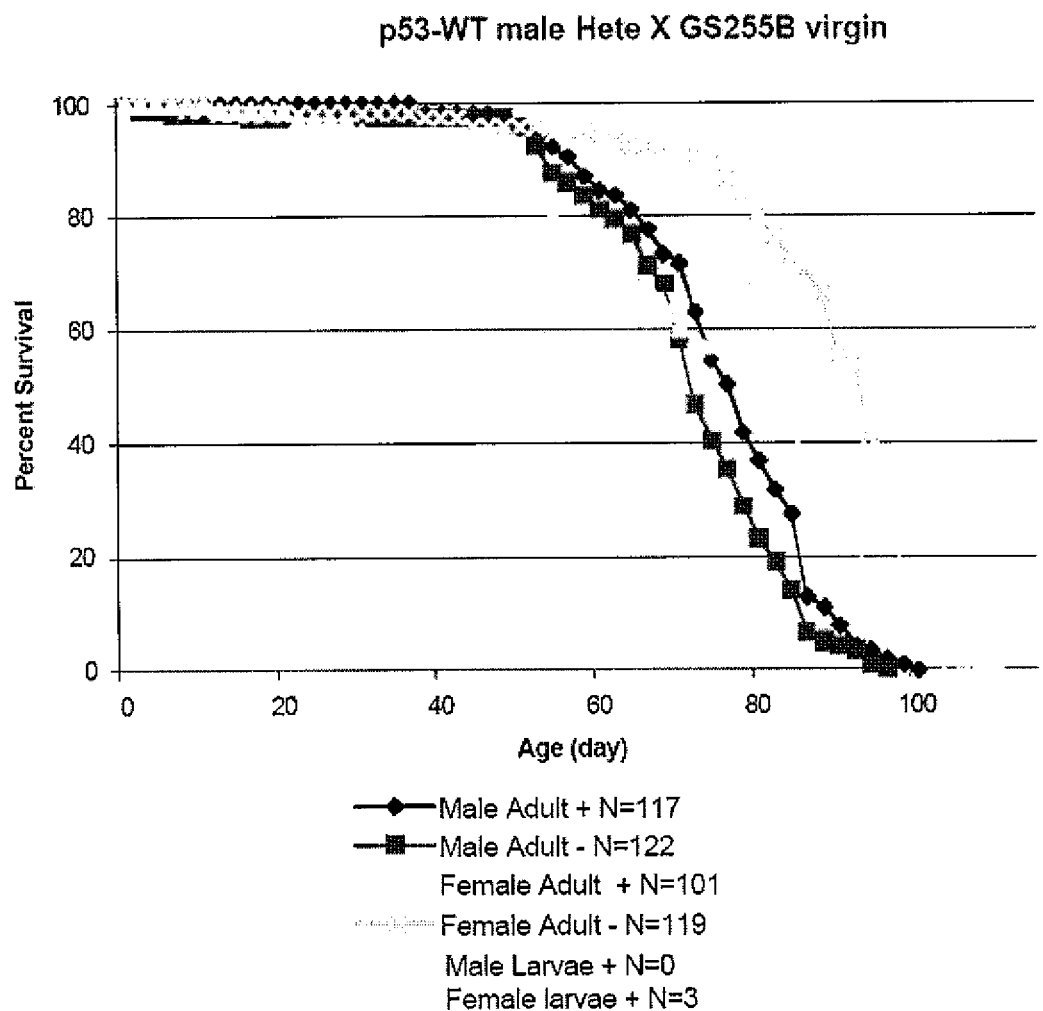
Figure 9B:
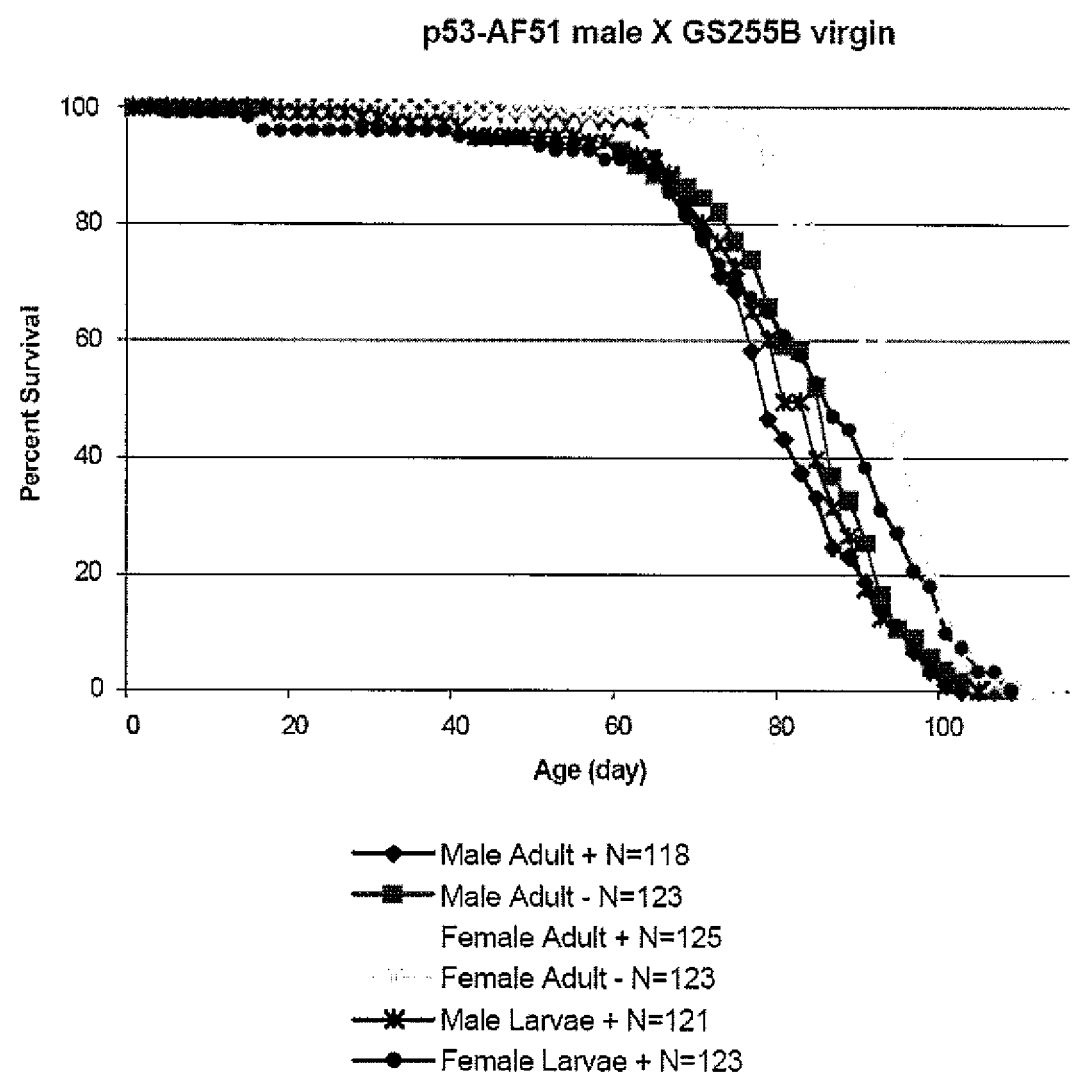
Figure 9C:
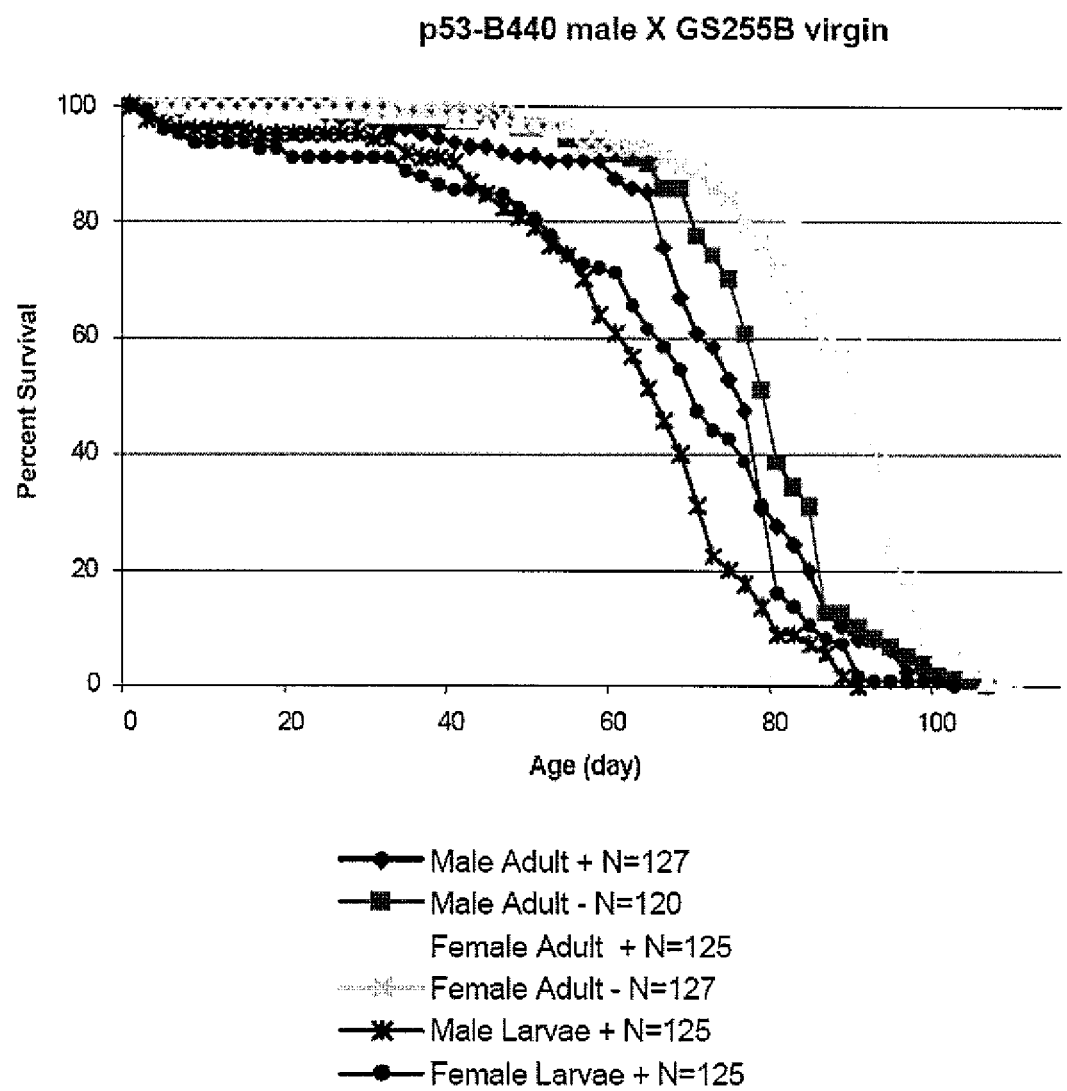
Figure 9D:
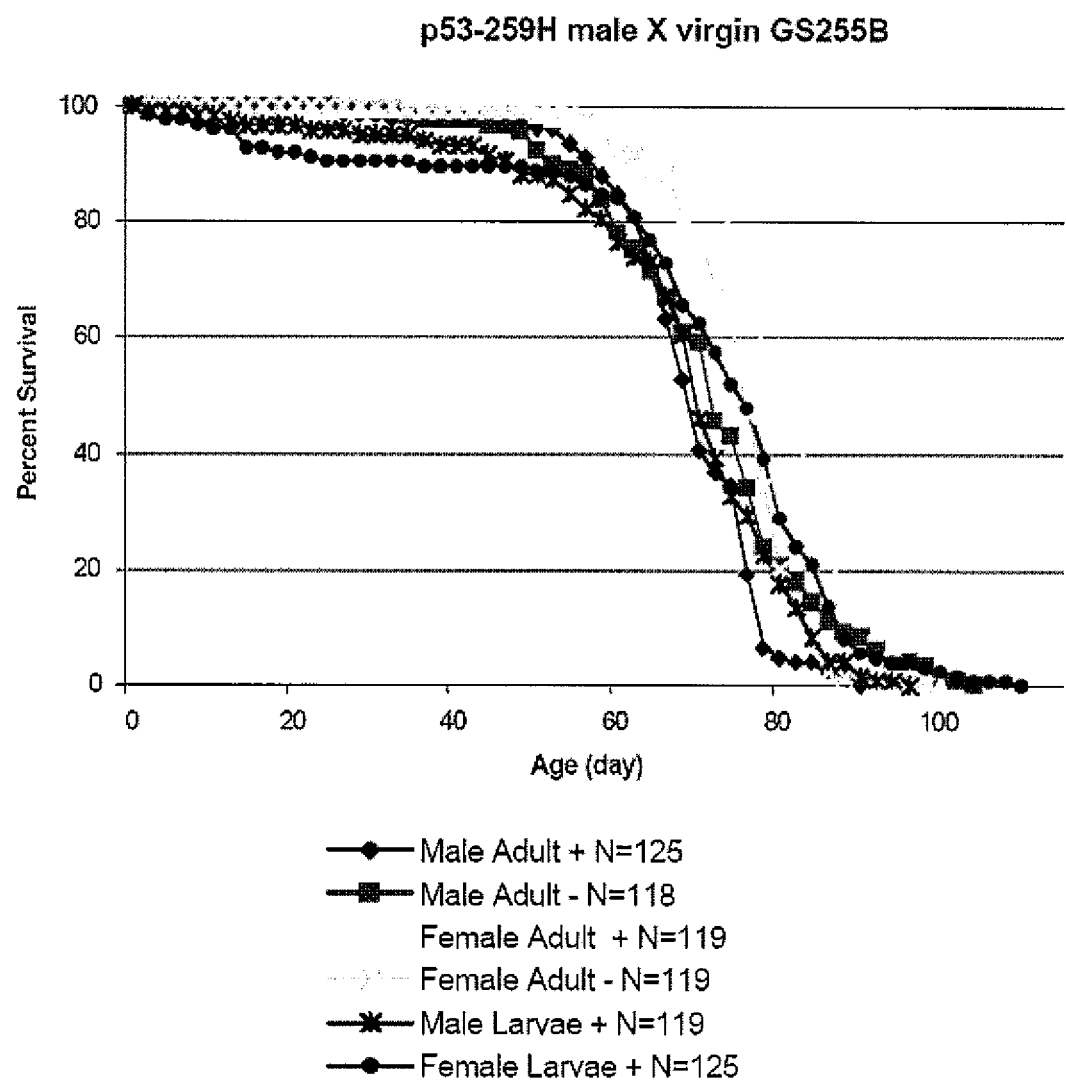
Figure 9E:
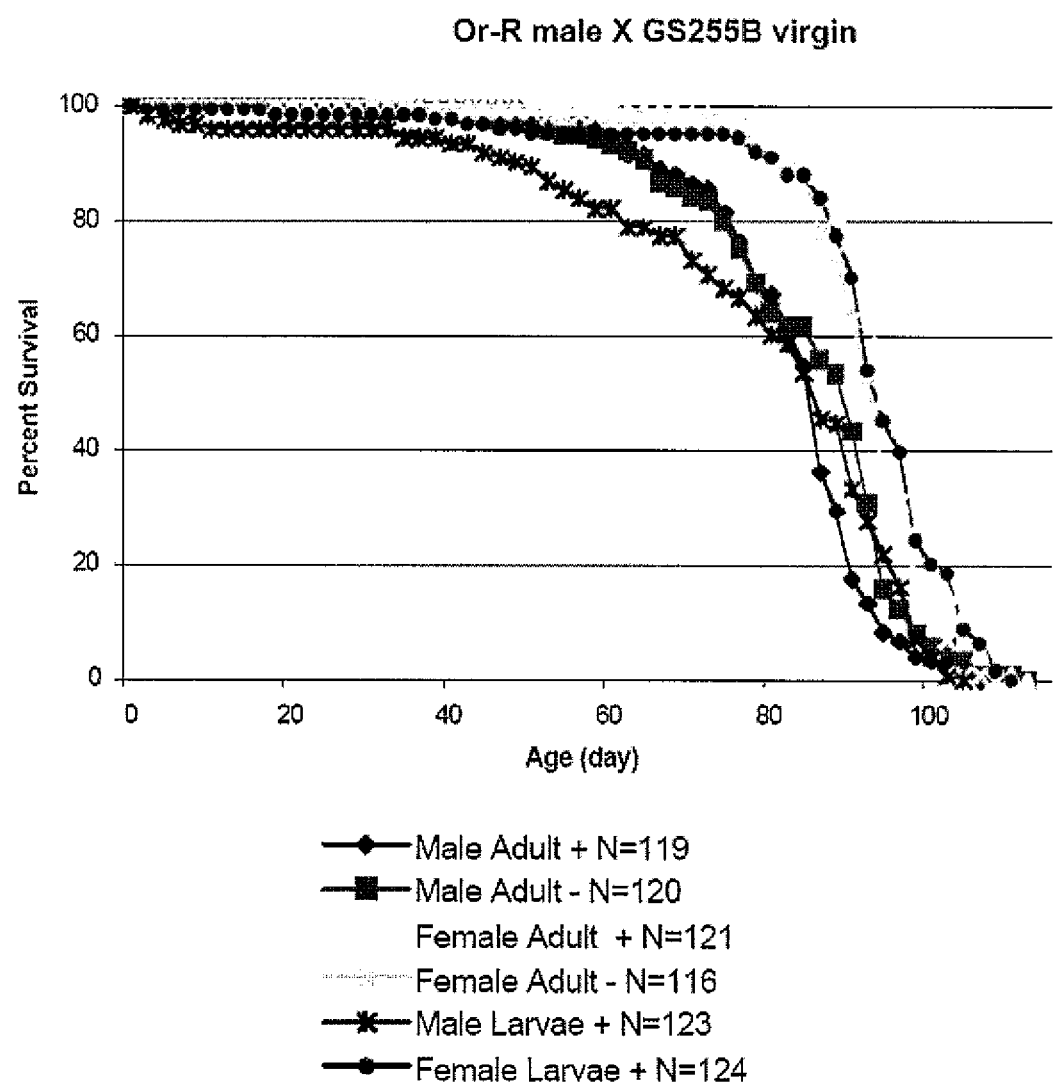
Figure 9F:
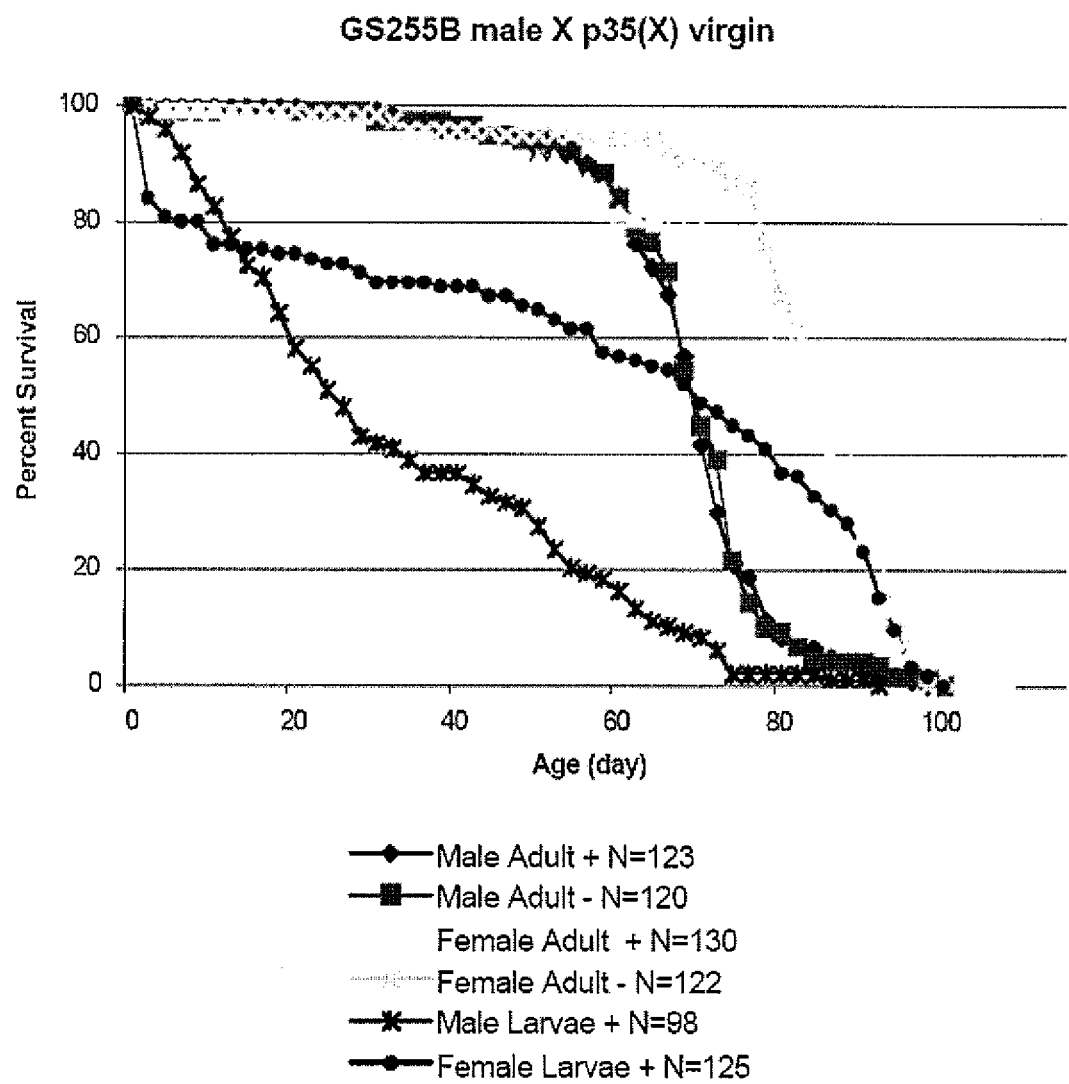
Figure 9G:
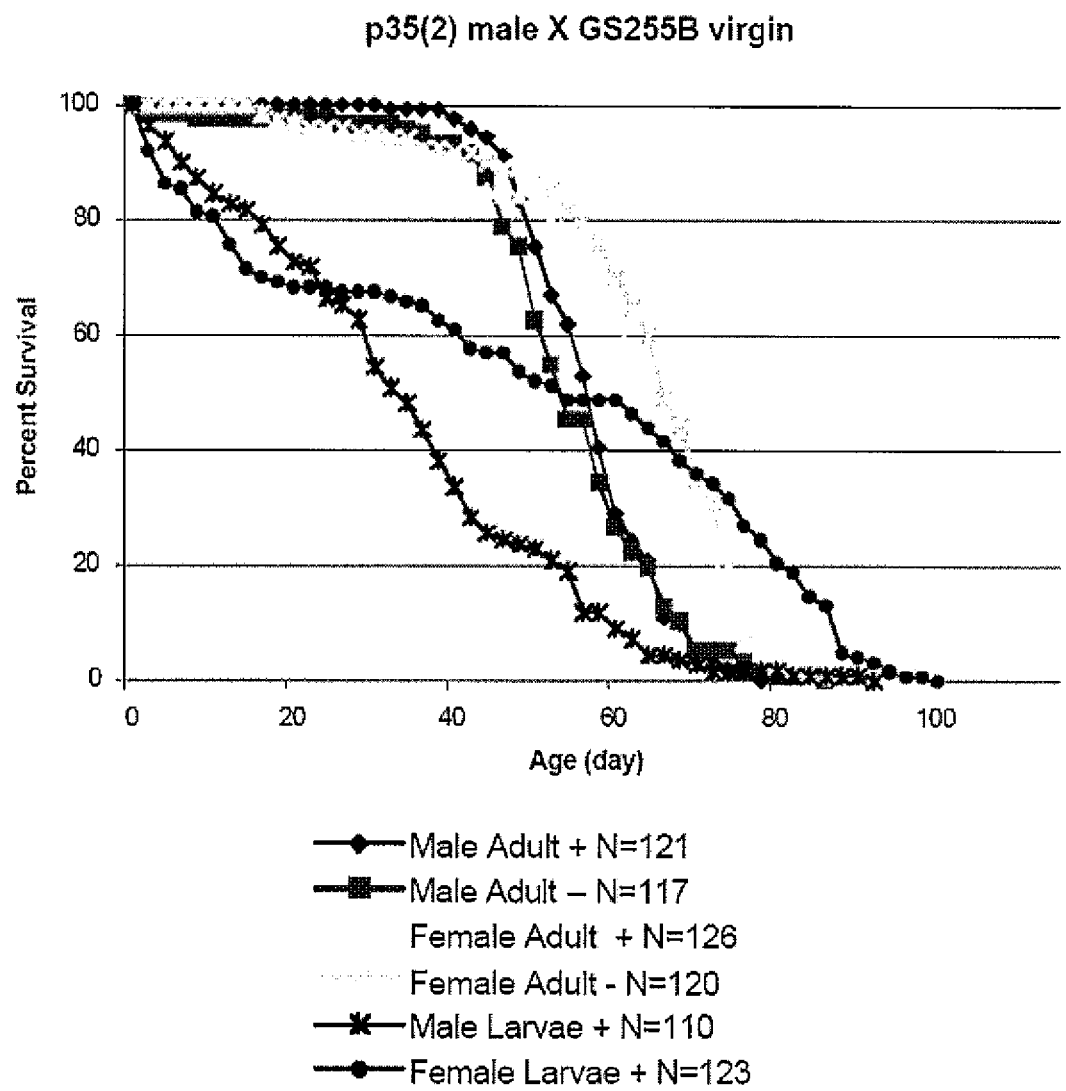
Figure 9H:
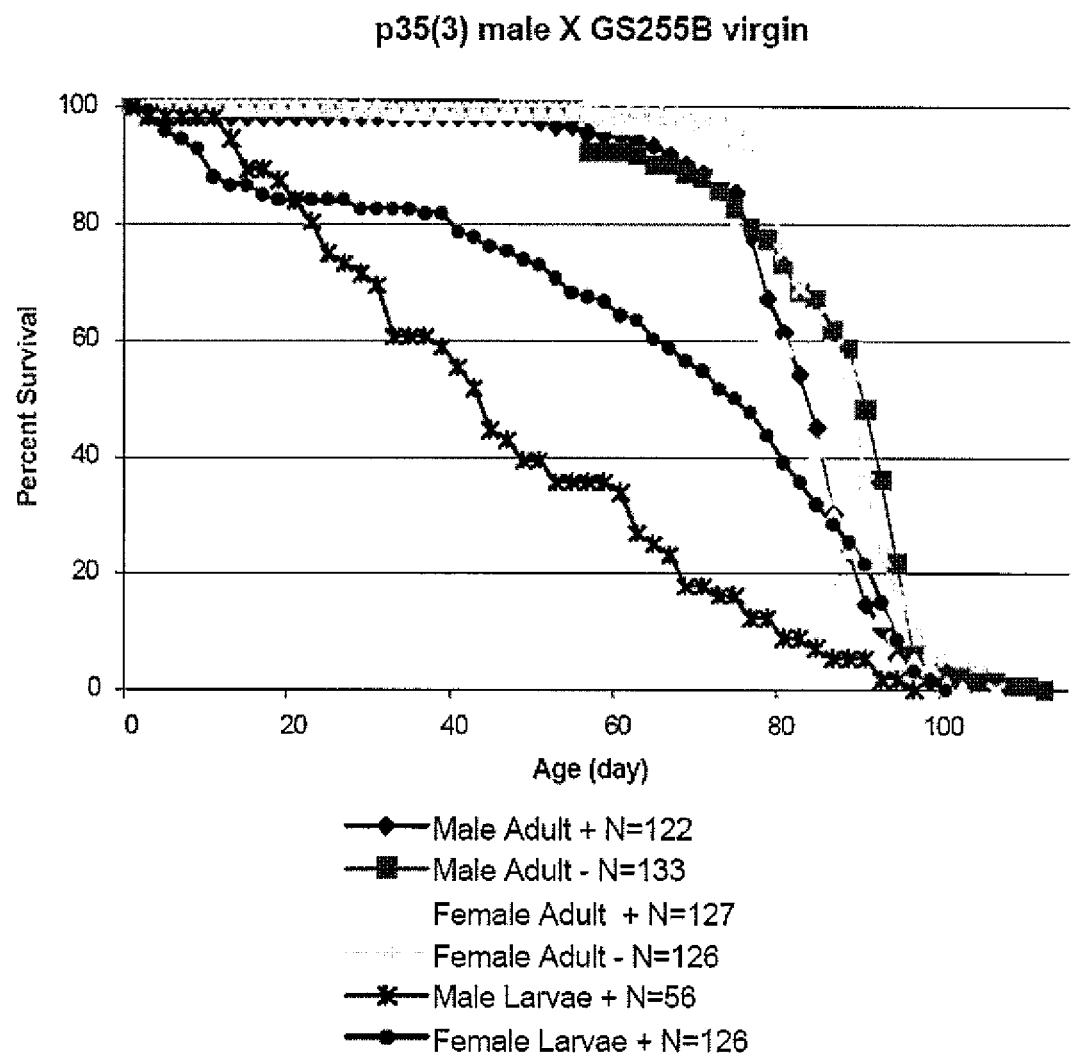

FIG. 9A-H Conditional over-expression of wild-type and dominant-mutant p53 transgenes and Baculovirus p35 transgenes using Geneswitch system. A-E. p53 transgene over-expression and controls. E-H. Baculovirus p35 over-expression and controls. In FIG. 9E, Female Larvae+N=3 lived 86, 92, 96 days respectively, with average 91.33 days. Even though the p53WT line is very sick, there should be about 100 males and 100 females/bottle totally, similar to the number of Cyo (not carrying p53WT TG) offspring. But only 3 females came out from more than 10 bottles (12 or 14 bottles). Counting results attached. In FIG. 9F, estimate # Male Larvae+ should have at least 80 mals/day coming out (Or-R). But only 40/bottle at most was observed. There might be reduction in Female numbers, too. In FIG. 9G, estimated # Male larvae+ should have at least 80 mals/day coming out (Or-R). But only 47/bottle at most was observed. There might be reduction in Female numbers, too. In FIG. 9H, estimated # Male Larvae+ should have at least 80 mals/day coming out (Or-R). But only 27/bottle at most was observed. Females came out 76/bottle/day at most, less than Or-R (136/bottle/day). In all of FIG. 9, UAS-p53WT, UAS-p35 CHX, CH2, CH3 lines all showed late eclosion; lots of pupa seemed dead. UAS-p35 CH3 eclosed slower and less than UAS-p35 CHX, CH2. Almost all pupa from p53WT failed to eclose (only 3 female escapers, died on D86, D92, D96) UAS-p35 CHX, CH2, CH3 lines have lower male/female ration than others (Or-R M/F>½).

Figure 10:
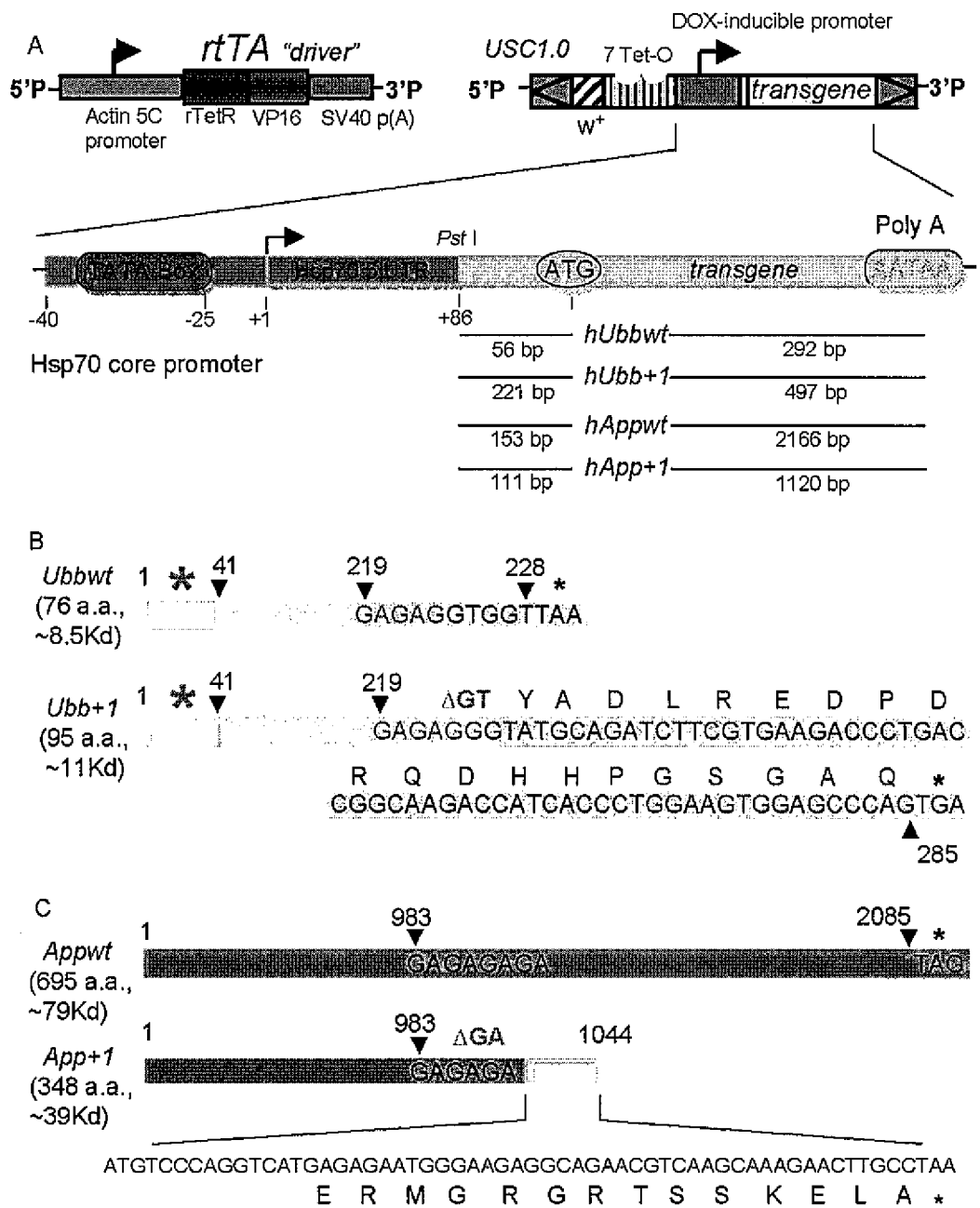

FIG. 10 Diagram of transgenic constructs. (A) The "Tet-on" conditional transgene expression system. The rtTA transgenic construct (or "driver") contains the tissue-general actin5C promoter driving expression of the artificial transcription factor rtTA. The target constructs were generated by cloning the indicated cDNA fragments downstream of the DOX-inducible promoter in the USC1.0 vector. The rtTA protein will bind to the 7 Tet-O sites in the target construct promoter and activate transcription only in the presence of DOX. (B) Diagram of the sequence and reading frames of the hUbbWT and hUbb[+1] constructs. The number 1 indicates the A of the normal ATG start codon for translation of hUbbWT. Note that any translation framed from position 2 (the T of the ATG start codon; or +1 reading frame) can produce the antigenic peptide (indicated by red asterisk), followed by a stop codon at position 41. The amino acid sequence of the peptide used to generate the hUbb+1 antibody is indicated. (C) Diagram of the sequence and reading frames of the hAppWT and hApp[+1] constructs. The GAGAG hotspot is located in hApp exon 9. The amino acid sequence of the peptide used to generate the hApp[+1] antibody is indicated. The transgenic strains are given names designed to be informative, and include the name of the inserted construct (e.g., hUbbWT or hUbb[+1]), the chromosome of insertion in parentheses (e.g., chromosome 2 or 3 or X), and a unique number indicating the independent insertion event. For example, hUbbWT(2)[118] is an insertion of the hUbbWT construct on the second chromosome, independent insertion event designated "118".

FIG. 11 Northern and Western analysis of conditional transgene expression. Flies of the indicated genotypes were cultured for one week on food supplemented +/−DOX, as indicated. A-C. Northern analysis. Total RNA was isolated from 30 flies, quantified by spectrophotometer, and 5 µg (1×) and 10 µg (2×) amounts were loaded for each sample. The resultant blot was hybridized with the indicated gene-specific probes. A. Control flies and hUbbWT transgenic fly strains. B. hAppWT transgenic fly strains. C. hUbb[+1] transgenic fly strain. D, E. Western analysis. Total protein was isolated from 30 male flies, diluted as indicated, fractionated using SDS-PAGE and Western blotted. D. Control and hUbbWT transgenic strain fly protein incubated with antibody specific for hUbb. E. Control and transgenic strain fly protein incubated with antibody specific for hApp.

FIG. 12 Western blot analysis using antibody specific for hUbb[+1]. Total protein was isolated from 30 male flies of the indicated genotypes, and ⅛ of the sample was assayed for the presence of protein that would be recognized by hubb[+1] antibody. Where indicated protein samples were diluted 1:2, 1:3, 1:5 or 1:10 to confirm sensitivity of the assay to relative protein concentrations. In panels B-F all samples are diluted 1:3. A. Molecular weight markers were run alongside His-tagged hubb[+1] purified from *E. Coli* cells as well as total protein isolated from 30 "young" (10 day old) and "old" (65 day old) male Or-R control flies, as indicated. B. "Young" (10 day old) flies of the indicated genotypes. C. Flies cultured +/− DOX for 26 days. D. Flies cultured +/− DOX for 48 days. E. Flies cultured +/− DOX for 67 days. F. Flies cultured +/− DOX for 82 days. Where visible the gel protein front (F) is also indicated. Solid arrowheads indicate two species of <20 Kd, either of which might represent Ubb[+1] monomer, which has an expected size of ~11 kd. Open arrowhead indicates species at expected position for Ubb[+1] ligated to one Ubb wild-type protein (~11 Kd+~8.5 Kd=~19.5 Kd). Single asterisk indicates species at expected position for Ubb[+1] ligated to two Ubb proteins (~11 Kd+~17 Kd=~28 Kd). Double asterisk indicates species at expected position for Ubb+1 ligated to three Ubb proteins (~11 Kd+~25.5 Kd=~37 Kd). Estimations of sizes of various species are presented in Supplemental Materials.

FIG. 13 Western blot analysis using antibody specific for hApp$^{+1}$. Total protein was isolated from 30 flies of the indicated genotypes, and assayed for the presence of protein that would be recognized by hApp$^{+1}$ antibody; "young" is 10 days old and "old" is 65 days old. A. Molecular weight markers were run alongside His-tagged hApp$^{+1}$ purified from *E. coli* cells, as well as the indicated dilutions of total protein isolated from flies in which the hApp$^{+1}$ transgenic construct was expressed. B. Purified His-tagged hApp$^{+1}$ protein from *E. coli* was run alongside protein from young and old Or-R control flies. C. Flies cultured +/− DOX for 26 days. D. Flies cultured +/− DOX for 48 days.

Figure 14:
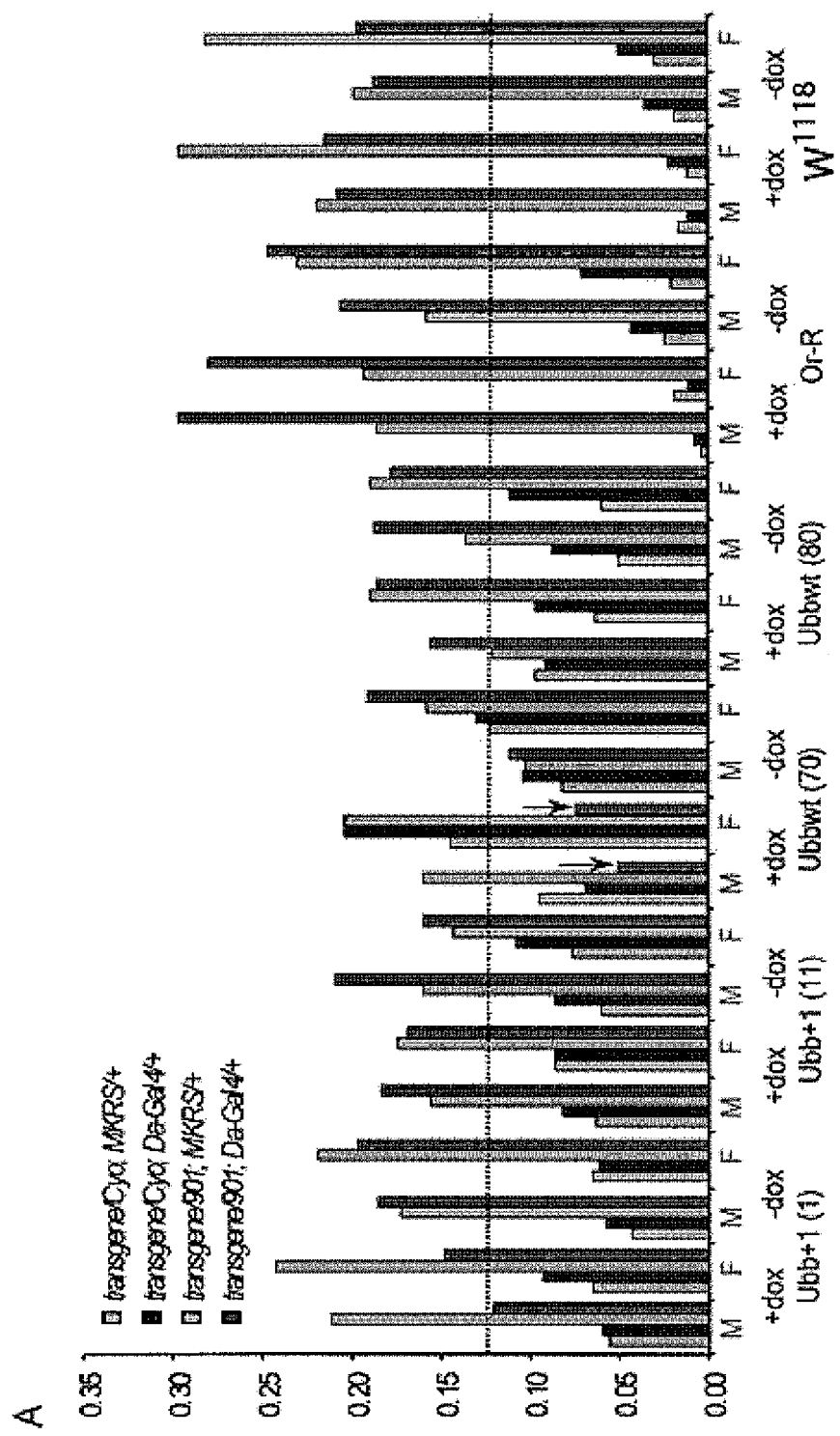
Figure 14:
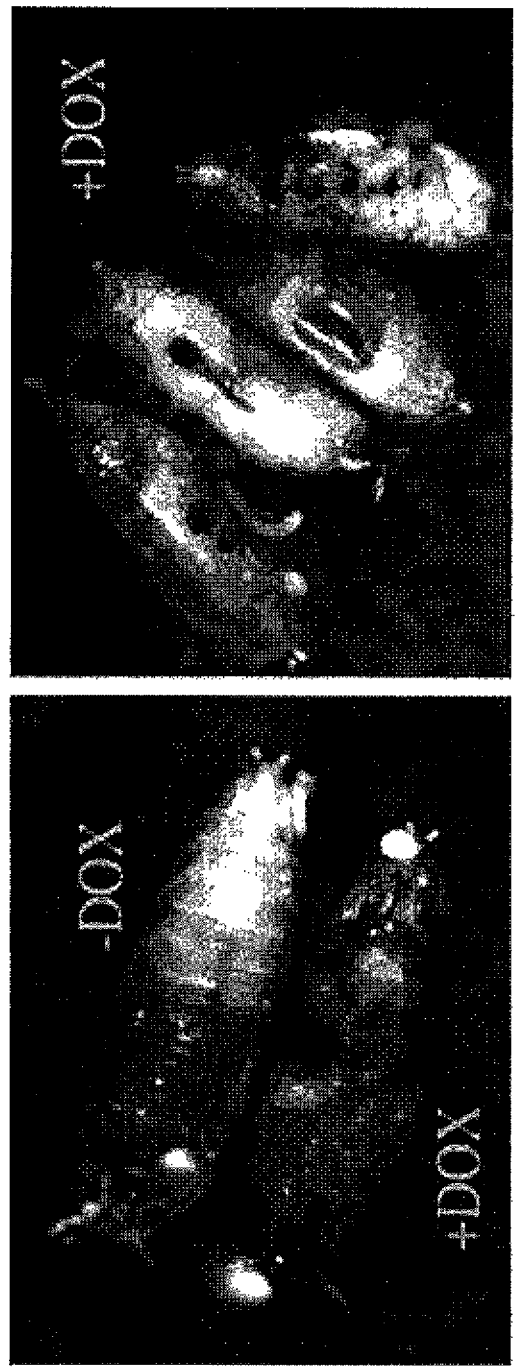

FIG. 14 Phenotypes of hUbb and hUbb+1 over-expression. A. Frequency of adult flies of the indicated genotypes emerging from crosses where larval development was allowed to occur in the presence and absence of DOX, as indicated. In these experiments a threetransgene configuration was used to achieve tissue-general, DOX-dependent expression. The daughterless-Gal4 driver (Da-Gal4) yields tissue general expression of the yeast transcription factor Gal4. The Gal4 protein activates expression of the "901" bridge construct encoding rtTA[M2alt] under the control of a UAS-promoter. In the presence of DOX, the rtTA will bind to the TetO sites in the target construct and activate expression of the transgene. Therefore DOX-dependent transgene expression can occur only in progeny that inherit all three constructs (blue bars). In the crosses to either Or-R wild-type or w[1118] flies, the target construct chromosome is replaced by a wild-type chromosome, thereby controlling for the effects of DOX itself. Arrows indicated reduced frequency of hUbbWT-expressing flies emerging due to DOX-dependent pupal lethality. B. Examples of pupal-lethal phenotype resulting from hUbbWT (70) transgenic line cultured +/− DOX, as indicated. C-F. Life span assays. Flies containing the indicated target construct insertions along with the Da-Gal4 driver and "901" bridge construct, as well as controls were generated as described above (A). The survival of flies of the indicated genotypes was assayed +/− DOX, as indicated. The Or-R control data and w[1118] control data is the same in each panel.

DETAILED DESCRIPTION

As set forth above, it is an unexpected discovery of the present invention that there exist an on/off switch mechanism at the genetic/molecular level for controlling the life span of an organism. In particular, it is an discovery of the present invention that the Xist gene in humans and the Sxl gene in *Drosophila* act as regulators for apoptosis and life span in the respective organism. In accordance with the discoveries of the present invention, there are provided methods for altering the aging process and for treating aging related diseases by manipulating the genes and gene products of these two genes and their respective host organisms.

While not intending to be limiting in any way, the following theoretical discussion is provided to further facilitate a complete understanding and appreciation of the present invention and its ramifications.

1. Aging and Life Span

Aging in living organisms is more correctly termed senescence, and is generally described as a cumulative, irreversible process resulting in decreased function and increased risk of death. Aging of some kind appears to affect all living organisms, from bacteria to humans (Ackermann, Stearns et al., 2003; Stewart, Madden et al., 2005). How long an individual lives—its life span—is characteristic of different species (Finch, 1990) (e.g. *Drosophila* can live 100 days, humans can live 100 years). Within each species, life span is typically quite variable—ven among individuals who are nearly genetically identical. Comparisons of life spans between groups are therefore often reported as mean and maximum life spans for the group or cohort.

The characteristic life spans of different species, and the variable life spans of individuals within a species are determined by how their unique genetic make-ups and environments make them more or less susceptible to these mortality mechanisms. For example, in cold-blooded (poikilothermic) animals like *Drosophila*, life span scales with temperature across a broad range in both sexes. This suggests that there is an irreversible, cumulative damage that leads to increased risk of death of the organism. In addition, certain interventions such as dietary restriction (DR) (Mair, Goymer et al., 2003; Partridge, Pletcher et al., 2005) or a mild heat stress (Tatar, Khazaeli et al., 1997) can cause a rapid and reversible shift in a population from a higher mortality rate to a lower one, which demonstrates that there are more acute mechanisms for regulating survival. Although the molecular nature of these mortality mechanisms is unknown, oxidative stress, hydrolytic stress, and toxic metabolite stress have each been implicated (Busuttil, Rubio et al., 2003; Hekimi and Guarente, 2003; Gems and McElwee, 2005; Landis and Tower, 2005; Wallace, 2005).

2. Evolutionary Theories of Aging

Like all things biological, aging and life span are shaped by genes and evolution (Kirkwood and Austad, 2000). It is now common understanding that deleterious mutations may be efficiently removed from the population through natural selection. However, a mutation that causes a problem only at late ages is not efficiently removed. For example, a human gene allele that predisposes individuals to Alzheimer's or Parkinson's disease is not efficiently removed from the population because by the time the disease is manifested the gene has usually already been passed on to the next generation (Finch and Sapolsky, 1999). The idea that such late-acting mutations accumulate in the genome and create the aging phenotype constitutes the "mutation accumulation" theory of aging.

The "antagonistic pleiotropy" model, on the other hand, suggests that gene alleles with late-acting deleterious effects are maintained in the population by active selection because these same gene alleles have benefits during the developmental and/or reproductive stages.

Significant experimental evidence exists in support of both mechanisms (Hughes and Reynolds, 2005). For example, the life span of *Drosophila* can be increased in the laboratory by selecting populations for late-life reproduction (Luckinbill, Arking et al., 1984; Rose, 1984; Rauser, Tierney et al., 2006).

3. Asymmetric Gene Inheritance

Antagonistic pleiotropy, as described above, refers to gene alleles that are beneficial at an early age and deleterious at a late age. Another type of antagonistic pleiotropy is between the sexes (e.g. a gene allele that benefits one sex of the species can be relatively deleterious to the other sex) (Rice, 1992; Rice, 1998; Chippindale, Gibson et al., 2001). This is possible because the sexes have different genotypes (e.g., X/X vs. X/Y), different environments (e.g., unique genital tract microbial fauna) and different selective pressures (e.g., childbirth). These sexually antagonistic genes are expected to be more likely to contribute to the aging phenotype. That is, all other things being equal, a gene allele optimized for function in both sexes is less likely to cause a problem during aging than a gene allele that functions sub-optimally in one or both sexes.

For example, the Y chromosome and the X chromosome are asymmetrically inherited in both *Drosophila* and humans.

Figure 1:
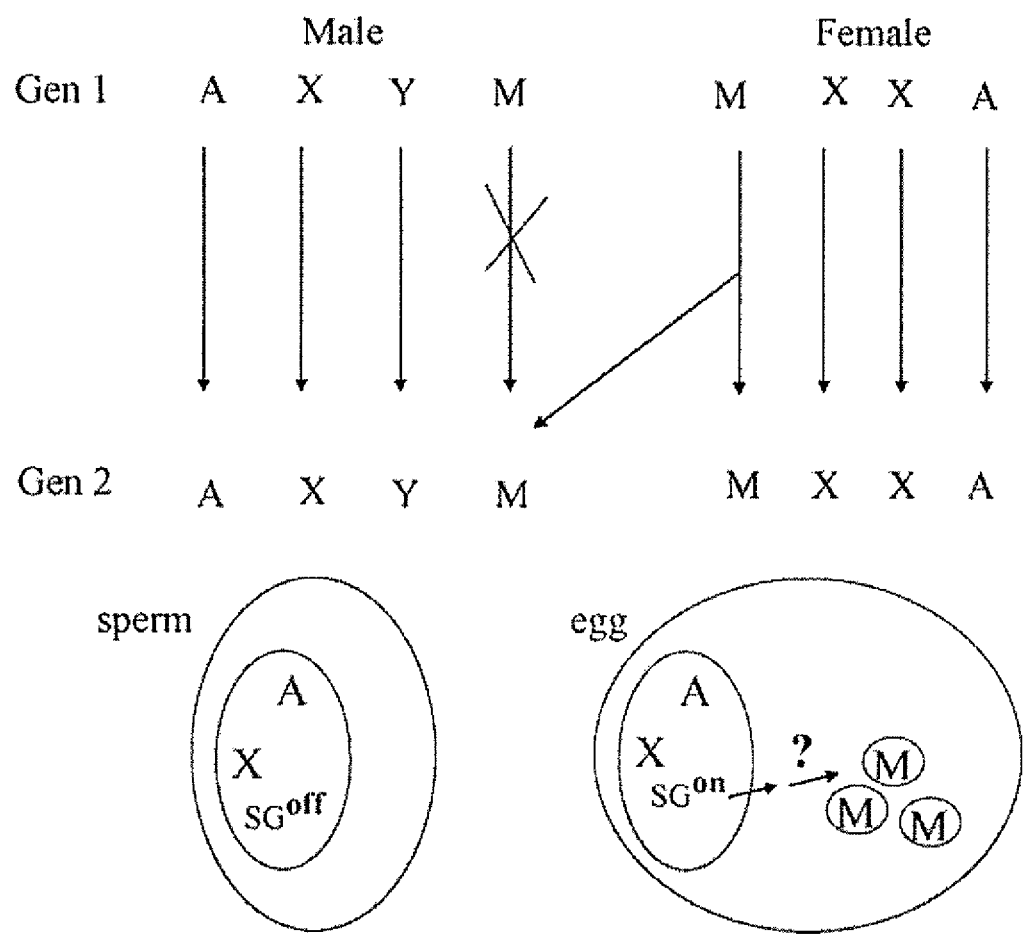
FIG. 1 Asymmetric segregation of the X and Y chromosome and mitochondrial genome (M). *Drosophila* and human males in generation 1 do not pass mitochondrial genes (M) on to their offspring in generation 2, rather these genes come from the female parent (maternal inheritance). Asymmetric segregation or maternal inheritance of the mitochondrial genome means the female gamete or egg contributes the functional mitochondrial genomes to the embryo while the male gamete or sperm does not. A, autosomes; M, mitochondrial genomes. SG=Switch Gene and Sex-determination Gene.

In both species, females are genotype X/X and males are X/Y (FIG. 1). These two genomes may be differentially optimized for each of the sexes and have different contributions to the aging phenotype.

Let's first consider the Y chromosome. Since the Y chromosome is inherited only through the male, it means that genes on the Y chromosome are optimized for function only in males. Evidence for the better fitness of Y to the male sex is found in the fact that genes on the Y chromosome are generally involved in male-specific functions such as spermatogenesis and male sexual differentiation (Charlesworth and Charlesworth, 2005).

In contrast, the X chromosome exists in both the male and the female. However, because females have two copies of the X chromosomes, it follows that females have two copies of each gene on the X chromosome whereas males only have one copy. This means that through evolution, genes on the X chromosome spend more time under selection in females than they do in males. The difference in evolutionary time exposure in the two sexes suggests that there might be some skew in the distribution of genes with sex-specific functions between the X chromosome and the autosomes.

Data from the genome projects appear to support this hypothesis. For example, in *Drosophila*, the X chromosome is about half the size of the 2nd and 3rd chromosomes (the estimated number of genes on the X is about 2309 (~16%), about 5688 (~40%) on the 2nd, and about 6302 (or 44%) on the third, out of a total of about 14384. On the *Drosophila* X chromosome, genes involved in oogenesis appear to be over-represented whereas genes involved in spermatogenesis are under-represented, as might be expected for a chromosome better optimized for the female (Table 1).

The same skew exists for genes showing femalebiased or male-biased expression at the RNA level (Arbeitman, Furlong et al., 2002; Parisi, Nuttall et al., 2003; Oliver and Parisi, 2004; Parisi, Nuttall et al., 2004). In addition, the X chromosome was also found to be a hotspot for sexually antagonistic fitness variation, i.e., naturally occurring X chromosomes often contain gene alleles that benefit one sex more than the other in terms of traits like male reproductive success and female fecundity (Gibson, Chippindale et al., 2002).

4. Mitochondrial Asymmetric Inheritance

Because mitochondria are asymmetrically inherited (maternal inheritance only), the force of natural selection acting on the mitochondrial genome (mitogenome or M) and the mitogenome-nuclear genome interactions is effective only in females (FIG. 1) (Rand, Clark et al., 2001; Rand, 2005; Rand, Fry et al., 2006). In other words, the mitochondrial genome is optimized for function in the female. The male is inherently less fit because the highly beneficial mitochondrial genome is not optimized for his genome. As set forth above, this asymmetric fitness of the X genome will contribute to the observed aging phenotype, and perhaps do so more in males than females. This is one possible explanation for the observation that in many species, including *Drosophila* and humans, males tend to have shorter life spans than females.

At the genome level, it was found that genes involved in general mitochondrial function were fairly evenly distributed (17% vs. 36% and 47%, respectively; Table 1). However it is interesting to note that genes involved in programmed cell death are reduced in abundance on the X chromosome, especially genes with anti-apoptotic function. Out of the 28 genes involved in programmed cell death found on the X chromosome (Table 2), pro-apoptotic functions outnumber anti-apoptotic functions 25 vs. 3. The observation that (anti)apoptotic genes are preferentially located on the autosomes (like spermatogenesis genes) suggests some degree of sexual antagonism with regard to apoptosis regulation.

5. Apoptosis

Apoptosis is a form of active cellular suicide involving characteristic morphological changes such as membrane blebbing. It functions to remove cells that are otherwise unwanted, such as in the developmental sculpting of human fingers and *Drosophila* gut, or dangerous, such as virally-infected cells (Baehrecke, 2002; Baehrecke, 2003; Cashio, Lee et al., 2005; Yin and Thummel, 2005).

An evolutionarily-conserved set of cysteine proteases called the caspases carry out most of the cellular self-destruction (Abraham and Shaham, 2004). The caspases exist in a relatively inactive state in virtually all cells of eukaryotes where they are regulated by a balance of specific activators and inhibitors. The mitochondria regulate apoptosis by releasing cytochrome C and other pro-apoptotic factors into the cytosol in response to various "death signals" (Adams, 2003). These signals include nuclear DNA damage, p53 activation and the balance of Bcl-family member activities. The released cytochrome C binds to Apaf-1 protein which promotes assembly of a multiprotein complex called the apoptosome and activates the initiator caspase-9 and a "caspase cascade" (Adams and Cory, 2002; Arama, Bader et al., 2005).

Since apoptosis is essential to the development and function of both male and female animals, both sexes must be capable of regulating a basic cellular apoptotic machinery.

6. The Mitochondria and Apoptosis in Gametogenesis

Mitochondria play a central role in the differentiation of the gametes in *Drosophila* and other species. Mitochondrial rRNA appears to be an essential component of the germ plasm—the maternal, cytoplasmic determinant of germ-cell fate (Amikura, Sato et al., 2005; Kobayashi, Sato et al., 2005).

During *Drosophila* oogenesis, ribosomal RNAs encoded by the mitochondria are transported out of the mitochondria into the cytosol of the oocyte where they are required for formation of the morphologically distinct germ plasm. The cells that inherit the germ plasm during the development of (male or female) embryos give rise to the germ cells in the adult. This is consistent with an ancient role for the mitochondria in the evolution of sexual differentiation and germ-line/soma distinctions.

The observation that mitochondrial genes are almost never inherited through the male means one or both of two things (Nishimura, Yoshinari et al., 2006): (i) There exists a male-specific mechanism for destruction of functional mitochondrial genomes, or (ii) the mitochondrial genomes that are delivered to the oocyte from sperm are non-viable in the oocyte or embryo environment. In either event we can state that there is a female-specific mechanism for mitochondrial inheritance, and males either lack or for some other reason do not express this mechanism (FIG. 1).

The dramatic behavior of mitochondria in germ cells offers some clues to the underlying molecular mechanisms. For example, oogenesis in many species is characterized by a morphologically distinct aggregate of mitochondria and other cytoplasmic material called the Balbiani body (Kloc, Bilinski et al., 2004; Wilk, Bilinski et al., 2005). During development, *Drosophila* oocyte is connected to its sister germ-line cyst cells via cytoplasmic bridges, and the Balbiani body and a specialized actin structure called the fusome mediate early movement of mitochondria into the oocyte (Cox and Spradling, 2003). It may be that only this early population of oocyte mitochondria is incorporated into the germ plasm to be inherited by the next generation.

Later the cyst cells dump more mitochondria into the oocyte cytoplasm prior to—or coincident with—undergoing a form of programmed cell death (Buszczak and Cooley, 2000). Subsequently a significant number of oocytes and eggs may be destroyed and reabsorbed in the *Drosophila* ovary, in a process modulated by insulin-like signaling (Drummond-Barbosa and Spradling, 2001; Flatt, Tu et al., 2005).

Germ-line cysts, mitochondrial transport mechanisms and multiple apoptotic-like processes also appear to function in mammalian oogenesis (Pepling and Spradling, 2001; Hussein, 2005). In adult mammals, most female germ cells are destroyed prior to fertilization in an apoptosis-like process called atresia. It has been hypothesized that atresia is one mechanism to remove oocytes carrying mutant mitochondria and thereby ensure the inheritance of functional mitochondria by the next generation (Krakauer and Mira, 1999).

In summary, female inheritance of mitochondrial genomes appears to be accomplished by active transport and concentration of (probably a subset) of mitochondria into the oocyte, and perhaps the destruction of cells containing unwanted mitochondria.

In the male germ line the mitochondria undergo a series of dramatic transformations linked to the morphological development of the sperm, and ultimately give rise to highly derivative structures containing only a small fraction of the starting mitochondrial DNA (e.g., the mammalian sperm midpiece and the insect sperm "nebenkern"). In *Drosophila* an apoptosis like process has been found to be essential for normal sperm development, in particular the spermatid individualization step in which most of the cytoplasm and the majority of the mitochondria are eliminated from the developing spermatids (Fabrizio, Hime et al., 1998; Arama, Agapite et al., 2003; Arama, Bader et al., 2005; Cashio, Lee et al., 2005).

As a further hint for the underlying molecular mechanism, ectopic expression of the baculovirus caspase-inhibitor gene p35 in the testes, or mutation of the *Drosophila* homologs of Cytochrome C, Apaf or Caspase-9 are found to cause severe defects in this apoptosis-like process. These essential apoptosis events are attractive as a possible mechanism for sperm-specific destruction of mitochondrial genomes. In the unicellular alga *C. reinhardii* and the Japanese pet fish *O. latipes*, the fate of the mitochondrial DNA has been examined in detail, and in each case what little male mitochondrial DNA makes it to the egg is actively destroyed just after fertilization (Nishimura, Yoshinari et al., 2006).

7. Evolution—the Benefit

The asymmetric inheritance of the M, X and Y chromosomes creates abundant opportunities for antagonistic pleiotropy of gene function between the sexes. This sets up a situation of balancing competition and selection between the male and female which is thought to benefit both because it promotes genetic diversity—sometimes called a Red Queen situation (Nowak and Sigmund, 2004). One may envision this situation as a driving force in eukaryotic evolution as follows: The male is inherently less fit because he receives an M that is not optimized for his genome. Since selection cannot act in the male to improve M gene function, it acts to improve the fit of the male genome to the M. Because of this, there is a strong selection force in the male to select for mutation of the X so as to compensate for his lack of fitness—as opposed to the autosomes, which they share equally. This leads to hypermutation of the X in the male: Such X-linked mutations will be heterozygous in his daughters and might benefit him and his grandsons. Since the male is characterized as having suboptimal mitochondrial function, it is likely that the hypermutation of the X in the male might proceed primarily through oxidative mechanisms.

Strong selective pressure is predicted to act on the male to make spermatogenesis and sperm success as dependent upon the mitochondria as possible, e.g., motile sperm, regulated apoptosis and the elaborate morphological changes. In this way the male "forces" the female to give him as good M genes as possible. In other words, the males have created a limit to the extent to which the female can make the mitochondria sub-optimal for his genome, because if she makes it worse her eggs won't get fertilized. This is the likely explanation for the fact that across species males are found to produce large numbers of sperm, all of which appear to be marginally functional. Natural selection in the male and female will act on the X and on X-autosome interactions to create ever-more distinct gametogenesis mechanisms—in order to "force" the opposite sex into providing them with as good a set of genes as possible (e.g. natural selection acts in the female to make oogenesis as dependent upon the X and X-autosome interactions as possible to try to force males into giving her as good (and un-mutated) X chromosomes as possible). This dance between the male and female through time drives the evolution of multicellularity and the separation of germ-line and soma. For example, natural selection acts in the male to make spermatogenesis as dependent upon the mitochondria as possible, including the elaboration of a separate and disposable soma that houses and supports spermatogenesis and is highly dependent on mitochondrial function.

The same general rules can be extended to mating choice for several species. For example female *Drosophila* select males based primarily on energetic (mitochondriadependent) traits—he chases her. In turn, males are predicted to select females based primarily on potential for maternal contribution (e.g., size of reproductive tissues) and X chromosome genetic diversity (e.g., odor). Consistent with this idea, X chromosome gene expression appears to be especially variable in human females (Carrel and Willard, 2005).

The evolutionary considerations set forth above may be used to make predictions as to what types of genes are more likely to exhibit antagonistic pleiotropy and be involved in limiting the life span of flies and mammals—specifically, genes controlling mitochondrial function and sex-specific functions such as gametogenesis, sex-determination, sex-specific differentiation, behavior and metabolism.

8. Life Span Quantitative Trait Loci (QTLs)

Quantitative trait loci (QTLs) are regions of the chromosome that are associated with differences in a scalable phenotype such as bristle number or life span. Life span QTLs can be identified based on the general strategy of crossing a short-lived strain with a long-lived strain, deriving sub-strains of varying life span, and correlating specific chromosomal genetic markers with shorter or longer life span across strains. This strategy works quite well in organisms such as *Drosophila, C. elegans* and mouse and QTLs affecting life span have been identified in several labs (Nuzhdin, Pasyukova et al., 1997; Leips and Mackay, 2000; Vieira, Pasyukova et al., 2000; Jackson, Galecki et al., 2002; Mackay, 2002; Ayyadevara, Ayyadevara et al., 2003; Valenzuela, Forbes et al., 2004; Wang, Lazebny et al., 2004; Hsu, Li et al., 2005; Nuzhdin, Khazaeli et al., 2005).

One of the most striking observations from these studies is the degree of sex-specificity of the QTLs—many or most of the life span QTLs identified in both *Drosophila* and mouse are sex-specific, and their effects can be modified by mating (Reiwitch and Nuzhdin, 2002). This has led to the conclusion that antagonistic pleiotropy of gene function between sexes and developmental stages shapes life span (Vieira, Pasyukova et al., 2000; Leips, Gilligan et al., 2005).

Although it is difficult to go from QTL to a specific gene, there have been some successes (De Luca, Roshina et al., 2003; Miller, 2005). For example the *Drosophila* gene DDC catalyzes the final step in the synthesis of the neurotransmitters dopamine and serotonin and affects both courtship behavior and life span.

9. Life Span Mutations and Transgenes

A number of single-gene mutations have been identified that can increase *Drosophila* life span (Helfand and Rogina, 2003; Ford and Tower, 2006). Where tested, most of the mutations appear to affect both male and female, although there is often a bias in effect for one sex or the other (Burger and Promislow, 2004).

In one example, ubiquitous over-expression of the antioxidant enzyme Cu/ZnSOD in *Drosophila* was found to increase life span in both male and female flies (Sun and Tower, 1999). Cu/ZnSOD is found in the cytoplasm and outer mitochondrial space in most eukaryotic cells (Landis and Tower, 2005). Using two independent huCu/ZnSOD transgenes, the preferential over-expression of human Cu/ZnSOD (huCu/ZnSOD) in *Drosophila* motorneurons, was also found to increase life span in males and females, (Parkes, Elia et al., 1998). Interestingly, a recent analysis of one of those huCu/ZnSOD transgenes in several long-lived genetic backgrounds found life span extension to be primarily in females (Spencer, Howell et al., 2003). This might indicate some sex bias in the mechanism of life span extension by huCu/ZnSOD over-expression in *Drosophila* motorneurons, or might represent a sex bias in the expression of that one particular transgene insertion.

Another striking example of what could be sexually antagonistic gene function is a seminal fluid protein (produced in the *Drosophila* male) that may help his sperm compete against other male's sperm—yet at the same time shortens the life span of the inseminated female (Wolfner, 2002). The fact that genes can be expressed in one sex but function in the other sex, either through insemination or maternal contribution to the embryo, provides ample opportunities for the evolution of sexually antagonistic gene functions.

In yet another example, a conserved insulin-like signaling pathway has been identified that negatively regulates life span in *C. elegans, Drosophila* and mice (Bartke and Brown-Borg, 2004; Kenyon, 2005). In *Drosophila*, inhibition of the insulin-like pathway or transgenic over-expression of the target transcription factor dFOXO increases life span preferentially in females (Clancy, Gems et al., 2001; Tatar, Kopelman et al., 2001; Hwangbo, Gersham et al., 2004). This suggests that in *Drosophila*, insulin-like signaling normally limits life span more in females than in males.

One possible explanation for the negative-life span regulation of this pathway may be because this pathway regulates reproduction and metabolism and females invest more metabolic resources in reproduction than do males.

Dietary restriction (DR) also increases life span to a greater extent in *Drosophila* females than it does in males (Magwere, Chapman et al., 2004). A mild stress applied early in life can sometimes increase the life span of an animal, an effect called hormesis (Cypser and Johnson, 2003). In *Drosophila*, mild heat and other hormetic stresses tend to benefit males more than females (Vieira, Pasyukova et al., 2000; Burger and Promislow, 2004).

There are also a small number of interventions and genes that have been shown to increase life span in rodents (Miller, 2005). DR increases both male and female life span, but may do so more in females (Masoro, 2005). Ames dwarf mouse, Snell dwarf mouse, and Little dwarf mouse represent mutations in the insulin-like signaling and growth hormone pathways and increase life span in both sexes, again with a preference for females (Bartke, 2005). Strikingly, in the Ames dwarf mouse, extension of life span correlates with an almost complete loss of gender dimorphism in the gene expression patterns observed in the liver (Amador-Noguez, Zimmerman et al., 2005). This was interpreted to suggest that a reduction in costly physiological investments in reproduction contributes to extended longevity.

Genes known to regulate human life span are rare (Perls and Terry, 2003; Martin, 2005). Importantly, a key regulator of mitochondrial-dependent apoptosis pathways, p53, is implicated in life span regulation in *Drosophila*, mice and humans (Tyner, Venkatachalam et al., 2002; Gaspari, Pedotti et al., 2003; Maier, Gluba et al., 2004; Bauer, Poon et al., 2005; van Heemst, Mooijaart et al., 2005; Gatza, Hinkel et al., 2006).

Regulation of life span by the insulin-like pathway in the hermaphrodite nematode *C. elegans* correlates with levels of oxidative stress resistance (Larsen, 1993). Life span extension occurs in the adult and is mediated by a set of genes including small heat shock proteins and ones similar to the classic Phase II response involved in detoxification and excretion of lipophilic metabolites (Walker, White et al., 2001; Lee, Kennedy et al., 2003; Murphy, McCarroll et al., 2003; An, Vranas et al., 2005; Gems and McElwee, 2005).

Interestingly, one of the major targets of reduced insulin-like signaling is the mitochondrial antioxidant MnSOD (Honda and Honda, 1999) —which has been shown to be sufficient to increase life span in adult flies (Sun, Folk et al., 2002).

The ability to inhibit specific gene expression in *C. elegans* by simple feeding of dsRNA has allowed for genome-wide screens for negative regulators of life span, and the assessment of when during the life cycle these genes function to inhibit life span. In addition to the insulin-like signaling pathway, a major class of genes identified were ones with mitochondrial functions (Dillin, Hsu et al., 2002; Lee, Lee et al., 2003). The data suggest that a large number of mitochondrial genes, and presumably the mitochondria itself, function during *C. elegans* development to limit the life span of the subsequent adult. Taken together, the data suggest that in *C. elegans* the mitochondria can function during development to limit subsequent adult life span, and can function in the adult to promote life span.

So far there is no indication that these life span effects involve apoptotic-like mechanisms. Virtually all experiments were done in hermaphrodites, so few male/female comparisons are available (McCulloch and Gems, 2003).

In summary the genetic and transgenic studies clearly support a role for mitochondria-related genes and functions in aging and life span regulation across species, with hints of important sex-specific differences. The predicted importance of other sex-specific genes and pathways is indicated by the QTL studies, but remains to be confirmed by the identification of specific genes with differing effects on male and female life span. The trends that have emerged so far are that female life span may be more limited by the insulin-like signaling pathway and DR, while male life span may be more limited by (oxidative) stress.

10. Oxidative Stress and Apoptosis in Old Animals

A large body of data demonstrates a correlation between mitochondrial misfunction, oxidative stress and aging across species (Walter, Murasko et al., 1998; Hekimi and Guarente, 2003; Fridovich, 2004; Landis and Tower, 2005; Wallace, 2005). During aging, the concentration of oxidatively-damaged macromolecules and abnormal mitochondria are increased and the oxidative stress-response genes are expressed in tissue-specific patterns. These observations appear to apply generally to both males and females of *Drosophila*, rodents and humans. As specific molecular markers for apoptosis become available, it has become apparent that apoptosis is also occurring during aging in tissue-specific patterns in *Drosophila* and mouse, however there has been little if any comparison of male vs. female patterns (Kujoth, Hiona et al., 2005; Zheng, Edelman et al., 2005).

11. Role of Apoptosis in Regulating Life Span

Figure 2:
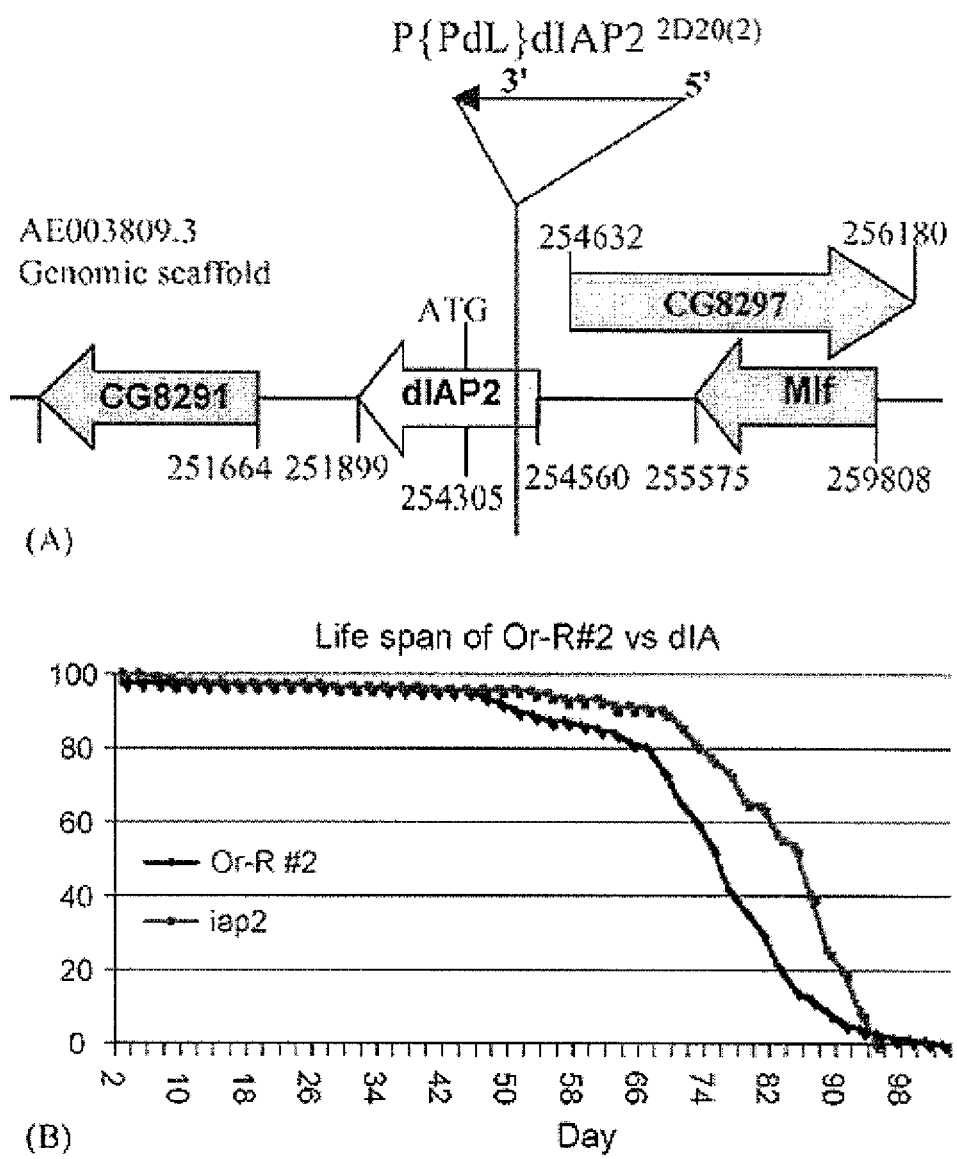
FIG. 2 Identification of dIAP2 mutation life span extension in male *Drosophila*. (A) Diagram of PdL insertion in the dIAP2 gene. (B) dIAP2 mutation effect on life span relative to Oregon R WT control chromosome. Survival curve for male flies of control genotype y ac w; +/+; rtTA(3)E2/+ and experimental genotype y ac w; PdLdIAP2/+; rtTA(3)E2/+ passaged on food containing 60 μg/ml doxycycline from day 4 onwards, data re-plotted from (Landis, Bhole et al. 2003).

The observation of apoptotic events in old animals begs the question of whether this process limits life span. Results of a genetic screen support a role for apoptosis in *Drosophila* life span regulation (FIG. 2).

Previously, 10,000 male flies were generated where each fly had at least one new insertion of an engineered P transposable element called PdL (Landis, Bhole et al., 2003). PdL contains an outwardly-directed, doxycycline(DOX)-regulated promoter at its 3' end, that can drive over-expression of a gene downstream of the insertion site. The longest-lived of the 10,000 male flies contained a single PdL insertion causing over-expression of dIAP2—a known anti-apoptotic caspase inhibitor with conserved function in humans (FIG. 2A). One hundred and nine (109) strains were derived from the longest-lived flies and the strains were re-tested for life span in cohorts of ~400 male flies, +/− DOX. dIAP2 over-expression in the presence of DOX yielded the second-longest life span of all 109 lines and a +16% life span increase relative to the control chromosome (FIG. 2B).

The dIAP2 mutation had not previously been pursued because there was only a small difference between the +DOX and −DOX life spans (Landis, Bhole et al., 2003). It now appears that this is due to the leaky nature of the mutation and the potency of the gene product for life span effects (Yishi Li and J. T., unpublished observations). A similar screen for life span-extending mutations in *Drosophila* identified the dPOSH gene, which may also be involved in apoptosis regulation (Aigaki, Seong et al., 2002).

As demonstrated in Example 1, the apoptosis regulators p53 and baculovirus p35 also regulate adult *Drosophila* life span. Finally, Seroude and coworkers have recently found that inhibiting apoptosis in *Drosophila* muscle tissue by over-expression of caspase inhibitors dIAP1 or baculovirus p35 increases both muscle function and life span (Personal communication: Tissue-specific inhibition of apoptosis extends *Drosophila* life span, J. Zheng, J. Yeung and L. Seroude, submitted). Taken together the data suggest that, in *Drosophila* at least, apoptotic-like mechanisms act in tissue- and developmental stage-specific ways to regulate life span. However it should be noted that other studies indicate that p53 can affect *Drosophila* life span via a mechanism other than apoptosis (Bauer, Poon et al., 2005). Some preliminary data suggest intriguing sex-specific differences in the way apoptotic regulators affect *Drosophila* life span (Waskar et al, unpublished observations) and this should be a particularly interesting area for future research.

12. A Binary Switch Model for Sex Determination, Apoptosis and Life Span

The inventor has devised a molecular model consistent with the data and evolutionary theories using a binary switch metaphor—the on/off status of a gene that regulates mitochondrial genome maintenance.

Because the mitochondrial genome is asymmetrically inherited, it follows that there must exist some mechanism to ensure that the mitochondrial genomes are inherited through the cytoplasm of the oocyte and are (almost) never inherited through the sperm, as discussed above. It is most likely that the asymmetric segregation is accomplished by a mitochondrial inheritance system expressed in the oocyte that is not expressed in the sperm, i.e., a mitochondrial inheritance system downstream of the female germ-line sex determination pathway (FIG. 1).

One possible underlying molecular mechanism for this female-specific mitochondrial inheritance is that only the mitochondrial genomes present in the oocyte are licensed for replication—therefore any mitochondrial genes coming in from the male would be diluted out, as appears to be the case. Similarly, the mitochondria in the oocyte could be protected by a female-specific anti-apoptotic mechanism. Mitochondria actively turn-over in many cell types. Moreover, apoptosis is reported to be the default state for the mitochondria (Jones, 2000; Brookes, 2005), which means that in the absence of some anti-apoptotic signal, the mitochondria and its genome will tend to self-destruct.

Regardless of the precise molecular nature of the female-specific mitochondrial inheritance mechanism, it represents a mitochondrial maintenance signal downstream of the female-sex determination pathway (FIG. 1), and is most simply thought of as an anti-apoptotic signal sent to the mitochondria.

Figures 3, 7B:
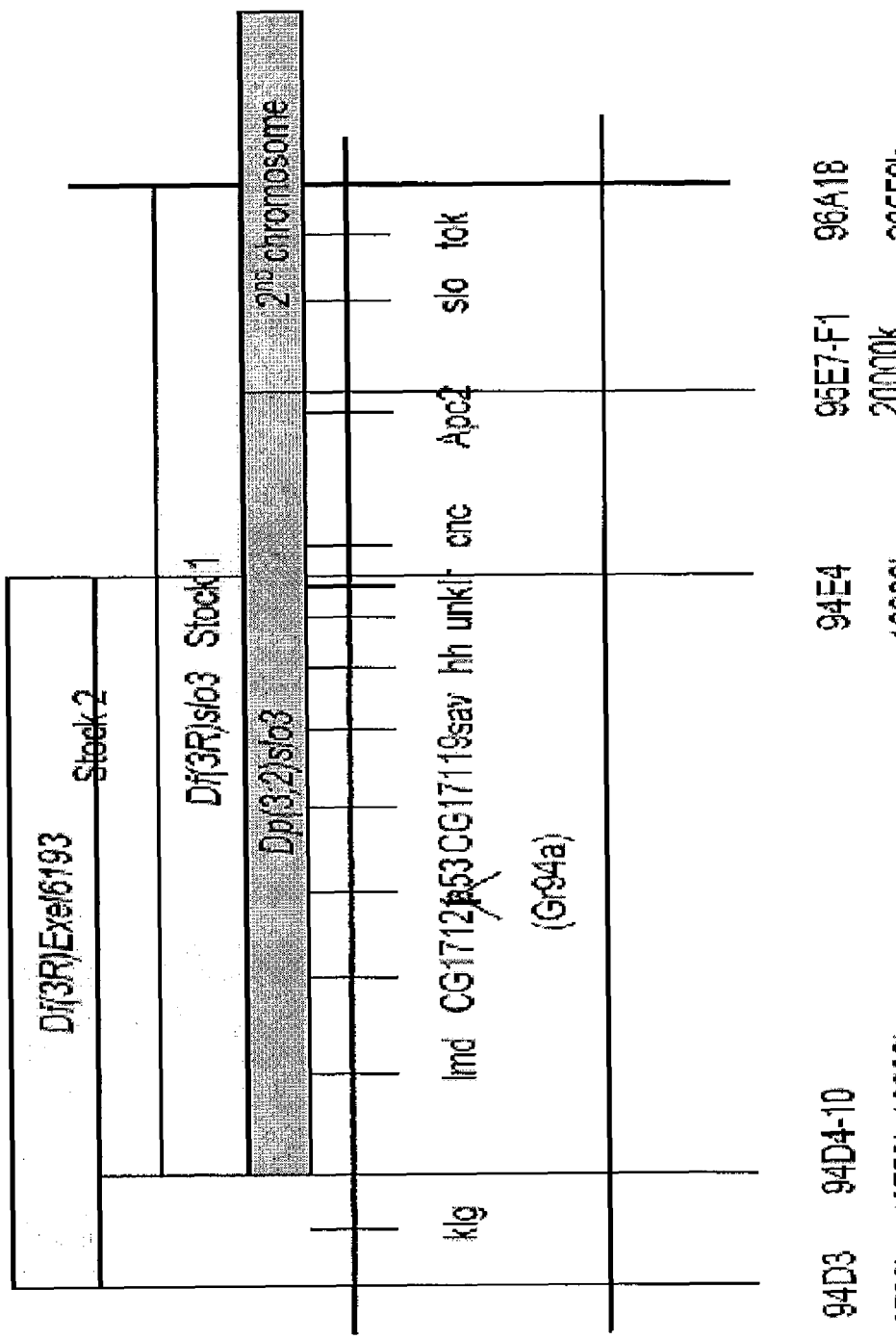
Figure 8A:
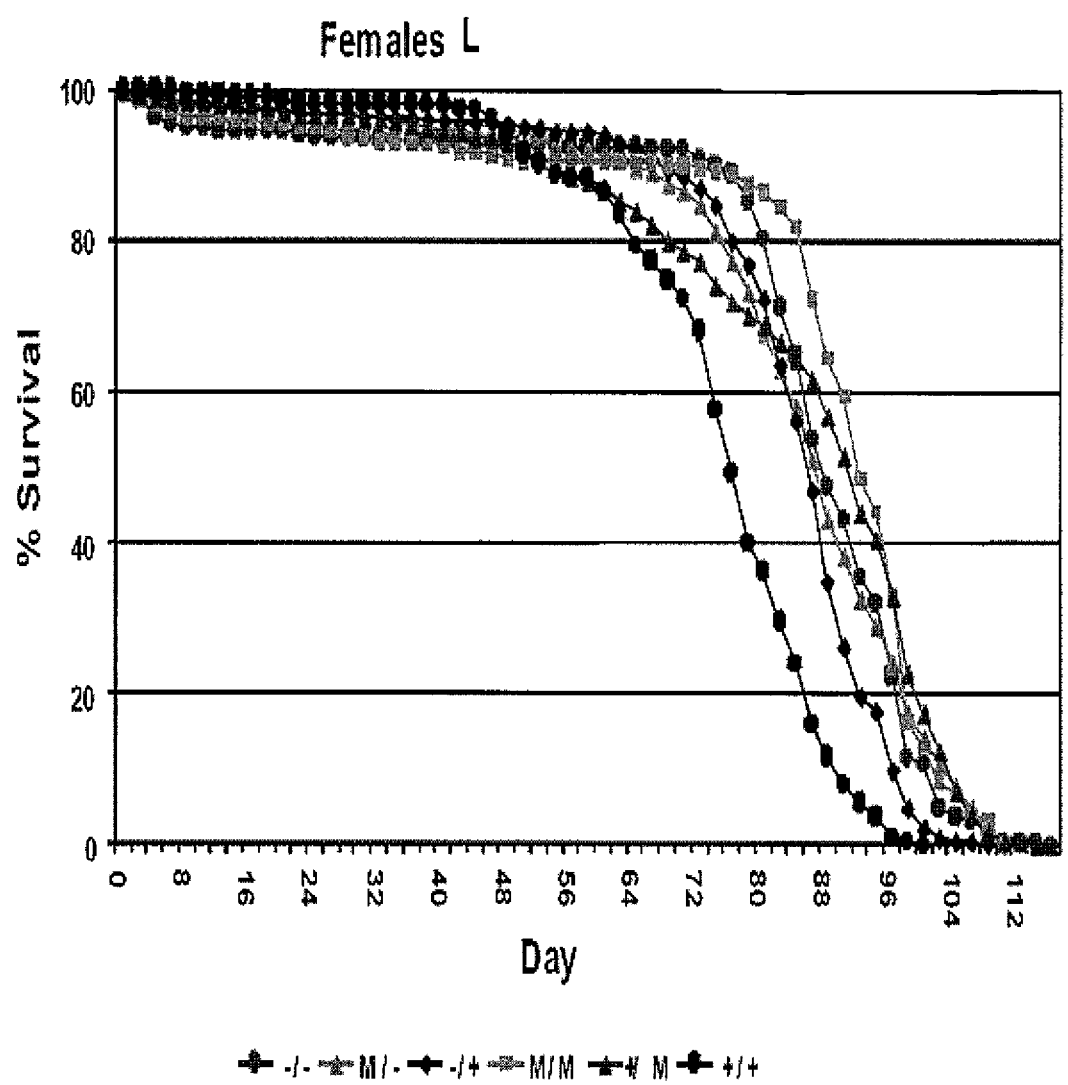
Figure 8B:
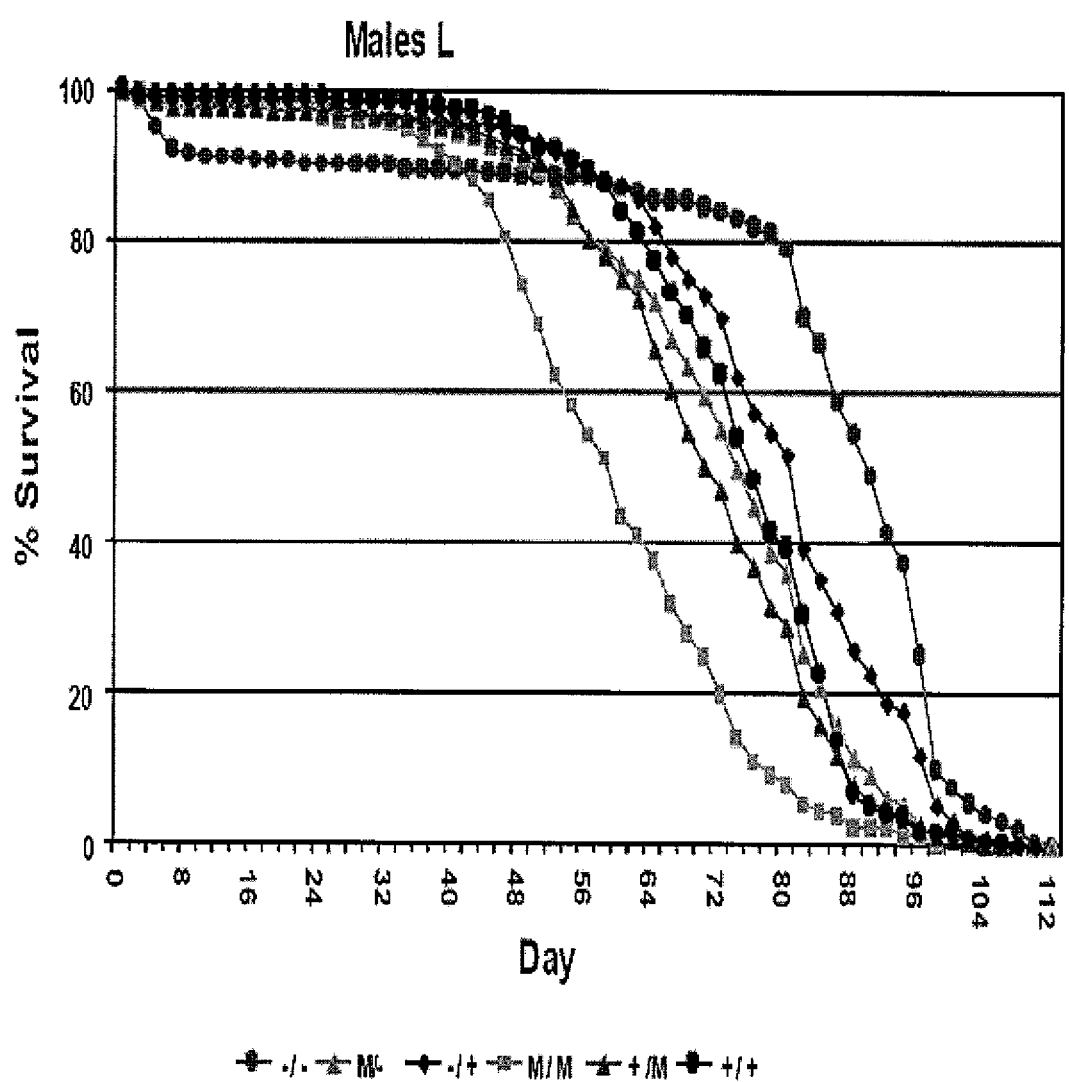
Figure 8C:
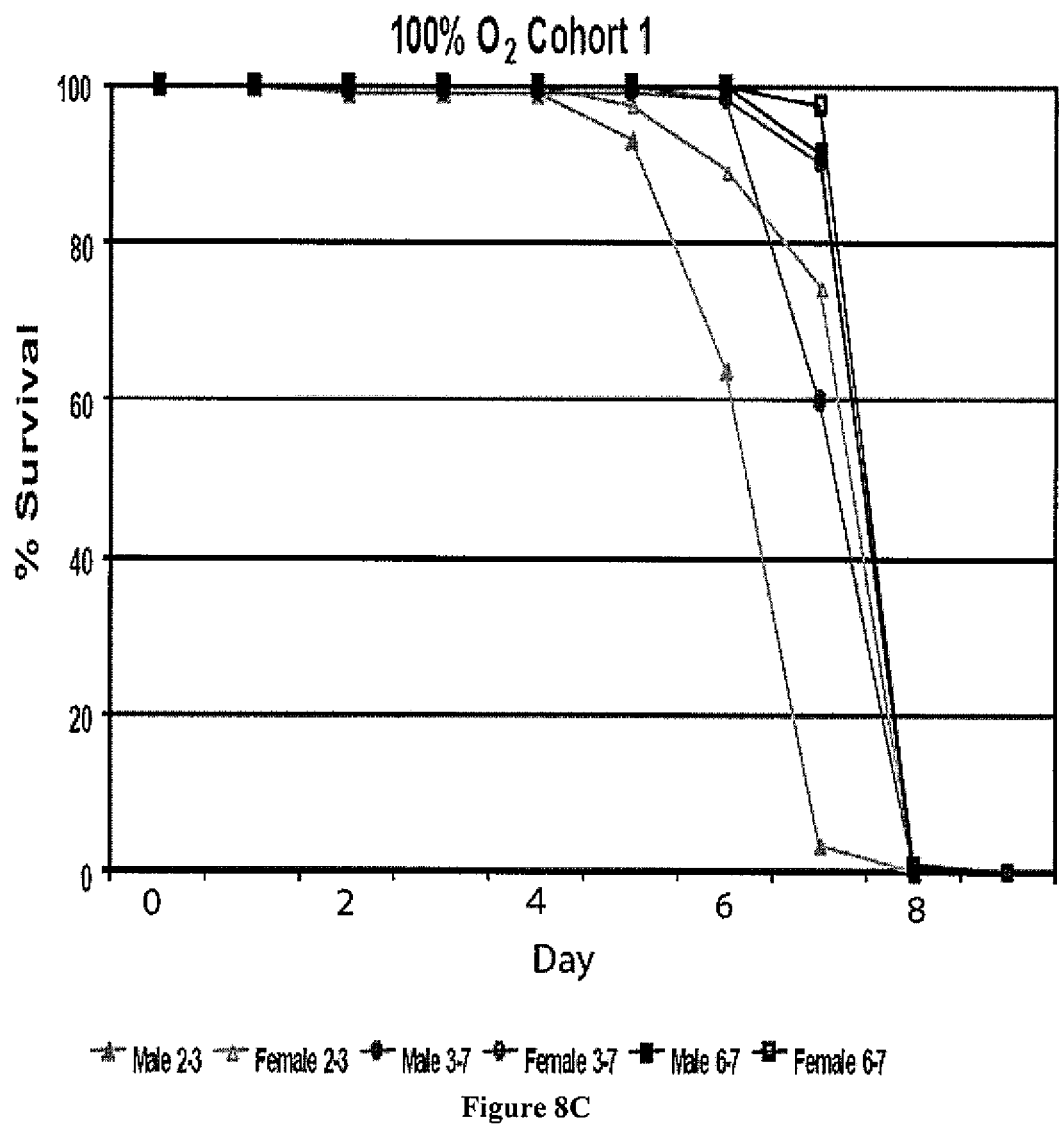
Figures 1, 8D:
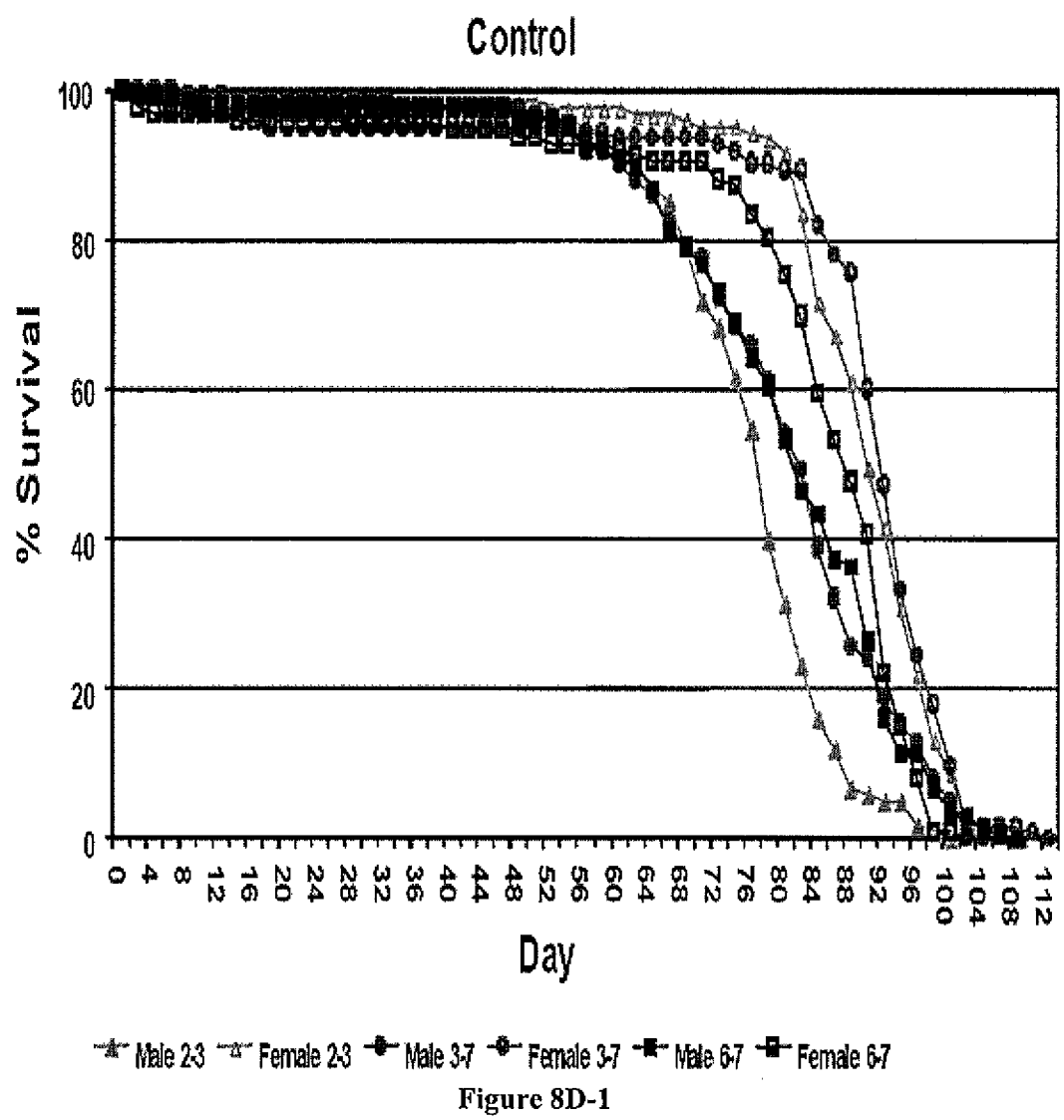
Figures 2, 8D:
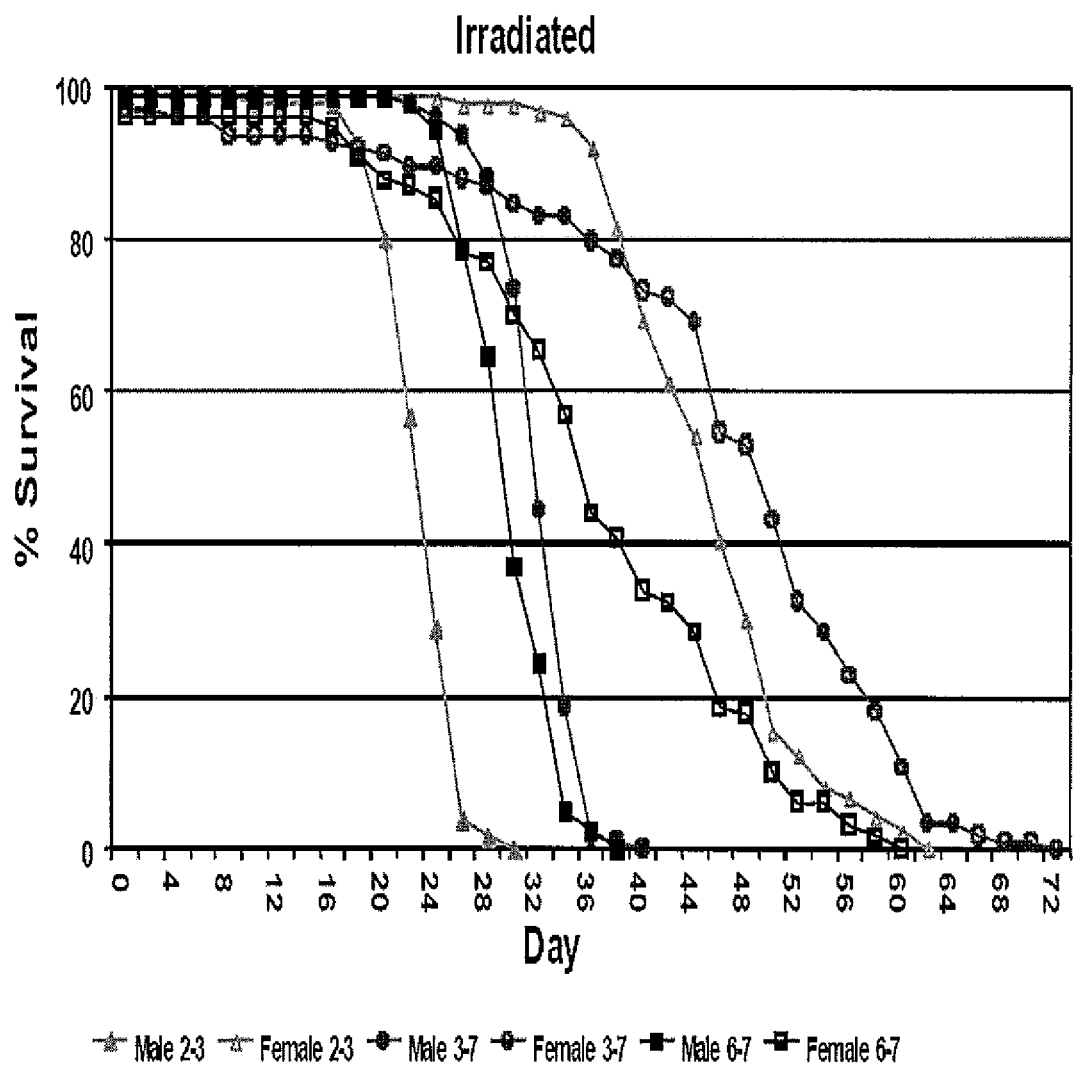

In *Drosophila*, it has been found that both germ-line and somatic sex determination as well as dosage compensation are controlled by the on/off status of the Sxl (Sex lethal) gene (Birchler, Pal-Bhadra et al., 2003; Graham, Penn et al., 2003; Bhadra, Bhadra et al., 2005, the entire content of which are incorporated herein by reference). Sxl-on controls female differentiation and therefore production of this theoretical anti-apoptotic signal (FIG. 3).

How then are mitochondria maintained in the male soma and in sperm precursor cells in the absence of this anti-apoptotic signal? There are two possibilities. The first, and simplest, is maternal contribution of the anti-apoptotic signal. The female would deposit in the egg enough of the anti-apoptotic signal to support male development and spermatogenesis, however the male is incapable of synthesizing the signal. The second possibility is expression of the anti-apoptotic signal (or some compensatory signal) in the male soma and sperm precursor cells—but this requires another pathway for production of the signal and it is not clear why the male would not utilize the same mechanism in the sperm.

The first model seems most consistent with female control over mitochondrial gene function. Perhaps the most intriguing prediction of this model is that to a significant degree male mitochondrial function and life span in flies (and humans) might be determined by the amount of anti-apoptotic signal that he inherits maternally. A number of *Drosophila* gene products are maternally supplied in quantities sufficient to produce and function in the resulting adult animals—as evidenced by maternally-rescued mutations (Table 3). These genes are good candidates for encoding the anti-apoptotic signal and include Sxl itself, the Sxl target gene daughterless and the anti-apoptotic gene Akt1.

Interestingly, *Drosophila* genes with maternally-rescued phenotypes appear enriched on the X chromosome (Table 3), and maternal-effect genes have recently been proposed to participate in sexual conflict in species using ZW sex determination (Miller, Gavrilets et al., 2006).

In humans, there exists a gene that, like *Drosophila* Sxl, is on only in females and that controls dosage compensation—the Xist gene (FIG. 4) (Chow, Yen et al., 2005, the entire content of which is incorporated herein by reference). Xist (or some other human female-specific gene) could control an analogous female-specific anti-apoptotic pathway for mitochondrial maintenance. The human female hormone estrogen has anti-apoptotic properties and could be part of such a mechanism (Nilsen and Brinton, 2004; Vina, Borras et al., 2005), and interestingly the mitochondrial enzyme 17-β-estradiol dehydrogenase shows up in several model organism studies of aging (Landis et al, submitted).

13. Why is Apoptosis the Default State for the Mitochondria?

A variety of genes, both nuclear and mitochondrial, co-exist in the cell to their mutual benefit and thereby optimize their survival, replication and transmission to the next generation. Genetic variation and selection are the basis for evolution as we know it. For variation and selection to occur, genes must give rise to new alleles and these alleles must in turn segregate or otherwise re-assort—i.e., come apart and re-unite in different combinations. From the point of view of any given gene in the cell (Dawkins, 1976), it is beneficial for its partners to vary i.e., leave and return, so that natural selection can act to optimize its set of partners. The genes collaborating in the nucleus have evolved an elegant and rather egalitarian mechanism to accomplish this based on the spindle: independent assortment and recombination. But how do the genes in the nucleus accomplish this segregation relative to the genes in the mitochondria, and vice-versa? Natural selection has acted to create a different mechanism by which the genes in the nucleus and the genes in the mitochondria separate and re-unite over evolutionary time—sex and asymmetric inheritance: In the sense of natural variation and selection, the mitochondrial genes and nuclear genes are together in the female and apart in the male.

Several observations demonstrate that the mitochondria and mitochondrial genomes generally have a shorter functional half-life than does the nucleus or cell. First, mitochondria are known to actively turn over in many non-dividing cell types (Spees, Olson et al., 2006). Second, as discussed above, the male germ line initially has cells with abundant functional mitochondria, but ultimately gives rise to cells where the mitochondria are absent or non-functional in terms of inheritance. Clearly modern-day mitochondria are dependent upon the nucleus and cellular milieu for growth and replication, but why should mitochondrial apoptosis (self-destruction) be the default state?

From the point of view of the eukaryotic female cell this may be the simplest way to control mitochondrial abundance and gene inheritance—to engineer the mitochondria with an apoptotic mechanism and ration the antidote. In other words, engineering the mitochondria with a shorter half—life and rationing a survival/growth factor. From the point of view of the mitochondria, this may be the simplest way to accomplish two things: first to be maintained in the cell, and second, to be maintained in the cell as an entity separate from the nucleus.

In general, the current state of affairs can be thought of in terms of game theory as an evolutionarily stable strategy (ESS) for the cooperation of the nucleus and the mitochondria (Nowak and Sigmund, 2004; Burt and Trivers, 2006). As is typical of many game-theory strategies for cooperation, one party (in this case the mitochondria) must sometimes leave or defect. What does leaving or defecting amount to in a biological context? Cellular apoptosis, organellar apoptosis, and asymmetric segregation (a failure to be inherited) seem to be likely mechanisms. With regard to inheritance and function, the mitochondria defects in the male.

When the mitochondria invaded the eukaryotic cell (Gray, Burger et al., 1999; Lang, Gray et al., 1999; Searcy, 2003; Timmis, Ayliffe et al., 2004) it created competition between the nucleus and the mitochondria for inheritance, as well as the potential opportunity for mutually beneficial cooperation (FIG. 5). This sets up a situation similar to a "prisoner's dilemma" in game theory (Nowak and Sigmund, 2004; Burt and Trivers, 2006): If the mitochondria always stays with the nucleus the nucleus will absorb the mitochondria and it will cease to be a separate, multi-copy entity. However, if the mitochondria sometimes leaves—i.e., is lost at some finite rate, either by segregation or apoptosis—the nucleus must actively maintain the mitochondria and this allows it to remain an independent entity. In other words, shorter half-life and asymmetric inheritance for the mitochondria represents an evolutionarily stable strategy (ESS) for the co-operation of the nucleus and mitochondria. The only way the mitochondria can be maintained as a separate entity from the nucleus is to have a finite half-life, i.e., be lost at some rate by segregation or apoptosis. This is the same thing as asymmetric segregation: there are two states of the nucleus, with functional mitochondria (e.g., egg) and without (e.g., sperm). This requires the existence (or drives the evolution) of two states in the nucleus-one state that prevents mitochondria loss and one that does not (e.g., Switch Gene (SG)-on/off). In other words, the powerful selective advantage of the mitochondria creates the sex determination gene and chromosome in the nucleus: A successful and continued infection by the mitochondria would require the existence of SG-on/off to establish and maintain the ESS. In this model any asymmetrically inherited gene(s) with a large selective advantage (like the mitochondrial genome) would define the female (more fit), and the male (less fit).

It is possible to see X chromosome hypermutation in the male as an attempt by the male to either activate or destroy the gene (SG) that limits mitochondrial gene inheritance to the female, a process that might in turn be hypothesized to drive the dynamic deterioration and evolution of sex chromosomes (Charlesworth and Charlesworth, 2005; Graves, 2006). Consistent with this idea, the gene at the top of the sex determination pathway appears to mutate rapidly and change in identity often through evolution (Graham, Penn et al., 2003) (Sxl in *Drosophila melanogaster*, tra in *Ceratitis capitata*, and Xist in humans), and these genes are predicted to exhibit antagonistic pleiotropy and function in regulating life span. A change in the identity of the SG might be a handy mechanism for speciation.

Interesting parallels can be seen between this model and what happens when a largely detrimental genome such as the intracellular parasite *Wolbachia pipientis* infects the *Drosophila* egg cytoplasm (Fry and Rand, 2002; Starr and Cline, 2002; Fry, Palmer et al., 2004) —successful infection can be dependent on the particular allele of Sxl.

14. Asymmetric Segregation of Genes as an Evolutionary Force

The general strategy of finite half-life creating asymmetric segregation could be an ancient and important one in evolution. Consider a primordial gene A that encodes a replicator molecule that replicates gene A (FIG. 6). A and its product might be floating around free in the primordial soup, or be surrounded by the membrane of a proto-cell (Szathmary, 2000; Hogeweg and Takeuchi, 2003; Scheuring, Czaran et al., 2003; Line, 2005). Another gene B could cooperate with and be linked to A (either covalently or by inclusion in the same cell) but to be selected for and maintained A+B must have greater fitness than A alone, such as by encoding a better replicator. It is easy to see how this might work, but if A and B are always linked together they are not separate genes. How can A and B cooperate yet still exist and evolve as separate entities? As mentioned above, for evolution to occur, a genes' partner(s) must somehow vary as a function of time. One simple way for this to be accomplished is if gene B has a shorter half-life than A (i.e., is lost at some finite rate, i.e., ages). By definition, this creates two states for A: A by itself and A+B.

In summary, a beneficial new gene with a shorter half-life by definition creates asymmetric segregation, and asymmetric segregation by definition creates increased complexity of the system. This ESS model suggests that finite half-life (aging or senescence) is the consequence of natural selection for increased complexity (evolution).

Is there any evidence that genes exist in such an ESS today? It is interesting to note in this regard that the gene sequences with the longest half-lives (i.e., most conserved through evolution) include many polymerases, translation components, motor molecules and transporters—perhaps representing the ancient master replicators. In contrast, the most rapidly evolving genes include ones involved in reproduction, especially male gametogenesis (Good and Nachman, 2005; Nielsen, Bustamante et al., 2005; Richards, Liu et al., 2005). It also seems possible that the DNA-end replication problem (Olovnikov, 1973; Ohki, Tsurimoto et al., 2001) represents a strategy by which the (ancient) DNA polymerase gene ensures that more distal genes on the chromosome have a shorter half-life.

15. The Mitochondrial Apple

In Biblical history, the snake tempts Eve into eating an apple from the forbidden tree of knowledge. Adam and Eve become aware of their nakedness and in retribution God casts them out of the Garden of Eden forever. When the proto-eukaryotic female ingested the highly beneficial mitochondrial genome and maintained it through asymmetric inheritance, she introduced an asymmetry in fitness between the sexes. The resultant antagonistic pleiotropy of gene function between male and female helped drive the evolution of multicellularity and ultimately self-awareness, but came at a cost of aging phenotypes and limited life span.

Models for the co-evolution of sex and asymmetric inheritance are not new, and include fascinating ones where sperm dynamics represent the vestiges of the movement of the mitochondria's *Rickettsia*-like ancestor from one cell to another (Fabrizio, Hime et al., 1998; Bazinet and Rollins, 2003; Bazinet, 2004). Space considerations preclude discussion of prokaryotic toxin/antitoxin systems (Gerdes, Christensen et al., 2005) which seem eerily similar to the systems for mitochondrial inheritance discussed here, or Honeybees—where expression of mitochondrial genes distinguishes the long-lived Queen from the genetically identical short-lived workers (Corona, Hughes et al., 2005).

Apoptotic cell death is implicated in many human aging-related diseases, such as Alzheimer's disease and Parkinson's disease. However, apoptosis has sometimes been discounted as a likely species-general mechanism of aging based on the lack of detectable apoptotic cell death in old *C. elegans* and the lack of effect of critical apoptosis genes such as ced-3 caspase on *C. elegans* life span (Garigan, Hsu et al., 2002; Herndon, Schmeissner et al., 2002). The current results suggest that those conclusions should be reexamined in light of the fact that *C. elegans* is a hermaphrodite, and predict that apoptosis might limit life span in *C. elegans* males.

It has generally been assumed that mitochondria and oxidative stress are consistently implicated in life span regulation (Fridovich, 2004) implies that oxidative damage is inherently more toxic than the many other damages and challenges cells suffer over time. However, in light of the discovery of the present invention, the involvement of mitochondria and oxidative stress in life span regulation may be explained by the asymmetric inherited of mitochondrial genes which renders mitochondrial functions more prone to antagonistic pleiotropy.

In view of the above, the model of the present invention provides a basis for devising method for modulating aging and/or treating aging related diseases such as Alzheimer's disease, Parkinson's disease, cancer, Huntington's diseases, or any other aging related diseases known in the art.

Additionally, anti-aging pharmaceutical products may also be identified using methods of the present invention.

Last but not least, methods for in vitro evolution of genes or products, diagnostic tools, and tools for performing aging related research may also be advantageously devised.

Accordingly, in one aspect, embodiments of the present invention provide a method for identifying a human gene sequence useful for developing an anti-aging pharmaceutical product or a pharmaceutical product for treating aging related disease, comprising obtaining Xist gene sequences of a population of long-living individuals; and correlating the Xist gene sequences to sex and age dependent characteristics, wherein sequences having high correlation to sex and old-age define template sequences for designing said pharmaceutical products.

It is an unexpected discovery of the present invention that the Xist gene plays a role in regulating the life-span of an individual. Accordingly, an agent that is capable of activating the Xist gene in an individual may be used as a therapeutic to prolong life or to treat aging related diseases. By correlating variations in the gene sequence to a population of long-living individuals, sequences or subsequences of the gene that are correlated to long life span may be identified.

In a preferred embodiment, the population for performing such a correlation analysis should consists of only individuals of age 80 and above, more preferably 100 and above. Other characteristics may also be selected for correlation analysis. Exemplary characteristics may include, but not limited to disease history, behavioral characteristics, or any other characteristics of interest.

Exemplary aging related diseases may include, but not limited to Alzheimer's disease, Parkinson's disease, cancer, Huntington's disease, or any combinations thereof.

Exemplary native Xist gene sequence that may be used for the correlation analysis is as provided in SEQ ID: 3, or any other fragments thereof, alternate splicing products thereof, or any combinations thereof.

In another aspect, embodiments of the present invention provide a method for manipulating the aging process or treating an aging related disease, comprising: administering a pharmaceutically active composition comprising a Xist RNA, alternate splice forms of the RNA, a fragment thereof, or an analog thereof to a subject.a method in accordance with the present invention for treating aging in a subject generally comprises the steps of administering to a subject an agent capable of activating the expression of Xist gene in the subject.

Exemplary means of administering the pharmaceutically active agent may include, but not limited to direct inject, oral ingestion, or by way of a biological delivery vector. Exemplary vectors may be any suitable vector generally known in the art so long as it is capable of delivering the Xist gene product to a host cell.

In yet another aspect, embodiments of the present invention provides a method for treating aging or aging related diseases, comprising administering to a subject an agent capable of activating the expression of Xist gene in the subject.

Exemplary agents capable of activating the expression of the Xist gene may include, but not limited to a nucleic acid, a polypeptide, a protein, a nucleic acid mimetic, a small organic molecule, or a combination thereof. Given a Xist gene sequence (as exemplified by SEQ ID: 3), the design of an agent capable of activating the gene may be achieved by molecular biology techniques commonly known in the art. In one preferred embodiment, the agent is 5-azacytadine or an analog thereof.

In yet another aspect, embodiments of the present invention provides a method for in vivo evolution of genes to obtain genes having desired properties, comprising: selecting a starting set of genes with high rates sequence variation, wherein at least one gene is capable of cleaving itself at a predetermined rate; replicating the genes via in vivo replication to evolve the genes; and testing the properties of the genes at predetermined intervals for the desired property.

To implement finite half-life of genes for in vivo evolution of genes with desired properties, the staring gene would be engineered to both be able to replicate itself with an significant rate of sequence variation, and to also have short half-life by being able to cleave itself at a finite rate. Alternatively the substance of which the gene is composed would be designed to have a short half-life due to dissolving in the aqueous media, or by rapid thermal denaturation. The gene may be composed of RNA, DNA, protein, sugar/carbohydrate, lipid, or some modification or combination of those compounds. One typical example is a catalytic RNA that can both replicate itself and cleave RNA and that contains its own recognition site for cleavage. Another example is a protein that can replicate itself, alone or in combination with other proteins, and that can also cleave protein and that contains its own recognition site for cleavage.

In yet another aspect, embodiments of the present invention provides a microarray useful for studying genetic regulation of aging, comprising: a plurality of nucleic acid sequences wherein at least one sequence comprises a Xist gene sequence, a Sxl gene sequence, or a mutant thereof.

General methods for manufacturing of microarrays are known in the art. Microarrays according to embodiments of the present invention may contain specific Xist gene sequences or Sxl sequences identified from sex/age population analysis such as described in the methods above. The microarrays may be useful both as a research tool and a clinical diagnostic tool.

To assay the specific sequence and expression pattern of various splice forms of Xist in individuals, sub-sections of Xist gene sequences can be affixed to a solid support, such as a glass slide or other material, in the form of DNA or oligonucleotide, to generate a micro-array. DNA and/or RNA samples obtained from individual patients can then be chemically labeled and hybridized to the micro-array to allow for rapid screening and identification of the individuals Xist gene sequence and expression pattern.

Patient samples might be from blood or serum or other tissues. This should allow for rapid assessment of the individuals aging rate and predisposition for specific aging-related diseases.

In yet another exemplary embodiment, there is provided A kit useful for studying genetic regulation of aging, comprising: at least one vector comprising a Xist gene sequence, a Sxl gene sequence, or a mutant thereof. Similar to the microarrays, the kit may comprise specific Xist sequences or Sxl sequences identified from sex/age population analysis. Furthermore, kits according to embodiments of the present invention may also be in the form of a library of vectors containing Xist gene sequence or Sxl gene sequences.

To further illustrate the present invention, the following specific examples are provided.

EXAMPLES

Example 1

*Drosophila Melanogaster* p53 Acts to Limit Life Span

The p53 gene encodes a transcription factor that regulates apoptosis and metabolism and is mutated in the majority of human cancers. *Drosophila* contains a single p53 gene with conserved structure, and expression of a dominant-negative p53 isoform in nervous tissue has been shown to extend fly life span. Here analysis of multiple *Drosophila* p53 mutant genotypes and conditional over-expression of wild-type and dominant-mutant transgenes revealed that p53 limits the life span of both male and female flies, but acts to do so preferentially during male development and in female adults. In contrast, wild-type p53 function favored survival of both male and female adults under stress conditions. Strikingly, over-expression of p53 or baculovirus p35 during development was preferentially toxic to males, but in females produced a sub-set of flies with increased longevity. Taken together, the data demonstrate that *Drosophila* p53 has developmental stage-specific and sex-specific effects on adult life span indicative of sexually antagonistic pleiotropy, and support a model in which sexual selection maintains the aging phenotype in both *Drosophila* and human populations.

Experiments

To test how p53 might affect *Drosophila* life span, flies that had a deletion of the endogenous p53 gene were examined (FIG. 7). Various trans-heterozygous p53 wild-type and mutant allele combinations were assayed for life span simultaneously to help control for genetic background effects. Experiments were done using a dextrose-containing food that yields long life spans (L cohort), as well as on a food rich in yeast and sugar that yields shorter life spans (W cohort). In both experiments null mutation (−/−) of the p53 gene increased male life span by about 30% relative to wild-type (+/+) controls, while heterozygous (+/−) male flies had a smaller but significant increase (FIG. 8). Life span was also increased in female p53 null mutant (−/−) and heterozygous (+/−) flies relative to wild-type controls (+/+), however the effect was less dramatic on rich food. Taken together these data suggest that p53 acts at some point in the life cycle to limit the adult life span of both male and female flies, with greater effects typically observed in males. In contrast, p53 gene function was found to favor the survival of both male and female adult flies subjected to conditions of oxidative stress (100% oxygen atmosphere) (FIG. 8C) and ionizing radiation (FIG. 2D). This is consistent with previous reports that wild type p53 gene function can protect *Drosophila* tissues from ionizing radiation and UV toxicity during development.

To control for possible maternal effects and X chromosome effects, several life span assays were repeated with the crosses done in both directions simultaneously, i.e., varying which strain serves as mother or father for the cross. An increase in life span of p53 null mutant (−/−) flies relative to wild-type (+/+) controls was obtained in female progeny regardless of cross direction, thereby ruling out a primary effect of maternal genotype. Strikingly the p53P mutation is a P element insertion predicted to disrupt expression of only the A isoform of p53 (FIG. 7), and was associated with increased life span only in females.

The p53 protein functions as a quatramer with various protein domains mediating multimerization, DNA binding and transcriptional transactivation. Mutant forms of p53 lacking function of a particular domain can have powerful dose-dependent effects that can either promote or antagonize the activity of wild-type p53 referred to here as dominant mutations. Several *Drosophila* p53 dominant mutations (M) were examined and found to have complex effects on adult life span, depending upon the particular allele, whether or not a wild-type copy of p53 was present in the background, as well as the food composition. Some of the variability in life span across genotypes is expected to result from differences in genetic background. However, when considered as a group the dominant mutations tended to decrease life span in males, and to increase life span in females (FIG. 8 A, B). Since the dominant mutations should generally antagonize wild type p53 functions, these results are consistent with the results obtained above suggesting that p53 acts in during male development and in adult females to limit adult fly life span.

To confirm the effects of p53 on fly life span, the conditional transgenic system Geneswitch (Ford et al. 2007, the entire content of which is incorporated herein by reference) was used to over-express both wild-type and mutant forms of p53. Over-expression of wild-type p53 in adult flies had a strong negative effect on life span in females, but not males (FIG. 9A). In contrast, over-expression of dominant mutant p53 did not have a negative effect, and in fact female life span tended to be increased (FIG. 9 C, D). This is consistent with the previous report that over-expression of the p53 dominant allele using a non-condition system increases adult female life span. Similar effects on adult female life span were obtained using the FLP-out conditional system to over-express wild-type and dominant p53 transgenes. Taken together, the over-expression data suggest that p53 acts in adult females to limit life span, with less effect observed in adult males. One possible mechanism by which p53 might act in adults to preferentially limit adult female life span might be by stimulating insulin/IGF-1-like signaling (IIS), since IIS appears to preferentially limit life span in females of *Drosophila* and other species. Another possibility might be that p53 interacts with the dietary restriction (DR) mechanism, since DR preferentially increases female life span in *Drosophila* and other species. Consistent with an interaction between p53 genotype and DR pathway, here the effect of dominant p53 mutations was markedly different in females depending on food composition.

Almost opposite effects on adult life span were observed when p53 transgenes were expressed during larval development. Over-expression of wild-type p53 during development was toxic to males and limited their subsequent adult life span, but had less effect on females (FIG. 9). Strikingly, titration of wild-type p53 over-expression during female development produced some adult females with unusually long life spans, demonstrating that p53 can sometimes act during female development to promote the life span of the subsequent adults. Taken together the data suggest that during development p53 acts preferentially in males to limit the survival of the subsequent adults.

One mechanism by which p53 might act during development to affect subsequent adult life span is by regulating apoptotic pathways. As such the caspase inhibitor baculovirus p35 was tested to determine if any similar effects on life span might be observed. When expressed during development the baculovirus p35 gene was found to be preferentially toxic to males and to dramatically limit subsequent adult male life span, similar to the phenotypes observed with wild-type p53 above (FIG. 9). Moreover, over-expression of baculovirus p35 during female development resulted in a bi-phasic survival curve and a sub-population of female adults with increased life span, again analogous to the results obtained above with p53. Therefore the over-expression phenotypes of p53 and the caspase inhibitor baculovirus p35 during development are similar, suggesting that it may be an apoptotic pathway through which these genes act during development to affect subsequent adult longevity in a sex-specific manner.

In these experiments the p53 gene was found to favor the survival of both sexes under oxidative stress conditions, yet to act at different developmental stages to limit the life span of both sexes under normal conditions. The female-specific longevity effect of the P element insertion in the B-variant suggests that this isoform may preferentially limit life span in females. It will be of interest in the future to determine if the A variant might correspondingly act more to limit male life span, and to determine if these variants display any corresponding sex-specificity in expression patterns. Taken together the data are consistent with a sexual antagonistic pleiotropy model in which p53 functions are maintained by positive selection for survival benefit in each sex, despite having negative effects at another stage of the life cycle in the other sex.

Methods and Materials

*Drosophila* culture and life span assays were performed as previously described (Ford et al., 2007). *Drosophila* culture media for the W cohort life spans used an older recipe including molasses, while all other experiments used a newer recipe containing dextrose (data not shown).

FLP-out strains, heat pulse protocols and life span assays are as previously described (Struhl, 1993; Basler, 1994; Sun, 2004; Sun, 2002, the entire contents of which are incorporated herein by reference). Geneswitch strains and protocols are as previously described (Osterwalder, 2001; Roman, 2001; Ford, 2007). Fat Body (FB) expression driver genotype w; P{Switch1}106 (S1-106), and panneural-expression (ELAV) driver genotype y w; +, P{ELA V-GeneSwitch} (GSG301). RU486 (Mifepristone, Sigma) was fed to adult flies or developing larvae by adjusting the food to 500µ/M final concentration. In certain experiments RU486 concentrations were titrated as indicated. All ages are expressed as days from eclosion at 25° C. Wild-type and DN p53 transgene stocks were obtained from Michael Brodsky (Brodsky, 2000) and Bloomington *Drosophila* Stock Center. p53 mutant strains were obtained from Kent Golic and Bloomington *Drosophila* Stock Center (Xie, 2004). P{GUS-p53}CDM26, p53 WT, chromosome 2 (WT). P{GUS-p53.Ct}AF51, C-terminal fragment AA285-385, chromosome 2 (DN). P{GUSp53.Ct}B440, C-terminal fragment AA285-385, chromosome 3 (DN). P{GUSp53.259H}, AA substitution, chromosome 3 (DN). Df(3R)slo3 is deletion of entire p53 gene (Null). Df(3R)Exel, P{XP-U}Exel is deletion of entire p53 gene (Null). p53-[5A-1-4] is 3.3 kb internal deletion (DN). p53[11-1B-1] point mutation introduces stop codon at nucleotide residue 211, yields 70AA truncated protein (DN). p53[1] is the [5A-1-4] 3.3 kb internal deletion in a different genetic background (DN). Varying genotypes were generated by appropriate crosses to (double) balancer stocks obtained from Bloomington *Drosophila* Stock Center.

FLP-out heat stress protocol. Age-synchronized cohorts of females of each genotype were collected and maintained at 25° C. in groups of 20 flies per vial. The females were subjected to heat shock at 37° C. for 90 min for either one day or two consecutive days at age 5-6 days, as indicated. The females were combined with 5 young male flies (to stimulate egg production) and transferred to fresh fly food vials every other day and maintained at 25° C.

Analysis

Maximum life span was estimated as the number of days until 90% of the cohort had died. A non-parametric Welch t-test was used to compare the mean life span data between the different groups of p53 deletion genotypes (data not shown). Differences in the shape of survival functions and patterns of mortality were analyzed using a statistical framework described by Pletcher. Individual life spans of p53 deletion genotypes were fitted to Gompertz model: with probability density function $$f(x) = \lambda \exp\left\{\gamma t - \frac{\lambda}{\gamma}[\exp(\gamma t) - 1]\right\}$$

The parameter lambda represents demographic frailty or baseline mortality and gamma represents the rate of change in mortality with age, the demographic rate of aging. To compare parameters among genotypes, variables based on the Gompertz model were estimated by maximum likelihood. To compare survivals curves, a likelihood ratio test was used: The likelihood $L_0$ under the assumption of a common lifetime distribution is compared to the likelihood $L_1$ when two different Gompertz curves are assured. Under the hypothesis of common lifetime distribution $-2 \log L_0/L_1$ is approximately $chi^2$-distributed with 2 degrees of freedom. Following this procedure, most p53 deletion genotypes were found to differ from (w/+; +/+) controls (data not shown).

Unpaired, two-sided t-tests were used to compare mean life spans between control and treated fly cohorts. One- and two-factor ANOVAs and Welch's t-tests were used to ascertain whether p53 expression significantly affects life span and fecundity (data not shown).

For FLP-out experiments mean life spans for females were compared between control and heat pulsed populations using a two-factor fixed-effects ANOVA model with main effects of genotype and heat pulse. FLP-out over-expression of wild-type p53 had a significant negative effect on mean life span (data not shown). To address FLP-out strain effects on estimated maximum life span, nonparametric 95% confidence intervals (CI) were calculated for 90% life span for flies in the control (noheat shock) cohorts for each strain. Wild type p53 had [70, 78] 95% CI, AF51 had [78, 80], B440-[80, 82], 259H-[79, 80] and control CI was found to be [74, 76]. Each dominant negative strain (AF51, B440, 259H) exhibited CIs that do not overlap with CI of control 90% survival age. The 90% survival age is significantly different in each dominant negative strain from control (p-value<0.005) using a permutation test (data not shown).

Example 2

Molecular Misreading in *Drosophila melanogaster*

Molecular Misreading (MM) is the inaccurate conversion of genomic information into aberrant proteins. For example, when RNA polymerase II transcribes a GAGAG motif, it sometimes synthesizes RNA with a two-base deletion. If the deletion occurs in a coding region, translation can result in production of misframed proteins. Certain misframed proteins increase in abundance during mammalian aging, and misframed versions of human amyloid precursor protein (hApp) and ubiquitin (hUbb) accumulate in neurodegenerative disease tissue. Here cDNA clones encoding wild-type hApp and hUbb as well as frame-shifted versions (hUbb$^{+1}$ and hApp$^{+1}$) were expressed in transgenic *Drosophila* using the doxycycline-regulated system. Misframed proteins were abundantly produced, both from the transgenes and from endogenous *Drosophila* ubiquitin-encoding genes, and their abundance increased during aging. Over-expression of hUbb was toxic during fly development, yet favored survival when expressed in adults, while hUbb$^{b+1}$ did not have these effects. The data suggest that MM is an evolutionarily conserved aspect of gene expression and aging, with specific phenotypic consequences.

Results

1. Generation and Conditional Expression of Transgenic Constructs

To determine if MM could be studied in *Drosophila*, cDNA clones encoding wild-type and frame-shifted versions of the human proteins, hUbb and hApp, were expressed in *Drosophila* using the conditional doxycycline(DOX)-regulated system ("Tet-on") (Bieschke et al. 1998; Ford et al. 2007). In the DOX-regulated system, the control and experimental animals have identical genetic backgrounds, and transgene expression is induced in larvae or adults by feeding the drug DOX. In this way any possible toxic effects of the RNAs or proteins could be avoided since expression should occur only in the presence of DOX. Human cDNAs encoding wild-type proteins, and cDNAs engineered with the appropriate dinucleotide deletions adjacent to or within the GAGAG motif were cloned downstream of the DOX-regulated promoter (FIG. 10). These sequences were introduced into *Drosophila* using P element mediated transformation and multiple independent transgenic strains were generated for each construct. In all the experiments presented, the strains homozygous for the transgenic target constructs were crossed to the rtTA(3)E2 driver strain (or other driver strains, as indicated), to generate hybrid progeny containing both constructs. In the rtTA construct the powerful, tissue-general cytoplasmic actin (actin5C) promoter drives expression of the artificial transcription factor rtTA. Upon DOX feeding the rtTA protein undergoes a conformation change and binds to specific sequences (called TetO) in the target construct, thereby activating transgene expression in all tissues except for the germ-line. For controls, the rtTA(3)E2 line was crossed to Oregon-R wild type flies to generate hybrid progeny containing only the rtTA(3)E2 driver construct and no target construct, and for simplicity these controls are referred to hereafter as "Or-R control" flies. Conditional (DOXdependent) expression of the transgenes at the level of RNA transcripts was confirmed by Northern blot (FIG. 11A, B).

The human ubiquitin-B gene encodes three direct repeats of ubiquitin protein that is subsequently processed into mature monomers. The GAGAG hotspot for MM is located at the 3' end of each repeat, such that MM causes an almost full-length ubiquitin moiety to be fused with part the next repeat in the +1 frame, thereby creating a altered ubiquitin species with a C-terminal extension of the protein, called Ubb$^{+1}$ (FIG. 10B). The hUbbWT construct contains a single repeat designed to encode a wild-type hUbb monomer. The hUbb$^{+i}$ construct contains two hUbb repeats, with the appropriate dinucleotide deletion engineered at the GAGAG hotspot at the end of the first repeat, thereby constitutively encoding hUbb$^{+1}$. The endogenous *Drosophila* Ubb-encoding genes include a polyubiquitin (Lee et al. 1988) and fusions of Ubb to other coding sequences that are conserved in mammals (Barrio et al. 1994).

2. Western Analysis of HUbbWT Expression

Western blot analysis with a specific antibody was used to assay for expression of the hUbbWT protein in flies. The human and *Drosophila* Ubb proteins are identical in amino acid sequence, so it was expected that antibody raised against hUbb would cross-react with endogenous *Drosophila* protein. Consistent with this expectation, the hUbb antibody recognized a series of protein bands in Or-R control fly extracts, although notably no band was detected at the ~8.5 Kd size calculated for monomeric Ubb (FIG. 11D, and additional data not shown). The lack of a detectable Ubb monomer species is likely due to its rapid ligation to other proteins. A scarce and limiting pool of free Ubb has previously been suggested to explain the low abundance of Ubb monomers relative to multimers in mammalian cell culture studies (Dantuma et al. 2006). The antibody specific for Ubb recognized a series of high-MW proteins in the fly extracts, several of which are indicated by a bracket (FIG. 10D). These species are interpreted to represent endogenous *Drosophila* Ubb ligated to various proteins in the cell. Importantly the abundance of these protein species was not altered by DOX treatment in the Or-R control flies, indicating that DOX itself does not have a detectable effect on ubiquitin expression. A similar pattern of high-molecular-weight species were also present in the extracts of transgenic flies where hUbb was being expressed, and notably the abundance of these species was induced by DOX in each of the three independent transgenic lines tested. These results are consistent with DOX-dependent expression of hUbb from the transgenes that is then rapidly ligated to fly cellular proteins.

3. Western Analysis of Ubb Molecular Misreading

To determine if expression of the misframed (+1) version of the hUbb protein could be detected, antibody specific for hUbb$^{+1}$ was used in Western blot assays. This antibody had been previously characterized and shown to be highly specific for hUbb$^{+1}$ (van Leeuwen et al. 1998). As expected this hUbb$^{+1}$ antibody strongly recognized purified His-tagged hUbb$^{+1}$ protein purified from E. coli cells (FIG. 12A). Strikingly, the Ubb$^{+1}$ antibody also recognized a complex pattern of bands in extracts of Or-R control flies that became more abundant with age, including large amounts of high-MW material, as well as several small species migrating at an apparent MW of <20 Kd (FIG. 12A). These species are interpreted to represent Ubb$^{+1}$ protein produced from the endogenous Drosophila Ubb-encoding genes for two reasons: (i) the almost perfect conservation of ubiquitin gene sequences between the fly and human, including the GAGAG hotspot for MM, means that the endogenous fly gene encodes the same Ubb$^{+1}$ protein as does the human gene, (ii) a similar pattern of DOX-inducible species was produced by both the hUbb$^{+1}$ and hUbbWT transgenes (FIG. 12B-F). The hUbb$^{+1}$ transgene produced a series of bands that cross-reacted with the hUbb$^{+1}$ antibody, both small MW species as well as higher MW species. This pattern of proteins was highly similar to that observed in the Or-R control flies, and also appeared to include several additional species. The calculated size for the Ubb$^{+1}$ monomer is ~11 Kd, and this may correspond to one of the DOX-inducible species migrating at an apparent MW of <20 Kd (indicated with black arrowheads in FIG. 12; estimation of sizes not shown). Ubb$^{+1}$ is itself known to be a target for (poly)ubiquitination by wild-type Ubb (monomeric MW ~8.5 Kd), and notably a DOX-inducible species was present at the MW predicted for Ubb$^{+1}$ ligated to one Ubb moiety (~19.5 Kd, indicated by an open arrowhead), as well Ubb$^{+1}$ ligated to two Ubb proteins (~28 Kd, indicated by asterisk) and Ubb$^{+1}$ ligated to three Ubb proteins (~37 Kd, indicated by double asterisk) (estimation of apparent MW not shown).

Strikingly, the hUbbWT transgenic strains produced a similar series of bands whose abundance was induced by DOX and that cross-reacted with the hUbb$^{+1}$ antibody (FIG. 12B), consistent with MM events. These included apparently the same small MW species described above, as well as a similar series of higher MW species. The abundance of DOX-inducible proteins cross-reacting with the Ubb+1 antibody was observed to increase during aging of flies expressing both the hUbbWT and hUbb$^{+1}$ transgenes (FIG. 12B-F). For example the ~19.5 Kd species was more readily detected in old fly extracts (open arrowhead). Taken together the data suggest that Ubb$^{+1}$ is abundantly produced in transgenic flies from the hUbbWT transgene, consistent with MM, and moreover that the abundance of these misframed hUbb protein species increases with age of the flies. Notably for hUbbWT these MM events cannot be occurring at the GAGAG hotspot (position 219 of the ORF), as it is located downstream of the relevant epitope in this construct (indicated with red asterisk) (FIG. 1B).

4. Western Analysis of hApp Expression and Molecular Misreading

Expression of hAppWT was assayed using a specific antibody (Upstate Cat. #07-667), and no DOX-inducible species could be detected at the calculated size of ~79 Kd, or at other sizes (FIG. 11E), suggesting that the hAppWT protein is not being expressed at a detectable level and/or is not stable. Other studies have reported that hAppWT could be expressed in adult flies and detected by Western blot at an apparent MW of ~110 Kd (Luo et al. 1992; Greeve et al. 2004). One possibility is that hAppWT is being expressed at low levels in the experiments presented here, but is being obscured by a background band such as that running at ~100 Kd (FIG. 11E; indicated with asterisk). However DOX inducible expression of AppWT was also not detected using mouse monoclonal antibody 22c11, which yielded a different pattern of background bands (data not shown). We conclude that AppWT is either not being expressed at a detectable level from this construct in adult male flies, or that the protein is unstable. These hAppWT constructs are indeed being expressed in a DOX-dependent manner at the RNA level, as confirmed by Northern blots (FIG. 11B), and as indicated by the fact that they give rise to hApp$^{+1}$ via apparent MM events, as described next.

To determine if the misframed version of hApp could be detected in flies, Western blots were performed using antibody specific for hApp$^{+1}$. The hApp$^{+1}$ antibody readily detected His-tagged hApp$^{+1}$ protein purified from E. coli cells, as well as highly abundant protein produced in flies transgenic for the hApp$^{+1}$ transgenic construct at the same size, consistent with efficient expression of hApp$^{+1}$ in adult flies (FIG. 13A; indicated by black arrowhead). Notably, both the His-tagged hApp$^{+1}$ and the hApp$^{+1}$ produced in transgenic flies ran in the gel at a position equivalent to an apparent MW of ~58 Kd, which is the reported mobility for hApp$^{+1}$ under these conditions (Hol et al. 2003). This is despite the fact that the calculated MW for the 348 amino acid residue hApp$^{+1}$ protein is ~39 Kd. This unusual retarded mobility in SDS-PAGE gels observed for hApp$^{+1}$ (as well as hApp) has been observed in several previous studies (Weidemann et al. 1989; Hol et al. 2003), and is attributed to the acidic region of the protein between positions 230-260 that contains many glutamate and aspartate residues. In transgenic flies expressing hAppWT transgene, a DOX-inducible band at the same apparent MW of ~58 KD was detected, consistent with MM of the hApp transgene (FIG. 13C, D). It is also interesting to note that there were several species in the Or-R control fly extracts that cross-reacted with hApp$^{+1}$ antibody, including one of a similar size as hApp$^{+1}$ (indicated by an asterisk), and that these species became more apparent with age (FIG. 13B). Despite this background, the fact that the apparently ~58 Kd species was produced in a DOX-inducible manner in two independent hAppWT transgenic strains, but not in the controls, suggests that MM is indeed occurring, and moreover that this hApp$^{+1}$ protein is more readily detected in old flies.

5. Phenotypic Consequences of Expression of HUbbWT and hUbb$^{+1}$

It was next asked if expression of wild-type and +1 versions of hUbb transgenes would have phenotypic consequences for the flies. Over-expression of the highly-expressed hUbbWT (70) transgene during larval development was found to be toxic to flies at the pupal stage, especially in males (FIG. 14), however no significant lethality was associated with the less strongly expressing line hUbbWT(80). To confirm that high-level expression was toxic, a strain was constructed containing two copies of the hUbbWT(118) transgene along with the rtTA(3)E3 ubiquitous driver, and this combination resulted in pupal lethality that was DOX-dependent and completely penetrant. The lethality caused by hUbbWT over-expression was associated with a dramatic disruption of normal pupae structures and large melanotic inclusions indicative of extensive cell death (FIG. 14B). In contrast there was no evidence of pupal lethality when the hUbb$^{+1}$ transgenes were expressed during development, using a variety of drivers. A different result was obtained when the same transgenes were expressed in adult flies. In adults hUbb$^{+1}$ was found to have neutral or slightly negative effects on survival, particularly in male flies (FIG. 14C, D). In contrast, hUbbWT did not have these negative effects and instead was associated with slightly increased life span (FIG. 14E, F). Notably the DOX-dependent life span increase was greater in males, and was greater in the more highly-expressed of the two lines, UbbWT(2)70. Moreover, in the UbbWT(2)70 line a particularly long lifespan was observed even in the absence of DOX, perhaps due to some leaky expression of the transgene. Interestingly, in adult flies over-expression of hUbb was found to cause increased expression of ribosomal protein 49 gene (Rp49) (FIG. 11).

6. A Molecular Misreading GFP Reporter Construct

The conditional DOX-regulated system was also used to express the fluorescent protein GFP (the "Control-GFP" reporter), as well as a reporter construct in which the GFP protein is frame-shifted to encode a non-functional protein (the "MM-GFP" reporter). The MM-GFP reporter contains 3 copies of a GAGAGA hotspot motif such that any MM events should cause production of functional GFP. The Control-GFP construct yielded abundant DOX-dependent expression of GFP throughout the somatic tissues of the fly, as expected. Little or no expression of GFP could be detected with the MM-GFP reporter in young flies or during normal aging (data not shown). However, one possibility is that the expression level was present but simply too low to detect. To address this possibility strains are being generated with multiple copies of the reporter in hopes of increasing the signal. Significant expression of the single-copy MM-GFP reporters could be observed in leg muscle, flight muscle and other tissues when adult flies were challenged with ionizing radiation or 100% oxygen atmosphere. These are strong oxidative stresses that are known to produce acute phenotypes with some similarities to aging. Notably the expression often occurred in isolated patches of tissue, which is reminiscent of the cell-by-cell accumulation of misframed proteins previously observed in the Brattleboro rat magnocellular neurons and human AD disease tissue (de Pril et al. 2006). The data are consistent with MM events, and suggest the reporter may be useful for studying MM in Drosophila longitudinal assays in the future.

Discussion

In these studies wild-type and misframed versions of Ubb and hApp proteins were identified based on their apparent MW in SDS-page gels, co-migration with proteins purified from E. coli, DOX-inducible expression from transgenic constructs, and cross-reactivity with specific antibodies. The Western blot analyses suggested that wild-type and misframed versions of hUbb and misframed hApp proteins were successfully expressed from the transgenes designed to encode these proteins. For both the hUbbWT and hAppWT transgenes there was ample evidence of MM, as these constructs produced DOX-dependent proteins that were recognized by hUbb$^{+1}$ and hApp$^{+1}$ antibodies, respectively. Importantly these hUbb$^{+1}$ and hApp$^{+1}$ species were more readily detected in extracts from old flies, supporting the connection between MM and aging.

It was striking that the hUbb$^{+1}$ antibody recognized a series of abundant protein species in control flies. The fact that several of these species appeared to co-migrate with DOX-inducible bands produced by the hUbb$^{+1}$ transgene (and hUbbWT transgene) supported their identification as containing bona fide Ubb$^{+1}$ protein. This suggests that the endogenous Drosophila Ubb-encoding gene(s) are undergoing MM and producing abundant Ubb+1 protein of various sizes, likely involving cross-linking to other cellular proteins such as Ubb, and moreover that these species become more abundant during aging. Finally, the production of functional GFP protein from the misframed reporter construct suggests that MM events take place in the tissues of flies challenged with oxidative stress.

The ability of the hUbbWT transgene to yield expression of DOX-inducible species that cross react with Ubb+$^1$ antibody is consistent with abundant MM, however these events cannot be occurring at the GAGAG hotspot as it is located only downstream of the relevant epitope in this construct (FIG. 10B). This suggests that one or more other DNA sequence elements located in the 5' end of the wild-type human ubiquitin gene are leading to MM, at least under the conditions assayed here. The nature of these MM events is not clear at this time, as the largest ORF containing the (+1) epitope in the hUbbWT construct does not contain an ATG start codon, and would encode a protein of only 45 amino acid residues (~5 Kd). One interesting possibility is that the DOX-inducible expression of the transgenes is affecting the expression and MM of the endogenous genes and/or the stability and cross-linking of endogenous Ubb proteins.

The faint pattern of endogenous Drosophila species cross-reacting with the hApp$^{+1}$ antibody most likely represents non-specific, cross-reacting proteins, however it is not clear at this time why such cross reactivity is more apparent in old fly extracts. The Drosophila genome contains at least one gene related to hApp, the Appl gene, however it is not obvious how it could encode a cross-reacting epitope or an appropriately sized protein based on its known sequence (Luo et al. 1992). Analysis of fly strains mutant for Appl will be required to test the intriguing possibility that Appl encodes proteins that cross-react with antibodies directed against hApp and hApp$^+$1.

One line of evidence in support of a phenotypic consequence for MM is the effect of the over-expressed genes. While high-level expression of hUbbWT was toxic to developing pupae, over-expression of hUbb$^{+1}$ was not, consistent with different functions for the two proteins. Moreover, hUbbWT appeared to have benefits for survival of adult male flies, while hUbb$^{+1}$ had no benefit, or was slightly toxic. The ability of hUbbWT over-expression to induce ribosomal protein 49 (Rp49) gene expression and favor survival in adult male Drosophila is interesting in light of recent reports that decreased translation can favor longevity in Drosophila (Kapahi et al. 2004), C. elegans (Hansen et al. 2007) and yeast (Chiocchetti et al. 2007). To what extent endogenous Ubb$^{+1}$ may function in normal cell physiology will be an interesting area for future study.

The association of misframed proteins with AD and other disease states and the ability of hUbb$^{+1}$ to inhibit proteosome activity in cultured cells in a dose-dependent manner is consistent with the idea that accumulation of misframed proteins may be detrimental to the aging animal. It will be important to determine if the increased abundance of misframed proteins in old flies is due to increased rates of MM, decreased clearance of the abnormal RNA species by NMD, decreased turnover of the misframed proteins, or some combination of these processes. Consistent with a toxic effect of accumulated protein damage during aging, old flies are more sensitive to proteosome inhibitors (Vernace et al. 2007), and over-expression of certain enzymes implicated in protein repair such as protein carboxyl methyltransferase (Chavous et al. 2001) and methionine sulfoxide reductase A (Ruan et al. 2002) are reported to increase fly life span under appropriate conditions.

The fact that misframed proteins can have toxic effects and appear to increase in abundance during aging in mammals and in flies is consistent with an error catastrophe model, however other explanations exist. For example the apparently abundant expression of Ubb$^{+1}$ in young, wild-type flies may indicate a normal physiological function. Epigenetic regulation of gene expression and phenotypes is increasingly apparent across species (Goldberg et al. 2007). Bistable switches are common and appear to allow phenotypic plasticity on various timescales (Rando and Verstrepen 2007). Interestingly repeated DNA sequence motifs are commonly associated with such epigenetic mechanisms. Stress response genes, particularly oxidative stress response genes such as hsps, are induced during normal aging of flies as well as in human aging-related disease states like AD (Landis et al. 2004; de Pril et al. 2006). The genes encoding ubiquitin are induced in response to stress in flies (Niedzwiecki and Fleming 1993) and mammals (Grillari et al. 2006), and perhaps MM and the conserved GAGAG hotspot motifs represent an evolutionarily conserved epigenetic mechanism by which ubiquitin genes encode alternate proteins with alternate functions expressed in response to certain kinds of stress. For example altered chromatin structure, altered RNA polymerase structure, or low nucleotide concentrations might each be predicted to increase rates of MM. The increased abundance of MM in old flies might therefore represent a compensatory stress response with a benefit for continued function of cells or the animal. Consistent with this idea, in mammalian cells the expression of hUbb$^{+1}$ caused induction of hsp70 and increased resistance to oxidative stress (Hope et al. 2003).

Alternatively, even if MM might serve some conserved beneficial role earlier in the life cycle, such as in response to stress, its chronic activation during aging might be counterproductive. The ability to observe MM in the fly should facilitate the further study of this intriguing phenomenon, including its possible relevance to human aging-related diseases.

Methods and Material

*Drosophila* strains. All *Drosophila melanogaster* strains are as described (Lindsley and Zimm 1992; Bieschke et al. 1998; Landis et al. 2001, the entire contents of which are incorporated herein by reference).

Plasmid construction. Transgenic constructs were generated by PCR amplification of inserts with a PstI site engineered at the 5' end and an EcoRI site at the 3' end, and these fragments were cloned into the unique PstI and EcoRI sites of USC1.0 vector, as previously described (Allikian et al. 2002). All construct sequences were confirmed by sequencing. For hUbbWT construct, PCR products (UBBwt-1, UBBwt-2) were obtained using a pcDNA3 vector containing the UBBwt cDNA as a template. UBBwt-1 was generated using primers Uwt-1F (5' GGCTGCAGGAATTCGATATCAAGCT 3'SEQ ID NO: 4) and Uwt-1 R (5' TTTATTAAGGCACAGTCGAGGCTGATCAGCGA 3'SEQ ID NO: 5). UBBwt-2 was generated using primers Uwt-2F (5' TGCAGGCTGCAGGAAT-TCGATATCAAGCT 3'SEQ ID NO: 6) and Uwt-2R (5' AATTTTTATTAAGGCACAGTCGAGGCTGATCAGCGA 3'SEQ ID NO: 7). Both products were generated using pfu DNA polymerase (Stratagene). Products UBBwt1 and UBBwt$^{-2}$ were boiled for 10 min at 95° C. and cooled to room temperature to generate a reannealed UBBwt gene with a PstI site engineered at the 5' end and an EcoRI site at the 3' end. This fragment was cloned into the PstI and EcoRI sites of USC1.0 (Allikian et al. 2002) to generate the construct USC1.0-UBBwt. The following constructs, USC1.0-UBB$^{+1}$, USC1.0-APPwt, and USC1.0-App$^{+1}$ were generated by using the procedure above. UBB+1-1 was generated using primers U+1-1F (5' GATCCATGCAGATCTTCGTGAAAAC 3'SEQ ID NO: 8) and U+1-1R (5' TTTATTCCAGTGT-GATGGATATCTGCAGAAT 3'SEQ ID NO: 9). UBB+1-2 was generated using primers U+1-2F (5' TGCAGATCCAT-GCAGATCTTCGTGAAAAC 3'SEQ ID NO: 10) and U+1-2R (5' AATTTTTATTCCAGTGTGATGGATATCT-GCAGAAT 3'SEQ ID NO: 11). APPwt-1 was generated using primers Awt-1F (5' GTGCTGGAATTCTGCA-GATATCCAT 3'SEQ ID NO: 12) and Awt-1R (5' TTTATTC-GAGGTCGACGGTATCGATTCTTAA 3'SEQ ID NO: 13). Appwt-2 was generated using primers Awt-2F (5'TGCAGT-GCTGGAATTCTGCAGATATCCAT 3'SEQ ID NO: 14) and Awt-2R (5' AATTTTTATTCGAGGTCGACGGTATC-GATTCTTAA 3'SEQ ID NO: 15). App+1-1 was generated using primers A+1-1F (5' TAGAACTAGTGGATC-CCCCGGGAGA 3'SEQ ID NO: 16) and A+1-1R (5' TTTAT-TCTCGTTGGCTGCTTCCTGTTCCAA 3'SEQ ID NO: 17). App+1-2 was generated using primers A+1-2F (5'TG-CATAGAACTAGTGGATCCCCCGGGAGA 3'SEQ ID NO: 18) and A+1-2R (5' AATTTTTATTCTCGTTGGCTGCT-TCCTGTTCCAA 3'SEQ ID NO: 19). Molecular misreading reporter constructs. PCR products (GFP-1, GFP-2) were obtained using pGreen Pelican plasmid containing the eGFP gene as a template. GFP-1 is generated using primers PG1F (5'GTGAGCAAGGGCGAGGAGCT 3'SEQ iD NO: 20) and PG1R (5'TTACTTGTACAGCTCGTCCA 3'SEQ ID NO: 21). GFP-2 was generated using primers PG2F containing 5'Sac I overhang (5' AGCTC GTGAGCAAGGGCGAG-GAGCT 3'SEq ID NO: 22) and PG2R containing 3'EcoRI overhang (5'AATTTTACTTGTACAGCTCGTCCA 3'SEQ ID NO: 23). Both products were generated using pfu DNA polymerase (Stratagene). Products GFP-1 and GFP-2 are then combined and boiled for 10 min at 95° C. and cooled to room temperature to generate eGFP, a reannealed GFP gene with a Sac I site engineered at the 5' end and an EcoRI site at the 3' end. This fragment is then ligated to MM3X, which is a reannealed synthetic oligos of MMF (5'ATG-GAGAGAGAGAGAGAGAGATC GAGCTC 3'SEQ ID NO: 24) and MMR (5'CGATCTCTCTCTCTCTCTCTCCAT-TGCA 3'SEQ ID NO: 25). MM3X when annealed contains a 5' Pst-I site and a 3' Sac I site which is complementary to the 5'eGFP. MM3X contains three copies of the GAGAGA molecular misreading hotspot. MM3X was ligated to eGFP at 4° overnight and then USC 1.0 was added and ligated at room temperature for 4 hrs to generate the construct USC1.0-MMGFP. T 4 DNA ligase (Promega) is used in all the ligation reactions. A control construct USC1.0-MMCGFP was generated by first ligating eGFP gene to MM3XC, a reannealed synthetic oligos of MMFC (5'ATG-GAGAGAGAGAGAGAGAGAGAGCTC 3'SEQ ID NO: 26) and MMRC (5' CTCTCTCTCT CTCTCTCTCCATTGCA 3'SEQ ID NO: 27). The ligated product was then cloned into PstI and EcoRI sites of USC1.0. P element mediated transformation. Four independent germ-line transformants of the USC1.0-UBBwt construct (hUbbwWT-8, -118, -80 and -70) were generated using standard methods (Rubin and Spradling 1982), using the y-ac-w injection strain (Patton et al. 1992). All four lines integrated onto the 2nd Chromosome. Six independent germ-line transformants were generated for the USC1.0-hUbb$^{+1}$ construct. UBB+1-4, -1, and -11 integrated onto the 2nd chromosome while hUbb[+1]-6, -30, and -19 integrated onto the 3rd chromosome. Southern analysis indicated the presence of single inserts for all the lines. Four independent germ-line transformants were generated for the USC1.0hAppWTconstruct (hAppWT-16, -24, -1, and -20). hAppWT-16, -1 and -20 integrated onto the 2nd chromosome while hAppWT-24 integrated onto the 3rd chromosome. Four independent germ-line transformants were generated for the USC1.0-hApp[+1] construct (hApp[+1]-7, -24, -16 and -30). hApp[+1]-16, and -30 integrated onto the 2nd chromosome while hApp[+1]-7 and -24 integrated onto the 3rd chromosome. Six independent germ-line transformants were generated for the USC1.0-MM-ATG-GFP construct (abbreviated "MM-GFP") (MM-ATG 58A, 46A, 34A, 8A, 46B, and 8B). MM-ATG 58A, 46A, and 34A integrated onto the 3rd chromosome and 46B and 8B integrated onto the 2nd chromosome. Two independent germ-line transformants were generated for USC1.0MMC-ATG-GFP construct ("Control-GFP") (MMC-ATG-GFP-16, -8). Drosophila culture and life span assays. Drosophila were cultured on standard agar/dextrose/corn meal/yeast media (Ashburner 1989). Where indicated, flies were cultured on food supplemented to a final concentration of 640 µg/ml DOX for the experimental group. Each of the hUbbWT(70,80), and hUbb[+1](1,11) transgenic strains, and Oregon R wild-type flies (provided by Bloomington Drosophila stock center) was crossed to the "TO-daughterless" driver line, which contains the daughterless-GAL4 driver and the "901" bridge construct where a UAS-promoter drives expression of rtTAM2alt (Stebbins et al. 2001; Ford et al. 2007). Crosses were performed at 25° C. in urine specimen bottles. Prior to eclosion of the majority of pupae, bottles were cleared of adult parents and newly eclosed flies were allowed to emerge over the next 48 hours. Males and females each containing both the target transgene and the driver constructs were scored and collected. At day 4, the males and females were split into experimental and control groups, each group containing 75-100 flies. These were maintained at 29° C. at 25 flies per vial. All flies were transferred every two days into fresh media for the first month and then every day for the following months. The number of dead flies was counted at each tossing and used to calculate mean and median life spans for the experimental (+DOX) and control (−DOX) groups. The statistical significance of the difference in median life span was calculated for each experiment using log rank tests. Northern analyses. Each of the indicated hUbbWT(70,80, 118), hAppWT(1,24), hUbb[+1](1,11) and Oregon R control strain was crossed to the rtTA(3)E2 driver line (Bieschke et al. 1998) and cultured at 25° C. in urine specimen bottles. Males containing both the transgene and the rtTA(3)E2 driver were scored and collected. The males were then split into experimental and control group, each containing 100 flies. These were maintained at 25° C. at 25 flies per vial. Flies were cultured on plus and minus DOX food for two weeks, and total RNA was isolated from 30 adult Drosophila males using the RNAqueous kit (Ambion), fractionated on 1.0% agarose gels and transferred to GeneScreen membranes (DuPont/MEN). 1X=5 µg, and 2X=10 µg.

The PCR product UBBwt-1 was used as a specific probe for the hUbbWT gene. The PCR product APPwt-1 was used as a specific probe for the hAppWT gene. Blots were also hybridized with probe specific for ribosomal protein gene Rp49 (O'Connell and Rosbash 1984). DNA probes were $^{32}$P-labelled using the Prime-It II DNA labeling kit (Stratagene). Hybridization was carried out in Church-Gilbert solution at 65° C. overnight. Hybridization signals were visualized and quantified using the phosphoimager and ImageQuant software (Molecular Dynamics). Developmental effects of hUbbWT and hUbb[+1] overexpression on life span. Flies were cultured on food supplemented to a final concentration of 640 µg/ml Doxycycline for the experimental group. Each line of hUbbWT(70,80) and hUbb[+1] (1,11) males were mated to virgins of the "TO-daughterless" driver described above, in food bottles plus dox or minus DOX. The progeny were allowed to develop in the plus and minus dox conditions. Prior to eclosion, bottles were cleared of adult parents and newly eclosed flies were allowed to emerge over the next 72 hours. The pupae from both plus and minus DOX bottles were scored for any noticeable phenotype. At eclosion, all the possible combinations of phenotype were scored for each cross and condition. Progeny containing both the transgene and the drivers were screened and collected. Progeny from the plus DOX bottles were separated into males and females and lifespan assay was carried out for these two groups on minus DOX vials. Progeny from the minus DOX bottles were also separated into males and females and put on both plus DOX and minus DOX vials to generate four groups. Therefore a total of six groups were generated per line. The flies were transferred into fresh vials of plus DOX and minus DOX food at 29° C. every other day for the 1st month and then every day until zero survival. Molecular misreading reporter lines irradiation treatment assay. MM-ATG 58A, 46A, 34A, 8A, 46B, 8B, MMC-ATG X, and X2 males and females were cultured for one month on food containing plus dox (640 ug/ml doxycycline) for the experimental, experimental control and minus dox (640 ug/ml ampicillin) for the negative control. The negative and experimental control groups are not exposed to the irradiation. Each of the experimental lines was irradiated for 9 hours (total 50,000 rads). The flies were transferred into fresh vials of appropriate plus and minus DOX food each day until zero survival. At every five days after the irradiation, each of the experimental and control lines were observed under a GFP fluorescent microscope (Leica) for GFP expression.

Molecular misreading reporter lines 100% oxygen survival assay. From each of the lines MM-ATG 58A, 46A, 34A, 8A, 46B, 8B, MMC-ATG X, and X2, males and females were cultured for one month on food containing plus DOX (640 µg/ml DOX) for the experimental. Experimental groups were then transferred to an enclosed chamber with 100% oxygen gas flow (Landis et al. 2004). The flies were transferred into fresh vials of appropriate plus and minus DOX each day until zero survival. Every 24 hrs each of the experimental and control lines were observed under a GFP fluorescent microscope (Leica) for GFP expression. Western analyses. Several antibody reagents were purchased from Upstate cell signaling solutions, including Anti-App (Catalog #07-667) and Anti-Ubb (Catalog #07-375), as well as antibody specific for hApp[+1] ("Amy-5") and antibody specific for hUbb[+1] ("Ubi2a"), both characterized previously (van Leeuwen et al. 1998). For each of the lines, 30 flies from the experimental group (+DOX) and 30 flies from the control group (DOX) were collected at 26 days (Time point 1), 48 days (Time point 2), 67 days (Time point 3), 82 days (Time point 4) and 105 days (Time point 5) for Western analyses. Thirty adult flies were homogenized in Laemmli sample buffer (Bio-Rad) and dilutions were made from the supernatant. The samples were boiled for 10 mins, cooled and fractionated on SDS-PAGE. Stacking gel was 4% and the running gel was 12% for the Ubb+1 and 7.5% for the App[+1]. The samples were transferred to the nitrocellulose membrane (Bio-Rad) and the membrane was blocked overnight at 4° C. in PBST supplemented with 5% Non-Fat Dry Milk (Bio-Rad). Next the nitrocellulose membrane was incubated with 1:2000 of primary antibody specific to Ubb[+1] or specific to the App[+1]. The antibody diluent was made fresh each time in 1% BSA/PBST and incubated overnight at 4° C. Horseradish peroxidase-conjugated goat anti-rabbit secondary antibody (Amersham) was diluted to 1:3000 in 1% BSA/PBST and incubated at room temperature for 2 hours. After washing steps, the samples were briefly incubated in chemiluminescence reagent plus (Perkin Elmer) and the bands were detected using Kodak Image Station. Additional Western control experiments utilized mouse monoclonal antibody 22c11 (Millipore/Chemicon), specific for the N-terminus of hApp, and cortical neuron lysates as a positive control for App (data not shown).

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

Abraham, M. C. and S. Shaham, 2004. Death without caspases, caspases without death. Trends Cell Biol. 14, 184-93.

Ackermann, M., S. C. Stearns and U. Jenal, 2003. Senescence in a bacterium with asymmetric division. Science 300, 1920.

Adams, J. M., 2003. Ways of dying: multiple pathways to apoptosis. Genes Dev. 17, 2481-95.

Adams, J. M. and S. Cory, 2002. Apoptosomes: engines for caspase activation. Curr. Opin. Cell Biol. 14, 715-20.

Aigaki, T., K. H. Seong and T. Matsuo, 2002. Longevity determination genes in Drosophila melanogaster. Mech. Ageing Dev. 123, 1531-41.

Amador-Noguez, D., J. Zimmerman, S. Venable and G. Darlington, 2005. Gender-specific alterations in gene expression and loss of liver sexual dimorphism in the long-lived Ames dwarf mice. Biochem. Biophys. Res. Commun. 332, 1086-100.

Amikura, R., K. Sato and S. Kobayashi, 2005. Role of mitochondrial ribosome-dependent translation in germ-line formation in Drosophila embryos. Mech. Dev 122, 1087-93.

An, J. H., K. Vranas, M. Lucke, H. Inoue, N. Hisamoto, K. Matsumoto and T. K. Blackwell, 2005. Regulation of the Caenorhabditis elegans oxidative stress defense protein SKN-1 by glycogen synthase kinase-3. Proc. Natl. Acad. Sci. USA 102, 16275-80.

Arama, E., J. Agapite and H. Steller, 2003. Caspase activity and a specific cytochrome C are required for sperm differentiation in Drosophila. Dev. Cell 4, 687-97.

Arama, E., M. Bader, M. Srivastava, A. Bergmann and H. Steller, 2005. The two Drosophila cytochrome C proteins can function in both respiration and caspase activation. Embo J.

Arbeitman, M. N., E. E. Furlong, F. Imam, E. Johnson, B. H. Null, B. S. Baker, M. A. Krasnow, M. P. Scott, R. W. Davis and K. P. White, 2002. Gene expression during the life cycle of Drosophila melanogaster. Science 297, 2270-5.

Ayyadevara, S., R. Ayyadevara, A. Vertino, A. Galecki, J. J. Thaden and R. J. Shmookler Reis, 2003. Genetic loci modulating fitness and life span in Caenorhabditis elegans: categorical trait interval mapping in CL2a×Bergerac-BO recombinant-inbred worms. Genetics 163, 557-70.

Baehrecke, E. H., 2002. How death shapes life during development. Nat. Rev. Mol. Cell. Biol. 3, 779-87.

Baehrecke, E. H., 2003. Autophagic programmed cell death in Drosophila. Cell Death Differ. 10, 940-5.

Bartke, A., 2005. Minireview: role of the growth hormone/insulin-like growth factor system in mammalian aging. Endocrinology 146, 3718-23.

Bartke, A. and H. Brown-Borg, 2004. Life extension in the dwarf mouse. Curr. Top. Dev. Biol. 63, 189-225.

Bauer, J. H., P. C. Poon, H. Glatt-Deeley, J. M. Abrams and S. L. Helfand, 2005. Neuronal expression of p53 dominant-negative proteins in adult Drosophila melanogaster extends life span. Curr. Biol. 15, 2063-8.

Bazinet, C., 2004. Endosymbiotic origins of sex. Bioessays 26, 558-66.

Bazinet, C. and J. E. Rollins, 2003. Rickettsia-like mitochondrial motility in Drosophila spermiogenesis. Evol. Dev. 5, 379-85.

Bhadra, M. P., U. Bhadra, J. Kundu and J. A. Birchler, 2005. Gene expression analysis of the function of the male-specific lethal complex in Drosophila. Genetics 169, 2061-74.

Birchler, J. A., M. Pal-Bhadra and U. Bhadra, 2003. Dosage dependent gene regulation and the compensation of the X chromosome in Drosophila males. Genetica 117, 179-90.

Brookes, P. S., 2005. Mitochondrial H(+) leak and ROS generation: an odd couple. Free Radic. Biol. Med. 38, 12-23.

Burger, J. M. and D. E. Promislow, 2004. Sex-specific effects of interventions that extend fly life span. Sci. Aging Knowledge Environ. 2004, pe30.

Burt, A. and R. Trivers, 2006. Genes and Conflict. Harvard Press, Belknap. Busuttil, R. A., M. Rubio, M. E. Dolle, J. Campisi and J. Vijg, 2003. Oxygen accelerates the accumulation of mutations during the senescence and immortalization of murine cells in culture. Aging Cell 2, 287-94.

Buszczak, M. and L. Cooley, 2000. Eggs to die for: cell death during Drosophila oogenesis. Cell Death Differ. 7, 1071-4.

Carrel, L. and H. F. Willard, 2005. X-inactivation profile reveals extensive variability in X-linked gene expression in females. Nature 434, 400-4.

Cashio, P., T. V. Lee and A. Bergmann, 2005. Genetic control of programmed cell death in Drosophila melanogaster. Semin. Cell Dev. Biol. 16, 225-35.

Charlesworth, D. and B. Charlesworth, 2005. Sex chromosomes: evolution of the weird and wonderful. Curr. Biol. 15, R129-31.

Chippindale, A. K., J. R. Gibson and W. R. Rice, 2001. Negative genetic correlation for adult fitness between sexes reveals ontogenetic conflict in Drosophila. Proc. Natl. Acad. Sci. USA 98, 1671-5.

Chow, J. C., Z. Yen, S. M. Ziesche and C. J. Brown, 2005. Silencing of the mammalian X chromosome. Annu. Rev. Genomics Hum. Genet. 6, 69-92.

Clancy, D. J., D. Gems, L. G. Harshman, S. Oldham, H. Stocker, E. Hafen, S. J. Leevers and L. Partridge, 2001. Extension of life-span by loss of CHICO, a Drosophila insulin receptor substrate protein. Science 292, 104-106.

Corona, M., K. A. Hughes, D. B. Weaver and G. E. Robinson, 2005. Gene expression patterns associated with queen honey bee longevity. Mech. Ageing Dev. 126, 1230-8.

Cox, R. T. and A. C. Spradling, 2003. A Balbiani body and the fusome mediate mitochondrial inheritance during Drosophila oogenesis. Development 130, 1579-90.

Cypser, J. R. and T. E. Johnson, 2003. Hormesis in Caenorhabditis elegans dauerdefective mutants. Biogerontology 4, 203-14.

Dawkins, R., 1976. The selfish gene. Oxford University Press, Oxford.

De Luca, M., N. V. Roshina, G. L. Geiger-Thornsberry, R. F. Lyman, E. G. Pasyukova and T. F. Mackay, 2003. Dopa decarboxylase (Ddc) affects variation in Drosophila longevity. Nat. Genet. 34, 429-33.

Dillin, A., A. L. Hsu, N. Arantes-Oliveira, J. Lehrer-Graiwer, H. Hsin, A. G. Fraser, R. S. Kamath, J. Ahringer and C. Kenyon, 2002. Rates of behavior and aging specified by mitochondrial function during development. Science 298, 2398-401.

Drummond-Barbosa, D. and A. C. Spradling, 2001. Stem cells and their progeny respond to nutritional changes during Drosophila oogenesis. Dev. Biol. 231, 265-78.

Drysdale, R. A. and M. A. Crosby, 2005. FlyBase: genes and gene models. Nucleic Acids Res. 33, D390-5.

Fabrizio, J. J., G. Rime, S. K. Lemmon and C. Bazinet, 1998. Genetic dissection of sperm individualization in Drosophila melanogaster. Development 125, 1833-43.

Finch, C. E., 1990. Longevity, Senescence and the Genome. University of Chicago Press, Chicago.

Finch, C. E. and R. M. Sapolsky, 1999. The evolution of Alzheimer disease, the reproductive schedule, and apoE isoforms. Neurobiol. Aging 20, 407-28.

Flatt, T., M. P. Tu and M. Tatar, 2005. Hormonal pleiotropy and the juvenile hormone regulation of Drosophila development and life history. Bioessays 27, 999-1010.

Ford, D., et al., Alteration of Drosophila life span using conditional, tissuespecific expression of transgenes triggered by doxycyline or RU486/Mifepristone. Exp Gerontol, 2007.

Ford, D. and J. Tower, 2006. Genetic manipulation of life span in Drosophila melanogaster. Handbook of he Biology of Aging. E. J. Masoro and S. N. Austad. Burlington, Mass., Elsevier: 400-412.

Fridovich, I., 2004. Mitochondria: are they the seat of senescence? Aging Cell 3, 13-6.

Fry, A. J., M. R. Palmer and D. M. Rand, 2004. Variable fitness effects of Wolbachia infection in Drosophila melanogaster. Heredity 93, 379-89.

Fry, A. J. and D. M. Rand, 2002. Wolbachia interactions that determine Drosophila melanogaster survival. Evolution Int. J. Org. Evolution 56, 1976-81.

Garigan, D., A. L. Hsu, A. G. Fraser, R. S. Kamath, J. Ahringer and C. Kenyon, 2002. Genetic analysis of tissue aging in Caenorhabditis elegans: a role for heat-shock factor and bacterial proliferation. Genetics 161, 1101-12.

Gaspari, L., P. Pedotti, M. Bonafe, C. Franceschi, D. Marinelli, D. Mari, S. Garte and E. Taioli, 2003. Metabolic gene polymorphisms and p53 mutations in healthy centenarians and younger controls. Biomarkers 8, 522-8.

Gatza, C., G. Hinkel, L. Moore, M. Dumble and L. A. Donehower, 2006. p53 and mouse aging models. Handbook of the Biology of Aging. E. J. Masoro and S. N. Austad. Burlington, Mass., Elsevier: 149-171.

Gems, D. and J. J. McElwee, 2005. Broad spectrum detoxification: the major longevity assurance process regulated by insulin/IGF-1 signaling? Mech. Ageing Dev. 126, 381-7.

Gerdes, K., S. K. Christensen and A. Lobner-Olesen, 2005. Prokaryotic toxin-antitoxin stress response loci. Nat. Rev. Microbiol. 3, 371-82.

Gibson, J. R., A. K. Chippindale and W. R. Rice, 2002. The X chromosome is a hot spot for sexually antagonistic fitness variation. Proc. Biol. Sci. 269, 499-505.

Good, J. M. and M. W. Nachman, 2005. Rates of protein evolution are positively correlated with developmental timing of expression during mouse spermatogenesis. Mol. Biol. Evol. 22, 1044-52.

Graham, P., J. K. Penn and P. Schedl, 2003. Masters change, slaves remain. Bioessays 25, 1-4.

Graves, J. A., 2006. Sex chromosome specialization and degeneration in mammals. Cell 124, 901-14.

Gray, M. W., G. Burger and B. F. Lang, 1999. Mitochondrial evolution. Science 283, 1476-81.

Hekimi, S. and L. Guarente, 2003. Genetics and the specificity of the aging process. Science 299, 1351-4.

Helfand, S. L. and B. Rogina, 2003. Genetics of aging in the fruit fly, Drosophila melanogaster. Annu. Rev. Genet. 37, 329-48.

Herndon, L. A., P. J. Schmeissner, J. M. Dudaronek, P. A. Brown, K. M. Listner, Y. Sakano, M. C. Paupard, D. H. Hall and M. Driscoll, 2002. Stochastic and genetic factors influence tissue-specific decline in ageing C. elegans. Nature 419, 808-14.

Hogeweg, P. and N. Takeuchi, 2003. Multilevel selection in models of prebiotic evolution: compartments and spatial self-organization. Orig. Life Evol. Biosph. 33, 375-403.

Honda, Y. and S. Honda, 1999. The daf-2 gene network for longevity regulates oxidative stress resistance and Mn-superoxide dismutase gene expression in Caenorhabditis elegans. FASEB J. 13, 1385-1393.

Hsu, H. C., L. Li, H. G. Zhang and J. D. Mountz, 2005. Genetic regulation of thymic involution. Mech. Ageing Dev. 126, 87-97.

Hughes, K. A. and R. M. Reynolds, 2005. Evolutionary and mechanistic theories of aging. Annu. Rev. Entomol. 50, 421-45.

Hussein, M. R., 2005. Apoptosis in the ovary: molecular mechanisms. Hum. Reprod. Update 11, 162-77.

Hwangbo, D. S., B. Gersham, M. P. Tu, M. Palmer and M. Tatar, 2004. Drosophila dFOXO controls lifespan and regulates insulin signaling in brain and fat body. Nature 429, 562-6.

Jackson, A. U., A. T. Galecki, D. T. Burke and R. A. Miller, 2002. Mouse loci associated with life span exhibit sex-specific and epistatic effects. J. Gerontol. A: Biol. Sci. Med. Sci. 57, B9-B15.

Jones, A., 2000. Does the plant mitochondrion integrate cellular stress and regulate programmed cell death? Trends Plant Sci. 5, 225-30.

Kenyon, C., 2005. The plasticity of aging: insights from long-lived mutants. Cell 120, 449-60.

Kirkwood, T. B. L. and S. N. Austad, 2000. Why do we age? Nature 409, 233-238.

Kloc, M., S. Bilinski and L. D. Etkin, 2004. The Balbiani body and germ cell determinants: 150 years later. Curr. Top. Dev. Biol. 59, 1-36.

Kobayashi, S., K. Sato and Y. Hayashi, 2005. The role of mitochondrial rRNAs and nanos protein in germ-line formation in Drosophila embryos. Zoolog. Sci. 22, 943-54.

Krakauer, D. C. and A. Mira, 1999. Mitochondria and germ-cell death. Nature 400, 125-6.

Kujoth, G. C., A. Hiona, T. D. Pugh, S. Someya, K. Panzer, S. E. Wohlgemuth, T. Hofer, A. Y. Seo, R. Sullivan, W. A. Jobling, J. D. Morrow, H. Van Remmen, J. M. Sedivy, T. Yamasoba, M. Tanokura, R. Weindruch, C. Leeuwenburgh and T. A. Prolla, 2005. Mitochondrial DNA mutations, oxidative stress, and apoptosis in mammalian aging. Science 309, 481-4.

Landis, G. N., D. Bhole and J. Tower, 2003. A search for doxycycline-dependent mutations that increase Drosophila melanogaster life span identifies the VhaSFD, Sugar baby, filamin, fwd and Cctl genes. Genome Biol 4, R8.

Landis, G. N. and J. Tower, 2005. Superoxide dismutase evolution and life span regulation. Mech. Ageing Dev. 126, 365-79.

Lang, B. F., M. W. Gray and G. Burger, 1999. Mitochondrial genome evolution and the origin of eukaryotes. Annu. Rev. Genet. 33, 351-97.

Larsen, P. L., 1993. Aging and resistance to oxidative damage in *Caenorhabditis elegans*. Proc. Natl. Acad. Sci. USA 90, 8905-9.

Lee, S. S., S. Kennedy, A. C. Tolonen and G. Ruvkun, 2003. DAF-16 target genes that control *C. elegans* life-span and metabolism. Science 300, 644-7.

Lee, S. S., R. Y. Lee, A. G. Fraser, R. S. Kamath, J. Ahringer and G. Ruvkun, 2003. A systematic RNAi screen identifies a critical role for mitochondria in *C. elegans* longevity. Nat. Genet. 33, 40-8.

Leips, J., P. Gilligan and T. F. Mackay, 2005. Quantitative Trait Loci with Age-Specific Effects on Fecundity in *Drosophila melanogaster*. Genetics.

Leips, J. and T. F. Mackay, 2000. Quantitative trait loci for life span in *Drosophila melanogaster*: interactions with genetic background and larval density. Genetics 155, 1773-88.

Line, M. A., 2005. A hypothetical pathway from the RNA to the DNA world. Orig. Life Evol. Biosph. 35, 395-400.

Luckinbill, L. S., R. Arking, M. Clare, W. Cirocco and S. Buck, 1984. Selection for delayed senescence in *Drosophila melanogaster*. Evolution 38, 996-1003.

Mackay, T. F. C., 2002. The nature of quantitative genetic variation for *Drosophila* longevity. Mech. Ageing Dev. 123, 95-104.

Magwere, T., T. Chapman and L. Partridge, 2004. Sex differences in the effect of dietary restriction on life span and mortality rates in female and male *Drosophila melanogaster*. J. Gerontol. A: Biol. Sci. Med. Sci. 59, 3-9.

Maier, B., W. Gluba, B. Bernier, T. Turner, K. Mohammad, T. Guise, A. Sutherland, M. Thorner and H. Scrable, 2004. Modulation of mammalian life span by the short isoform of p53. Genes Dev. 18, 306-19.

Mair, W., P. Goymer, S. D. Pletcher and L. Partridge, 2003. Demography of dietary restriction and death in *Drosophila*. Science 301, 1731-3.

Martin, G. M., 2005. Genetic modulation of senescent phenotypes in *Homo sapiens*. Cell 120, 523-32.

Masoro, E. J., 2005. Overview of caloric restriction and ageing. Mech. Ageing Dev. 126, 913-22.

McCulloch, D. and D. Gems, 2003. Evolution of male longevity bias in nematodes. Aging Cell 2, 165-73.

Miller, P. M., S. Gavrilets and W. R. Rice, 2006. Sexual conflict via maternal-effect genes in ZW species. Science 312, 73.

Miller, R. A., 2005. Genetic approaches to the study of aging. J. Am. Geriatr. Soc. 53, S284-6.

Murphy, C. T., S. A. McCarroll, C. I. Bargmann, A. Fraser, R. S. Kamath, J. Ahringer, H. Li and C. Kenyon, 2003. Genes that act downstream of DAF-16 to influence the lifespan of *Caenorhabditis elegans*. Nature.

Nielsen, R., C. Bustamante, A. G. Clark, S. Glanowski, T. B. Sackton, M. J. Hubisz, A. Fledel-Alon, D. M. Tanenbaum, D. Civello, T. J. White, J. S. J, M. D. Adams and M. Cargill, 2005. A scan for positively selected genes in the genomes of humans and chimpanzees. PLoS Biol. 3, e170.

Nilsen, J. and R. D. Brinton, 2004. Mitochondria as therapeutic targets of estrogen action in the central nervous system. Curr. Drug Targets CNS Neurol. Disord. 3, 297-313.

Nishimura, Y., T. Yoshinari, K. Naruse, T. Yamada, K. Sumi, H. Mitani, T. Higashiyama and T. Kuroiwa, 2006. Active digestion of sperm mitochondrial DNA in single living sperm revealed by optical tweezers. Proc. Natl. Acad. Sci. USA.

Nowak, M. A. and K. Sigmund, 2004. Evolutionary dynamics of biological games. Science 303, 793-9.

Nuzhdin, S. V., A. A. Khazaeli and J. W. Curtsinger, 2005. Survival analysis of life span quantitative trait loci in *Drosophila melanogaster*. Genetics 170, 719-31.

Nuzhdin, S. V., E. G. Pasyukova, C. L. Dilda, Z. -B. Zeng and T. F. C. Mackay, 1997. Sex-specific quantitative trait loci affecting longevity in *Drosophila melanogaster*. Proc. Natl. Acad. Sci. USA 94, 9734-9739.

Ohki, R., T. Tsurimoto and F. Ishikawa, 2001. In vitro reconstitution of the end replication problem. Mol. Cell. Biol. 21, 5753-66.

Oliver, B. and M. Parisi, 2004. Battle of the Xs. Bioessays 26, 543-8.

Olovnikov, A. M., 1973. A theory of marginotomy. The incomplete copying of template margin in enzymic synthesis of polynucleotides and biological significance of the phenomenon. J. Theor. Biol. 41, 181-90.

Parisi, M., R. Nuttall, P. Edwards, J. Minor, D. Naiman, J. Lu, M. Doctolero, M. Vainer, C. Chan, J. Malley, S. Eastman and B. Oliver, 2004. A survey of ovary-, testis-, and soma-biased gene expression in *Drosophila melanogaster* adults. Genome Biol. 5, R40.

Parisi, M., R. Nuttall, D. Naiman, G. Bouffard, J. Malley, J. Andrews, S. Eastman and B. Oliver, 2003. Paucity of genes on the *Drosophila* X chromosome showing malebiased expression. Science 299, 697-700.

Parkes, T. L., A. J. Elia, D. Dickson, A. J. Hilliker, J. P. Phillips and G. L. Boulianne, 1998. Extension of *Drosophila* lifespan by overexpression of human SOD1 in motorneurons. Nature Genet. 19, 171-174.

Partridge, L., S. D. Pletcher and W. Mair, 2005. Dietary restriction, mortality trajectories, risk and damage. Mech. Ageing Dev. 126, 35-41.

Pepling, M. E. and A. C. Spradling, 2001. Mouse ovarian germ cell cysts undergo programmed breakdown to form primordial follicles. Dev. Biol. 234, 339-51.

Perls, T. and D. Terry, 2003. Genetics of exceptional longevity. Exp. Gerontol. 38, 725-30.

Rand, D. M., 2005. Mitochondrial genetics of aging: intergenomic conflict resolution. Sci. Aging Knowledge Environ. 2005, re5.

Rand, D. M., A. G. Clark and L. M. Kann, 2001. Sexually antagonistic cytonuclear fitness interactions in *Drosophila melanogaster*. Genetics 159, 173-87.

Rand, D. M., A. Fry and L. Sheldahl, 2006. Nuclear-mitochondrial epistasis and *Drosophila* aging: introgression of *Drosophila simulans* mtDNA modifies longevity in *D. melanogaster* nuclear backgrounds. Genetics 172, 329-41.

Rauser, C. L., J. J. Tierney, S. M. Gunion, G. M. Covarrubias, L. D. Mueller and M. R. Rose, 2006. Evolution of late-life fecundity in *Drosophila melanogaster*. J. Evol. Biol. 19, 289-301.

Reiwitch, S. G. and S. V. Nuzhdin, 2002. Quantitative trait loci for lifespan of mated *Drosophila melanogaster* affect both sexes. Genet Res 80, 225-30.

Rice, W. R., 1992. Sexually antagonistic genes: experimental evidence. Science 256, 1436-9.

Rice, W. R., 1998. Male fitness increases when females are eliminated from gene pool: implications for the Y chromosome. Proc. Natl. Acad. Sci. USA 95, 6217-21.

Richards, S., Y. Liu, B. R. Bettencourt, P. Hradecky, S. Letovsky, R. Nielsen, K. Thornton, M. J. Hubisz, R. Chen, R. P. Meisel, O. Couronne, S. Hua, M. A. Smith, P. Zhang, J. Liu, H. J. Bussemaker, M. F. van Batenburg, S. L. Howells, S. E. Scherer, E. Sodergren, B. B. Matthews, M. A. Crosby, A. J. Schroeder, D. Ortiz-Barrientos, C. M. Rives, M. L. Metzker, D. M. Muzny, G. Scott, D. Steffen, D. A. Wheeler, K. C. Worley, P. Havlak, K. J. Durbin, A. Egan, R. Gill, J. Hume, M.

B. Morgan, G. Miner, C. Hamilton, Y. Huang, L. Waldron, D. Verduzco, K. P. Clerc-Blankenburg, I. Dubehak, M. A. Noor, W. Anderson, K. P. White, A. G. Clark, S. W. Schaeffer, W. Gelbart, G. M. Weinstock and R. A. Gibbs, 2005. Comparative genome sequencing of *Drosophila pseudoobscura*: chromosomal, gene, and cis-element evolution. Genome Res. 15, 1-18.

Rose, M. R., 1984. Laboratory evolution of postponed senescence in *Drosophila melanogaster*. Evolution 38, 1004-1010.

Scheuring, I., T. Czaran, P. Szabo, G. Karolyi and Z. Toroczkai, 2003. Spatial models of prebiotic evolution: soup before pizza? Orig. Life Evol. Biosph. 33, 319-55.

Searcy, D. G., 2003. Metabolic integration during the evolutionary origin of mitochondria. Cell Res, 13, 229-38.

Spees, J. L., S. D. Olson, M. J. Whitney and D. J. Prockop, 2006. Mitochondrial transfer between cells can rescue aerobic respiration. Proc. Natl. Acad. Sci. USA.

Spencer, C. C., C. E. Howell, A. R. Wright and D. E. Promislow, 2003. Testing an 'aging gene' in long-lived *Drosophila* strains: increased longevity depends on sex and genetic background. Aging Cell 2, 123-30.

Starr, D. J. and T. W. Cline, 2002. A host parasite interaction rescues *Drosophila* oogenesis defects. Nature 418, 76-9.

Stewart, E. J., R. Madden, G. Paul and F. Taddei, 2005. Aging and death in an organism that reproduces by morphologically symmetric division. PLoS Biol. 3, e45.

Sun, J., D. Folk, T. J. Bradley and J. Tower, 2002. Induced overexpression of mitochondrial Mn-superoxide dismutase extends the life span of adult *Drosophila melanogaster*. Genetics 161, 661-72.

Sun, J. and J. Tower, 1999. FLP recombinase-mediated induction of Cu/Zn-superoxide dismutase transgene expression can extend the life span of adult *Drosophila melanogaster* flies. Mol. Cell. Biol. 19, 216-28.

Szathmary, E., 2000. The evolution of replicators. Philos. Trans. R. Soc. Lond. B: Biol. Sci. 355, 1669-76.

Tatar, M., A. A. Khazaeli and J. W. Curtsinger, 1997. Chaperoning extended life. Nature 390, 30.

Tatar, M., A. Kopelman, D. Epstein, M. P. Tu, C. M. Yin and R. S. Garofalo, 2001. A mutant *Drosophila* insulin receptor homolog that extends life-span and impairs neuroendocrine function. Science 292, 107-10.

Timmis, J. N., M. A. Ayliffe, C. Y. Huang and W. Martin, 2004. Endosymbiotic gene transfer: organelle genomes forge eukaryotic chromosomes. Nat. Rev. Genet. 5, 123-35.

Tyner, S. D., S. Venkatachalam, J. Choi, S. Jones, N. Ghebranious, H. Igelmann, X. Lu, G. Soron, B. Cooper, C. Brayton, S. Hee Park, T. Thompson, G. Karsenty, A. Bradley and L. A. Donehower, 2002. p53 mutant mice that display early ageingassociated phenotypes. Nature 415, 45-53.

Valenzuela, R. K., S. N. Forbes, P. Keim and P. M. Service, 2004. Quantitative trait loci affecting life span in replicated populations of *Drosophila melanogaster*. II. Response to selection. Genetics 168, 313-24.

van Heemst, D., S. P. Mooijaart, M. Beekman, J. Schreuder, A. J. de Craen, B. W. Brandt, P. E. Slagboom and R. G. Westendorp, 2005. Variation in the human TP53 gene affects old age survival and cancer mortality. Exp. Gerontol. 40, 11-5.

Vieira, C., E. G. Pasyukova, Z. B. Zeng, J. B. Hackett, R. F. Lyman and T. F. Mackay, 2000. Genotype-environment interaction for quantitative trait loci affecting life span in *Drosophila melanogaster*. Genetics 154, 213-27.

Vina, J., C. Borras, J. Gambini, J. Sastre and F. V. Pallardo, 2005. Why females live longer than males: control of longevity by sex hormones. Sci. Aging Knowledge Environ. 2005, pe17.

Walker, G. A., T. M. White, G. McColl, N. L. Jenkins, S. Babich, E. P. Candido, T. E. Johnson and G. J. Lithgow, 2001. Heat shock protein accumulation is upregulated in a long-lived mutant of *Caenorhabditis elegans*. J. Gerontol. A: Biol. Sci. Med. Sci. 56, B281-7.

Wallace, D.C., 2005. A Mitochondrial Paradigm of Metabolic and Degenerative Diseases, Aging, and Cancer: A Dawn for Evolutionary Medicine. Annu. Rev. Genet.

Walter, R., D. M. Murasko and F. Sierra, 1998. T-kininogen is a biomarker of senescence in rats. Mech. Ageing Dev. 106, 129-44.

Wang, M. H., O. Lazebny, L. G. Harshman and S. V. Nuzhdin, 2004. Environment-dependent survival of *Drosophila melanogaster*: a quantitative genetic analysis. Aging Cell 3, 133-40.

Wilk, K., S. Bilinski, M. T. Dougherty and M. Kloc, 2005. Delivery of germinal granules and localized RNAs via the messenger transport organizer pathway to the vegetal cortex of *Xenopus oocytes* occurs through directional expansion of the mitochondrial cloud. Int. J. Dev. Biol. 49, 17-21.

Wolfner, M. F., 2002. The gifts that keep on giving: physiological functions and evolutionary dynamics of male seminal proteins in *Drosophila*. Heredity 88, 85-93.

Yin, V. P. and C. S. Thummel, 2005. Mechanisms of steroid-triggered programmed cell death in *Drosophila*. Semin. Cell Dev. Biol. 16, 237-43.

Zheng, J., S. W. Edelman, G. Tharmarajah, D. W. Walker, S. D. Pletcher and L. Seroude, 2005. Differential patterns of apoptosis in response to aging in *Drosophila*. Proc. Natl. Acad. Sci. USA 102, 12083-8.

TABLES

TABLE 1

Distribution of genes in various GO categories among *Drosophila* chromosomes (Source: Flybase (Drysdale and Crosby, 2005)).

| Gene category | X | 2 | 3 | Total | Skew? |
|---|---|---|---|---|---|
| TOTAL | 2309 (16%) | 5688 (40%) | 6302 (44%) | 14384 | (base) |
| Sex determination | 11 (30%) | 13 (35%) | 13 (35%) | 37 | X |
| Oogenesis | 61 (30%) | 66 (33%) | 76 (37%) | 203 | X |
| Spermatogenesis | 9[a] (11%) | 48 (57%) | 27 (32%) | 84 | A |
| Mitochondrial | 43 (17%) | 91 (36%) | 120 (47%) | 254 | (none) |
| Apoptosis/cell death | 28 (11%) | 107 (43%) | 112 (45%) | 247 | A |
| Anti-apoptosis | 3 (7%) | 19 (45%) | 20 (47%) | 42 | A |

[a]The eleven-copy stellate locus was counted as one gene.

TABLE 2

*Drosophila* X chromosome programmed cell death genes sorted by function.

| Gene Name | Anti-apoptosis | Apoptosis | Induction of Apoptosis | Apoptoic program | Autophagic cell death | Autophagy | Salivary gland cell death | Germ cell programmed death | Retinal cell death | Positive regulation of retinal programmed cell death |
|---|---|---|---|---|---|---|---|---|---|---|
| Mvb | X | | | | | | | | | |
| Sk1 | X | | | | | | | | | |
| CG32703 | X | | | | | | | | | |
| Tak1 | | X | | | | | | | | |
| wgn | | X | | | | | | | | |
| CG17754 | | X | | | | | | | | |
| Dredd | | X | | X | | | | | | |
| Arg5/CG1643 | | X | | | X | X | X | | | |
| Ing3/CG6632 | | X | X | | | | | | | |
| CG10990 | | X | X | | | | | | | |
| Corp/CG10965 | | | X | | | | | | | |
| mnb | | | X | | | | | | | |
| Traf2 | | | X | | | | | | | |
| Tao.1/CG14217 | | | X | | | | | | | |
| CG32666 | | | X | | | | | | | |
| Appl | | X | X | | | | | | | |
| kirre | | | X | | | | | | | |
| rst | | | X | | | | | | X | |
| ec/CG2904 | | | | | | | | | X | |
| N/CG3936 | | | | | | | | | X | |
| lz/CG1689 | | | | | | | | | | X |
| br | | | | | X | X | | | | |
| Cyp1 | | | | X | | X | | | | |
| 1(1)G0148 | | | | X | | X | | | | |
| CG5254 | | | | X | | X | | | | |
| CG7860 | | | | X | | X | | | | |
| CG10992 | | | | X | | X | | | | |
| usp/CG4380 | | | | X | | | | | | |
| Tre1/CG3171 | | | | | | | | X | | |

TABLE 3

Some *Drosophila* genes with maternally-rescued phenotypes[a]

| | Abbreviation | gene name | chromosome |
|---|---|---|---|
| 1 | abo | abnormal oocyte | 2 |
| 2 | Akt1 | Akt1 | 3 |
| 3 | arm | armadillo | X |
| 4 | cos | costa | 2 |
| 5 | da | daughterless | 2 |
| 6 | Dfd | Deformed | 3 |
| 7 | dl | dorsal | 2 |
| 8 | Dl | Delta | 3 |
| 9 | dpp | decapentaplegic | 2 |
| 10 | dsh | dishevelled | X |
| 11 | Dsor1 | Downstream of raf1 | X |
| 12 | ecd | ecdysoneless | 3 |
| 13 | fliI | flightless I | X |
| 14 | fu | fused | X |
| 15 | Gβ13F | G protein β-subunit 13F | X |
| 16 | hb | hunchback | 3 |
| 17 | hep | hemipterous | X |
| 18 | N | Notch | X |
| 19 | ncd | non-claret disjunctional | 3 |
| 20 | oc | ocelliless | X |
| 21 | Pu | Punch | 2 |
| 22 | pum | pumilio | 3 |
| 23 | retn | retained | 2 |
| 24 | RpII15 | RNA polymerase II 15 kD subunit | 3 |
| 25 | Sce | Sex combs extra | 3 |
| 26 | sgg | shaggy | X |
| 27 | smo | smoothened | 2 |
| 28 | Stat92E | Signal-transducer and activator of transcription protein at 92E | 3 |
| 29 | Su(fu) | Suppressor of fused | 3 |
| 30 | Sxl | Sex lethal | X |
| 31 | tkv | thickveins | 2 |

[a] Genes listed in Flybase with phenotype descriptors matching key words maternally AND rescued AND lethal.

What is claimed is:

1. A method for modulating cellular senescence of a mammalian cell carrying a XIST gene, comprising:
   administering to the cell an agent capable of activating or modulating the XIST gene,
   wherein said agent is an RNA having a sequence identical, substituting u for t to SEQ ID NO: 3.

2. The method of claim 1, wherein said mammalian cell is a human cell.

3. The method of claim 1, wherein the administering step is by way of a biological vector engineered to produce the RNA in the cell.

* * * * *

SEQUENCE LISTING

<160> NUMBER OF SEQ ID NOS: 24

<210> SEQ ID NO 1
<211> LENGTH: 25
<212> TYPE: DNA
<213> ORGANISM: Artificial

```
<220> FEATURE:
<223> OTHER INFORMATION: Primer

<400> SEQUENCE: 1
ggctgcagga attcgatatc aagct                                         25

<210> SEQ ID NO 2
<211> LENGTH: 32
<212> TYPE: DNA
<213> ORGANISM: Artificial
<220> FEATURE:
<223> OTHER INFORMATION: Primer

<400> SEQUENCE: 2
tttattaagg cacagtcgag gctgatcagc ga                                 32

<210> SEQ ID NO 3
<211> LENGTH: 29
<212> TYPE: DNA
<213> ORGANISM: Artificial
<220> FEATURE:
<223> OTHER INFORMATION: Primer

<400> SEQUENCE: 3
tgcaggctgc aggaattcga tatcaagct                                     29

<210> SEQ ID NO 4
<211> LENGTH: 36
<212> TYPE: DNA
<213> ORGANISM: Artificial
<220> FEATURE:
<223> OTHER INFORMATION: Primer

<400> SEQUENCE: 4
aatttttatt aaggcacagt cgaggctgat cagcga                             36

<210> SEQ ID NO 5
<211> LENGTH: 25
<212> TYPE: DNA
<213> ORGANISM: Artificial
<220> FEATURE:
<223> OTHER INFORMATION: Primer

<400> SEQUENCE: 5
gatccatgca gatcttcgtg aaaac                                         25

<210> SEQ ID NO 6
<211> LENGTH: 31
<212> TYPE: DNA
<213> ORGANISM: Artificial
<220> FEATURE:
<223> OTHER INFORMATION: Primer

<400> SEQUENCE: 6
tttattccag tgtgatggat atctgcagaa t                                  31

<210> SEQ ID NO 7
<211> LENGTH: 29
<212> TYPE: DNA
<213> ORGANISM: Artificial
<220> FEATURE:
<223> OTHER INFORMATION: Primer

<400> SEQUENCE: 7
tgcagatcca tgcagatctt cgtgaaaac                                     29
```

```
<210> SEQ ID NO 8
<211> LENGTH: 35
<212> TYPE: DNA
<213> ORGANISM: Artificial
<220> FEATURE:
<223> OTHER INFORMATION: Primer

<400> SEQUENCE: 8
aatttttatt ccagtgtgat ggatatctgc agaat                         35

<210> SEQ ID NO 9
<211> LENGTH: 25
<212> TYPE: DNA
<213> ORGANISM: Artificial
<220> FEATURE:
<223> OTHER INFORMATION: Primer

<400> SEQUENCE: 9
gtgctggaat tctgcagata tccat                                    25

<210> SEQ ID NO 10
<211> LENGTH: 31
<212> TYPE: DNA
<213> ORGANISM: Artificial
<220> FEATURE:
<223> OTHER INFORMATION: Primer

<400> SEQUENCE: 10
tttattcgag gtcgacggta tcgattctta a                             31

<210> SEQ ID NO 11
<211> LENGTH: 29
<212> TYPE: DNA
<213> ORGANISM: Artificial
<220> FEATURE:
<223> OTHER INFORMATION: Primer

<400> SEQUENCE: 11
tgcagtgctg gaattctgca gatatccat                                29

<210> SEQ ID NO 12
<211> LENGTH: 35
<212> TYPE: DNA
<213> ORGANISM: Artificial
<220> FEATURE:
<223> OTHER INFORMATION: Primer

<400> SEQUENCE: 12
aatttttatt cgaggtcgac ggtatcgatt cttaa                         35

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
tagaactagt ggatccccg ggaga                                     25

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
```

```
tttattctcg ttggctgctt cctgttccaa                                    30

<210> SEQ ID NO 15
<211> LENGTH: 29
<212> TYPE: DNA
<213> ORGANISM: Artificial
<220> FEATURE:
<223> OTHER INFORMATION: Primer

<400> SEQUENCE: 15
tgcatagaac tagtggatcc cccgggaga                                     29

<210> SEQ ID NO 16
<211> LENGTH: 34
<212> TYPE: DNA
<213> ORGANISM: Artificial
<220> FEATURE:
<223> OTHER INFORMATION: Primer

<400> SEQUENCE: 16 aattttatt ctcgttggct gcttcctgtt ccaa                                34

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
gtgagcaagg gcgaggagct                                               20

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
ttacttgtac agctcgtcca                                               20

<210> SEQ ID NO 19
<211> LENGTH: 25
<212> TYPE: DNA
<213> ORGANISM: Artificial
<220> FEATURE:
<223> OTHER INFORMATION: Primer

<400> SEQUENCE: 19
agctcgtgag caagggcgag gagct                                         25

<210> SEQ ID NO 20
<211> LENGTH: 24
<212> TYPE: DNA
<213> ORGANISM: Artificial
<220> FEATURE:
<223> OTHER INFORMATION: Primer

<400> SEQUENCE: 20
aattttactt gtacagctcg tcca                                          24

<210> SEQ ID NO 21
<211> LENGTH: 29
<212> TYPE: DNA
<213> ORGANISM: Artificial
```

```
<220> FEATURE:
<223> OTHER INFORMATION: Synthetic Oligonucleotide

<400> SEQUENCE: 21
atggagagag agagagagag atcgagctc                                        29

<210> SEQ ID NO 22
<211> LENGTH: 28
<212> TYPE: DNA
<213> ORGANISM: Artificial
<220> FEATURE:
<223> OTHER INFORMATION: Synthetic Oligonucleotide

<400> SEQUENCE: 22
cgatctctct ctctctctct ccattgca                                         28

<210> SEQ ID NO 23
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 23
atggagagag agagagagag agagctc                                          27

<210> SEQ ID NO 24
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 24
ctctctctct ctctctctcc attgca                                           26
```